US011331301B2

(12) United States Patent
Koltai et al.

(10) Patent No.: US 11,331,301 B2
(45) Date of Patent: May 17, 2022

(54) COMPOSITIONS AND METHODS FOR TREATING CANCER

(71) Applicants: The State of Israel, Ministry of Agriculture & Rural Development, Agricultural Research Organization (ARO) (Volcani Center), Rishon-LeZion (IL); Mor Research Applications Ltd., Tel-Aviv (IL)

(72) Inventors: Hinanit Koltai, Rishon-LeZion (IL); Yoram Kapulnik, Karmey Yosef (IL); Dvora Namdar, Beit Gamliel (IL); Moran Mazuz, Rishon-LeZion (IL); Ido Laish, Kiryat-Ono (IL); Timna Naftali, Tel-Aviv (IL)

(73) Assignees: The State of Israel, Ministry of Agriculture & Rural Development, Agricultural Research Organization (ARO) (Volcani Center), Rishon-LeZion (IL); Mor Research Applications Ltd., Ramat-Gan (IL)

( * ) Notice: Subject to any disclaimer, the term of this patent is extended or adjusted under 35 U.S.C. 154(b) by 0 days.

(21) Appl. No.: 16/491,243

(22) PCT Filed: Mar. 5, 2018

(86) PCT No.: PCT/IL2018/050249
§ 371 (c)(1),
(2) Date: Sep. 5, 2019

(87) PCT Pub. No.: WO2018/163164
PCT Pub. Date: Sep. 13, 2018

(65) Prior Publication Data
US 2020/0030282 A1    Jan. 30, 2020

Related U.S. Application Data

(60) Provisional application No. 62/467,157, filed on Mar. 5, 2017, provisional application No. 62/537,050, filed on Jul. 26, 2017.

(51) Int. Cl.
| | | |
|---|---|---|
| A61K 31/353 | (2006.01) | |
| A61K 31/05 | (2006.01) | |
| A61K 31/015 | (2006.01) | |
| A61K 31/01 | (2006.01) | |
| A61K 31/194 | (2006.01) | |
| A61K 31/045 | (2006.01) | |
| A61K 31/12 | (2006.01) | |
| A61P 1/00 | (2006.01) | |
| A61P 29/00 | (2006.01) | |
| A61K 31/352 | (2006.01) | |
| A61K 36/185 | (2006.01) | |
| A61K 45/06 | (2006.01) | |

(52) U.S. Cl.
CPC ............ *A61K 31/353* (2013.01); *A61K 31/01* (2013.01); *A61K 31/015* (2013.01); *A61K 31/045* (2013.01); *A61K 31/05* (2013.01); *A61K 31/12* (2013.01); *A61K 31/194* (2013.01); *A61K 31/352* (2013.01); *A61K 36/185* (2013.01); *A61P 1/00* (2018.01); *A61P 29/00* (2018.01); *A61K 45/06* (2013.01)

(58) Field of Classification Search
CPC .... A61K 31/353; A61K 31/01; A61K 31/015; A61K 31/045; A61K 31/05; A61K 31/12
See application file for complete search history.

(56) References Cited

U.S. PATENT DOCUMENTS

| | | | |
|---|---|---|---|
| 6,410,588 B1 | 6/2002 | Feldmann et al. | |
| 6,949,582 B1 | 9/2005 | Wallace | |
| 8,980,942 B2 | 3/2015 | Stinchcomb et al. | |
| 9,044,390 B1 | 6/2015 | Speier | |
| 9,730,911 B2 | 8/2017 | Verzura et al. | |
| 2002/0132021 A1 | 9/2002 | Raskin et al. | |
| 2004/0175367 A1 | 9/2004 | Herlyn et al. | |
| 2007/0032544 A1 | 2/2007 | Korthout et al. | |
| 2009/0197941 A1 | 8/2009 | Guy et al. | |
| 2010/0047853 A1 | 2/2010 | Kuo et al. | |

(Continued)

FOREIGN PATENT DOCUMENTS

| | | |
|---|---|---|
| EP | 2298283 | 3/2011 |
| GB | 2393721 | 4/2004 |

(Continued)

OTHER PUBLICATIONS

MedicineNet ("Cancer" at http://www.medterms.com (Year: 2011).*
Office Action dated Nov. 10, 2020 From the Israel Patent Office Re. Application No. 261847 and Its Translation Into English. (5 Pages).
Restriction Official Action dated Oct. 30, 2020 From the US Patent and Trademark Office Re. U.S. Appl. No. 16/491,197. (8 Pages).
International Preliminary Report on Patentability dated Nov. 9, 2017 From the International Bureau of WIPO Re. Application No. PCT/IL2016/050348. (8 Pages) Correction.
International Preliminary Report on Patentability dated Oct. 12, 2017 From the International Bureau of WIPO Re. Application No. PCT/IL201 6/050348. (8 Pages).
International Preliminary Report on Patentability dated Sep. 27, 2018 From the International Bureau of WIPO Re. Application No. PCT/IL2017/050338. (7 Pages).

(Continued)

*Primary Examiner* — Dennis Heyer

(57) ABSTRACT

A method of treating a malignant disease in a subject in need thereof is provided. The method comprising administering to the subject a therapeutically effective amount of a first liquid chromatography fraction of a cannabis extract comprising at least 75% tetrahydrocannabinolic acid (THCA), and a therapeutically effective amount of a second liquid chromatography fraction of a cannabis extract comprising at least 75% cannabigerolic acid (CBGA), wherein the first liquid chromatography fraction comprises cannabis derived active ingredients other than the THCA, and the second liquid chromatography fraction comprises cannabis derived active ingredients other than the CBGA, thereby treating the malignant disease in the subject.

20 Claims, 22 Drawing Sheets
(7 of 22 Drawing Sheet(s) Filed in Color)

(56) References Cited

U.S. PATENT DOCUMENTS

| | | |
|---|---|---|
| 2010/0249223 A1 | 9/2010 | Di Marzo et al. |
| 2010/0286098 A1 | 11/2010 | Robson et al. |
| 2012/0128777 A1 | 5/2012 | Keck et al. |
| 2013/0059018 A1 | 3/2013 | Parolaro et al. |
| 2013/0122114 A1 | 5/2013 | Golan et al. |
| 2013/0224151 A1 | 8/2013 | Pearson et al. |
| 2014/0221469 A1 | 8/2014 | Ross et al. |
| 2015/0086653 A1* | 3/2015 | Parolaro .............. A61K 31/015 424/725 |
| 2015/0297654 A1 | 10/2015 | Speier |
| 2016/0106705 A1 | 4/2016 | Verzura et al. |
| 2017/0007540 A1 | 1/2017 | Gupta |
| 2018/0092954 A1 | 4/2018 | Koltai et al. |
| 2019/0100731 A1 | 4/2019 | Koltai et al. |
| 2020/0222359 A1 | 7/2020 | Koltai et al. |

FOREIGN PATENT DOCUMENTS

| | | |
|---|---|---|
| GB | 2527590 | 12/2015 |
| WO | WO 03/061563 | 7/2003 |
| WO | WO 2009/004302 | 1/2009 |
| WO | WO 2011/051947 | 5/2011 |
| WO | WO 2014/159688 | 10/2014 |
| WO | WO 2016/103254 | 6/2016 |
| WO | WO 2016/157192 | 10/2016 |
| WO | WO 2016/179581 | 11/2016 |
| WO | WO 2016/189525 | 12/2016 |
| WO | WO 2017/013661 | 1/2017 |
| WO | WO 2017/158609 | 9/2017 |
| WO | WO 2018/163163 | 9/2018 |
| WO | WO 2018/163164 | 9/2018 |

OTHER PUBLICATIONS

International Search Report and the Written Opinion dated Jul. 7, 2016 From the International Searching Authority Re. Application No. PCT/IL2016/050348.

International Search Report and the Written Opinion dated Jun. 7, 2018 From the International Searching Authority Re. Application No. PCT/ IL2018/050248. (17 Pages).

International Search Report and the Written Opinion dated Jun. 17, 2018 From the International Searching Authority Re. Application No. PCT/IL2018/050249. (15 Pages).

International Search Report and the Written Opinion dated Jun. 26, 2017 From the International Searching Authority Re. Application No. PCT/IL2017/050338. (10 Pages).

Office Action dated Jun. 13, 2019 From the Israel Patent Office Re. Application No. 61847 and Its Translation Into English. (5 Pages).

Supplementary European Search Report and the European Search Opinion dated Nov. 6, 2018 From the European Patent Office Re. Application No. 16771541.6. (8 Pages).

Supplementary European Search Report and the European Search Opinion dated Sep. 26, 2019 From the European Patent Office Re. Application No. 17765995.0. (12 Pages).

Aizpurua-Olaizola et al. "Evolution of the Cannabinoid and Terpene Content During the Growth of Cannabis sativa Plants From Different Chemotypes", Journal of Natural Products, 79(2): 324-331, Feb. 2, 2016.

Aviello et al. "Chemopreventive Effect of the Non-Psychotropic Phytocannabinoid Cannabidiol on Experimental Colon Cancer", Journal of Molecular Medicine, 90(8): 925-934, Published Online Jan. 10, 2012.

Ben-Shabat et al. "An Entourage Effect: Inactive Endogenous Fatty Acid Glycerol Esters Enhance 2-Arachidonoyl-Glycerol Cannabinoid Activity", European Journal of Pharmacology, 353(1): 23-31, Jul. 17, 1998.

Borrelli et al. "Colon Carcinogenesis Is Inhibited by the TRPM8 Antagonist Cannabigerol, A Cannabis-Derived Non-Psychotropic Cannabinoid", Carcinogenesis, 35(12): 2787-2797, Advance Access Publication Sep. 2014.

Colbert "Cannabinoid Profile: Tetrahydrocannabinolic Acid (THCa)", TheLeafOnline, 5 P., Jul. 15, 2014.

Danin "Erodium Crassifolium, Erodium Hirtum, Hoary-Leaved Heron's-Bill", Flowers of Israel, XP009506767, Retrieved From the Internet, p. 1-3, Aug. 8, 2014.

De Filippis et al. "Cannabidiol Reduces Intestinal Inflammation Through the Control of Neuroimmune Axis". PLoS ONE, 6(12): e28159-1-e28159-9, Dec. 6, 2011. Figs.5-8.

De Graaf et al. "Preparation and Incubation of Precision-Cut Liver and Intestinal Slices for Application in Drug Metabolism and Toxicity Studies", Nature Protocols, 5(9): 1540-1551, Published Online Aug. 19, 2010.

De Kanter et al. "Precision-Cut Organ Slices as a Tool to Study Toxicity and Metabolism of Xenobiotics With Special Reference to Non-Hepatic Tissues", Current Drug Metabolism, 3(1): 39-59, Feb. 2002.

D'Haens et al. "Future Directions in Inflammatory Bowel Disease Management", Journal of Crohn's and Colitis, 8(8): 726-734, Aug. 2014.

ElSohly et al. "Phytochemistry of Cannabis sativa L.", Progress in the Chemistry of Organic Natural Products: Phytocannabinoids. POGRCHEM, 103: 1-36, Published Online Jan. 25, 2017.

Evans et al. "The Development of a Method for the Preparation of Rat Intestinal Epithelial Cell Primary Cultures", Journal of Cell Science, XP009006507, 101(1): 219-231, Jan. 31, 1992. Abstract, Figs.1, 2, Table 1, p. 222, Left Col., Para 5, p. 228, Left Col., 1st Para.

Gohar et al. "Antibacterial Polyphenol From Erodium Glaucophyllum", Zeitung fuer Naturforschung, 58(9-10): 670-674, Sep.-Oct. 2003. p. 670, 672-673.

Greenhough et al. "The Cannabinoid [Delta]9-Tetrahydrocannabinol Inhibits RAS-MAPK and PI3K-AKT Survival Signalling and Induces BAD-Mediated Apoptosis in Colorectal Cancer Cells", International Journal of Cancer, 121(10): 2172-2180, Published Online Jun. 21, 2007.

Greineisen et al. "Immunoactive Effects of Cannabinoids: Considerations for the Therapeutic Use of Cannabinoid Receptor Agonists and Antagonists", International Immunopharmacology, 10(5): 547-555, May 2010.

Harvey et al. "Interleukin 17A Evoked Mucosal Damage Is Attenuated by Cannabidiol and Anandamide in a Human Colonic Explant Model", Cytokine, XP055602795, 65(2): 236-244, Available Online Nov. 13, 2013.

Hill et al. "Cannabidivarin-Rich Cannabis Extracts Are Anticonvulsant in Mouse and Rat via a CB1 Receptor-Independent Mechanism", British Journal of Pharmacology, 170(3): 679-692, Oct. 2013.

Ihenetu et al. "Inhibition of Interleukin-8 Release in the Human Colonic Epithelial Cell Line HT-29 by Cannabinoids", European Journal of Pharmacology, 458(1-2): 207-215, Jan. 2003.

Izzo et al. "Cannabinoids Is an Intestinal Inflammation and Cancer", Pharmacological Research, 60(2): 117-125, Aug. 2009.

Javid et al. "Cannabinoid Pharmacology in Cancer Research: A New Hope for Cancer Patients?", European Journal of Pharmacology, 775: 1-4, Mar. 15, 2016.

Kauffman et al. "Alternative Functional In Vitro Models of Human Intestinal Epithelia", Frontiers in Pharmacology, XP055503086, 4(Art.79): 1-18, Published Online Jul. 8, 2013.

MatTek Corporation "EpiIntestinal™", Overiew, MatTek Corporation, 8 P., 2017.

Mechoulam et al. "Cannabidiol: An Overview of Some Pharmacological Aspects", The Journal of Clinical Pharmacology, 42(S1): 11S-19S, Nov. 2002.

Mechoulam et al. "Chemical Basis of Hashish Activity", Science, 169(3945): 611-612, Aug. 7, 1970.

Mechoulam et al. "Hashish—IV: The Isolation and Structure of Cannabinolic Cannabidiolic and Cannabigerolic Acids", Tetrahedron, 21(5): 1223-1229, Jan. 1965.

Naftali et al. "Cannabis Induces a Clinical Response in Patients With Crohn's Disease: A Prospective Placebo-Controlled Study", Clinical Gastroenterology and Hepatology, 11(10): 1276-1280, Oct. 2013.

(56) References Cited

OTHER PUBLICATIONS

Naftali et al. "Treatment of Crohn's Disease With Cannabis: An Observational Study", The Israel Medical Association Journal, IMAJ, 13(8): 455-458, Aug. 2011.
Pagano et al. "An Orally Active Cannabis Extract With High Content in Cannabidiol Attenuates Chemically-Induced Intestinal Inflammation and Hypermotility in the Mouse", Frontiers in Pharmacology, 7(Art.341): 1-12, Oct. 4, 2016.
Pageot et al. "Human Cell Models to Study Small Intestinal Functions: Recapitulation of the Crypt-Villus Axis", Microscopy Research and Technique, XP055622386, 49(4): 394-406, May 15, 2000.
Perera et al. "Immunomodulatory Activity of a Chinese Herbal Drug Yi Shen Juan Bi in Adjuvant Arthritis", Indian Journal of Pharmacology, XP055517710, 42(2): 65-69, Apr. 2010.
Romano et al. "Inhibition of Colon Carcinogenesis by a Standarized Cannabis Sativa Extract With High Content of Cannabidiol", Phytomedicine, 21(5): 631-639, Apr. 15, 2014.
Romano et al. "Pure [Delta]9-Tetrahydrocannabivarin and a *Cannabis sativa* Extract With High Content in [Delta]9-Tetrahydrocannabivarin Inhibit Nitrite Production in Murine Peritoneal Macrophages", Pharmacological Research, 113: 199-208, Available Online Aug. 3, 2016.
Russo et al. "Taming THC: Potential Cannabis Synergy and Phytocannabinoid-Terpenoid Entourage Effects", British Journal of Pharmacology, 163(7): 1344-1364, Aug. 2011.
Ryberg et al. "The Orphan Receptor GPR55 Is a Novel Cannabinoid Receptor", British Journal of Pharmacology, 152(7): 1092-1101, Published Online Sep. 17, 2007.
Sartor "Mechanisms of Disease: Pathogenesis of Crohn's Disease and Ulcerative Colitis", Nature Clinical Practice Gastroenterology & Hepatology, 3(7): 390-407, Jul. 2006.
Sato et al. "Long-Term Expansion of Epithelial Organoids From Human Colon, Adenoma, Adenocarcinoma, and Barrett's Epithelium", Gastroenterology, XP028325676, 141(5): 1762-1772, Published Online Jul. 27, 2011.
Schicho et al. "Cannabis Finds Its Way Into Treatment of Crohn's Disease", Pharmacology, 93(1-2): 1-3, Published Online Dec. 17, 2013.
Sroka et al. "Antioxidative Effect of Extracts From Erodium Cicutarium L.", Zeitung fuer Naturforschung, XP055319445, 49(11-12): 881-884, Nov.-Dec. 1994.
Stancic et al. "The GPR55 Antagonist CID16020046 Protects Against Intestinal Inflammation", Neurogastroenterology & Motility, 27(10): 1432-1445, Oct. 2015.
Storr et al. "Activation of the Cannabinoid 2 Receptor (CB2) Protects Against Experimental Colitis", Inflammation Bowel Disease, 15(11): 1678-1685, Published Online Apr. 30, 2009.
Sturm et al. "Epithelial Restitution and Wound Healing in Inflammatory Bowel Disease", World Journal of Gastroenterology, 14(3): 348-353, Jan. 21, 2008.
Wright et al. "Cannabinoid CB2 Receptors in the Gastrointestinal Tract: A Regulatory System in States of Inflammation", British Journal of Pharmacology, 153(2): 263-270, Published Online Oct. 1, 2007.
Official Action dated Apr. 16, 2021 from the US Patent and Trademark Office Re. U.S. Appl. No. 16/085,623. (37 pages).
Restriction Official Action dated Feb. 5, 2021 From the US Patent and Trademark Office Re. U.S. Appl. No. 16/085,623. (10 Pages).
Browning et al. "Organ Culture of Mucosal Biopsies of Human Small Intestine"; The Journal of Clinical Investigation, 48(8): 1423-1432, 1969.
Gracz et al. "Brief Report: CD24 and CD44 Mark Human Intestinal Epithelial Cell Populations with Characteristics of Active and Facultative Stem Cells"; Stem Cells Journals, 31: 2024-2030, 2013.
Merck KGaA "Millicell Inserts and Plates for Microporous Membrane-Based Cell Culture"; Fisher Scientific, 1-4 pages, 2014.
Reimund et al. "Mucosal Inflammatory Cytokine Production by Intestinal Biopsies in Patients with Ulcerative Colitis and Croh's Disease"; Journal of Clinical Immunology, 16(3): 144-150, 1996.
Official Action dated Jun. 3, 2021 from the US Patent and Trademark Office Re. U.S. Appl. No. 16/491,197. (35 pages).
Supplementary European Search Report and the European Search Opinion dated Dec. 2, 2020 From the European Patent Office Re. Application No. 18764952.0. (12 Pages).
Supplementary European Search Report and the European Search Opinion dated Nov. 26, 2020 From the European Patent Office Re. Application No. 18764840.7. (12 Pages).
Moreno-Sanz "Can You Pass the Acid Test? Critical Review and Novel Therapeutic Perspectives of Delta9-Tetrahydrocannabinolic Acid A", Cannabis and Cannabinoid Research, XP055633812, 1(1): 124-130, Published Online Jun. 1, 2016.
Naftali et al. "Cannabis for Inflammatory Bowel Disease", Digestive Diseases, XP009524112, 32(4): 468-474, Jun. 23, 2014.
Nallathambi et al. "Anti-Inflammatory Activity in Colon Models Is Derived From Delta9-Tetrahydrocannabinolic Acid That Interacts With Additional Compounds in Cannabis Extracts", Cannabis and Cannabinoid Research, XP055751236, 2(1): 167-182, Jul. 1, 2017.
Ruhaak et al. "Evaluation of the Cyclooxygenase Inhibiting Effects of Six Major Cannabinoids Isolated From Cannabis Saliva", Biological & Pharmaceutical Bulletin, XP055622634, 34(5): 774-778, Published Online Feb. 28, 2011.

\* cited by examiner

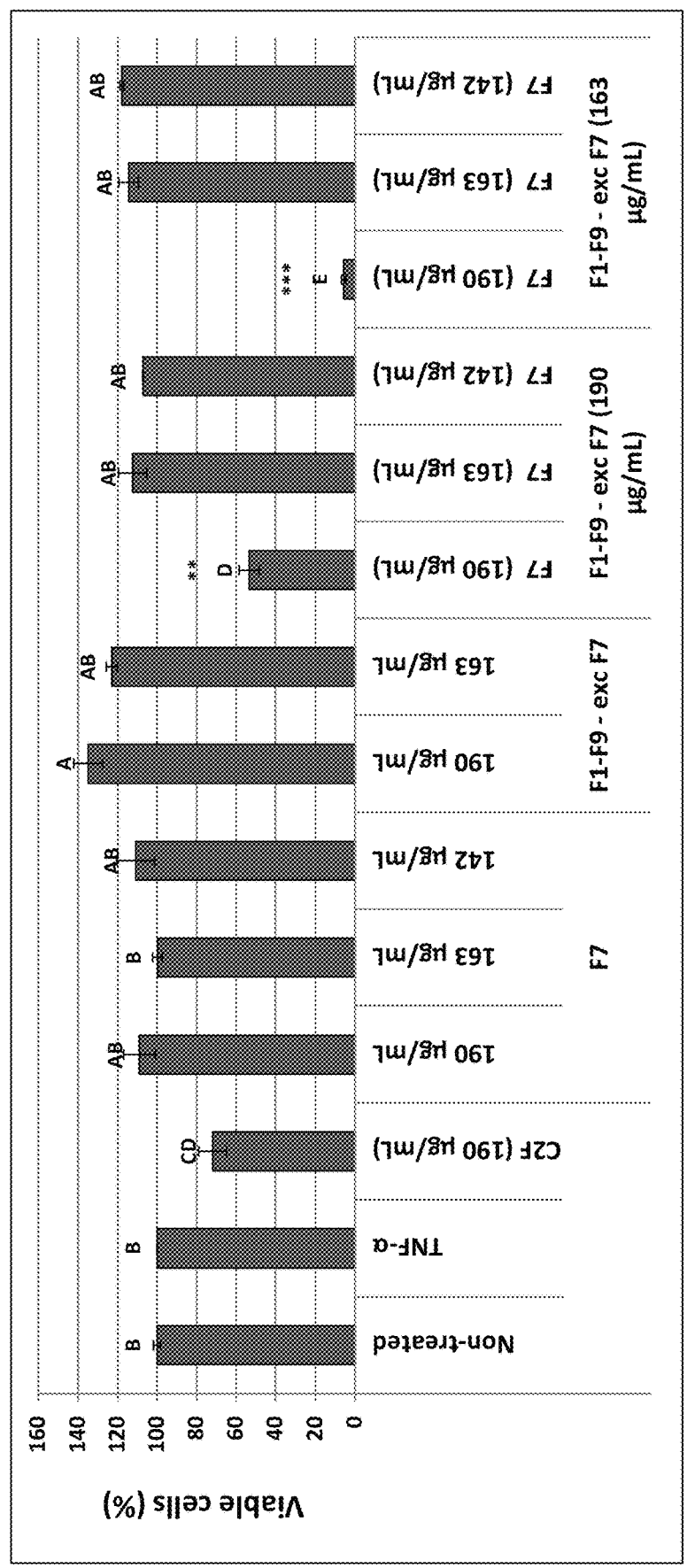

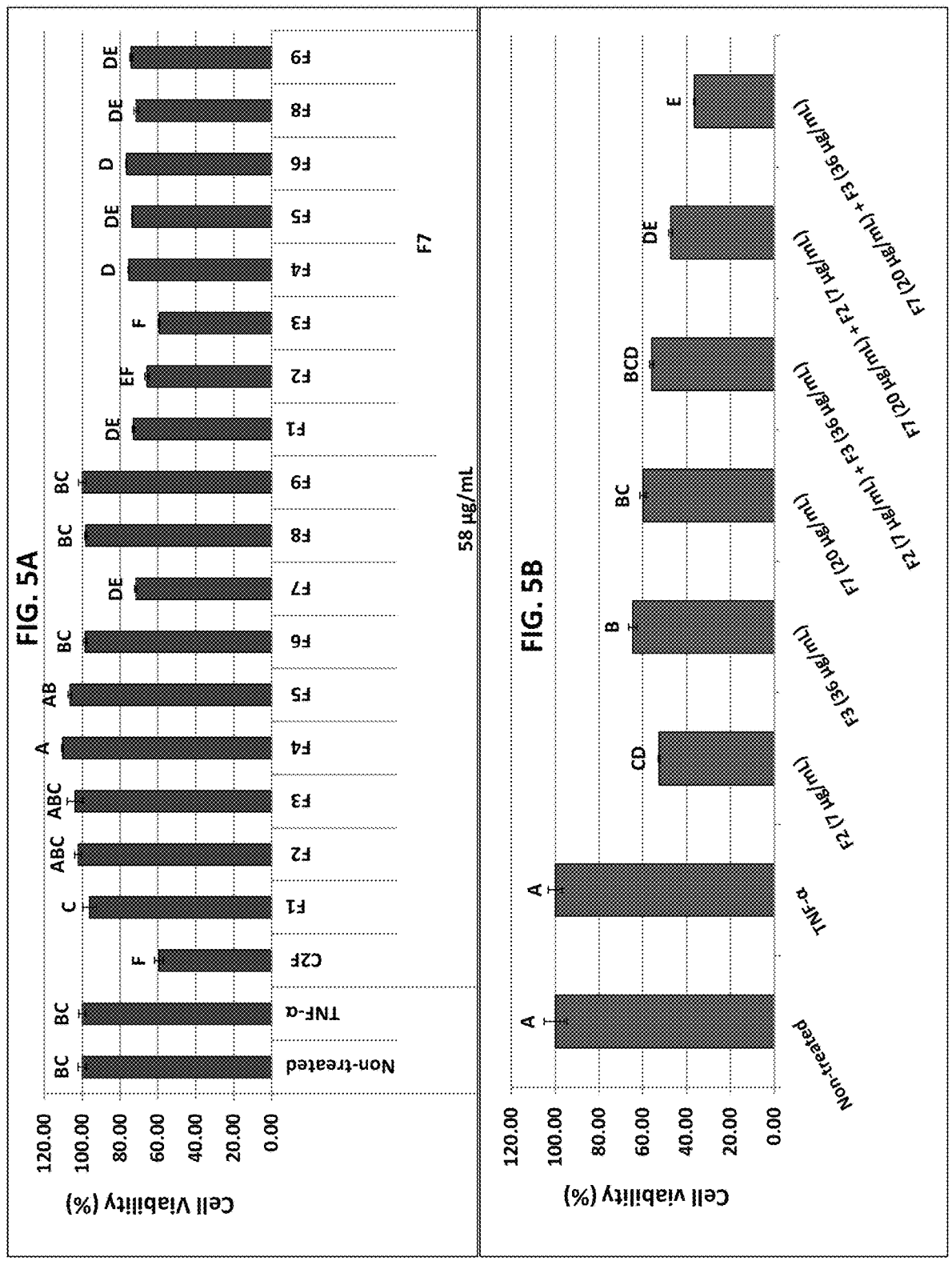

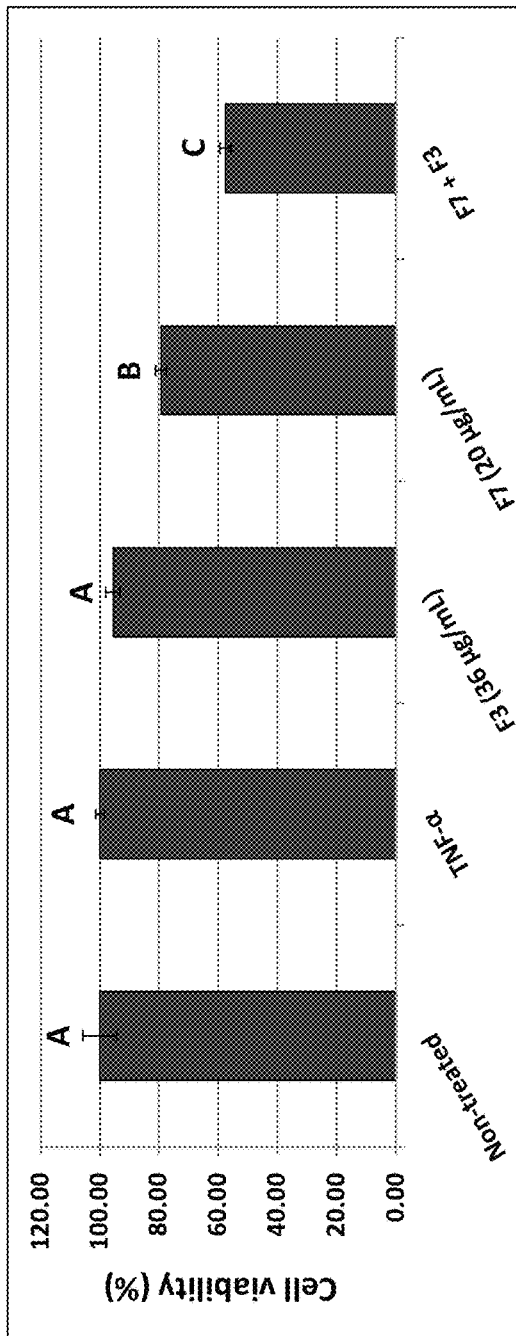
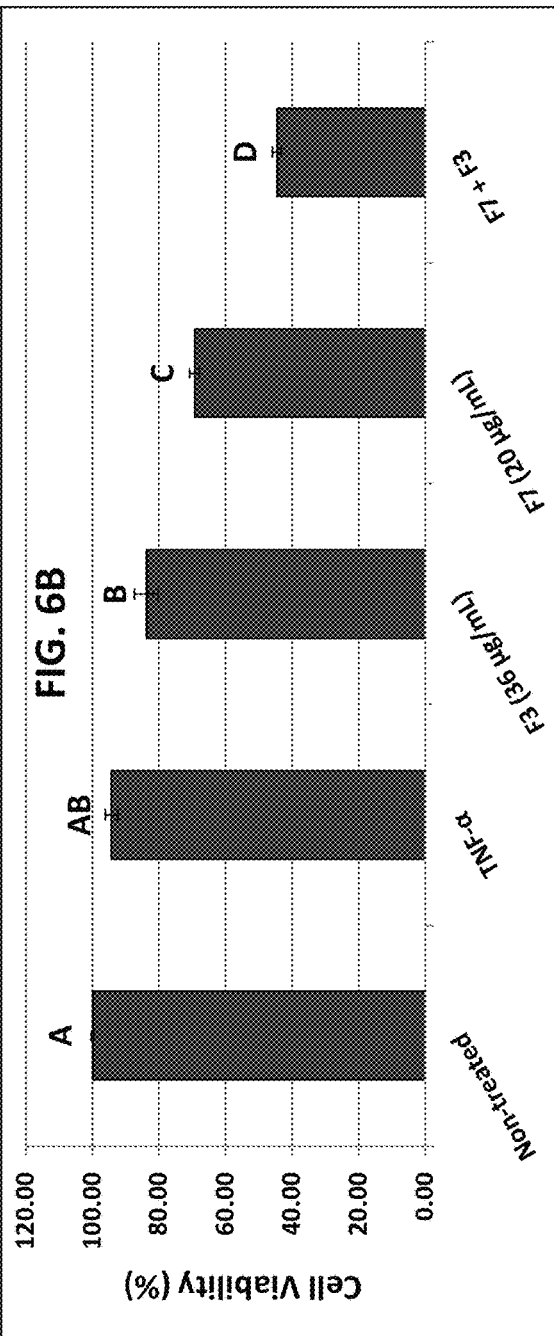

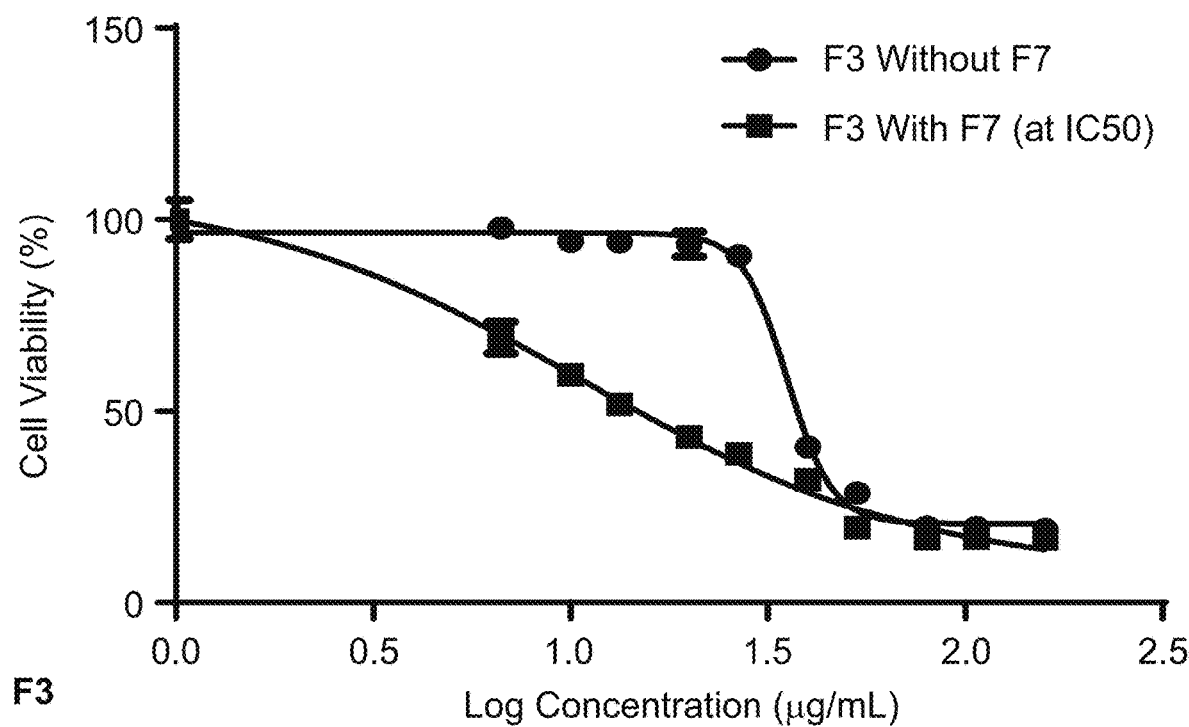
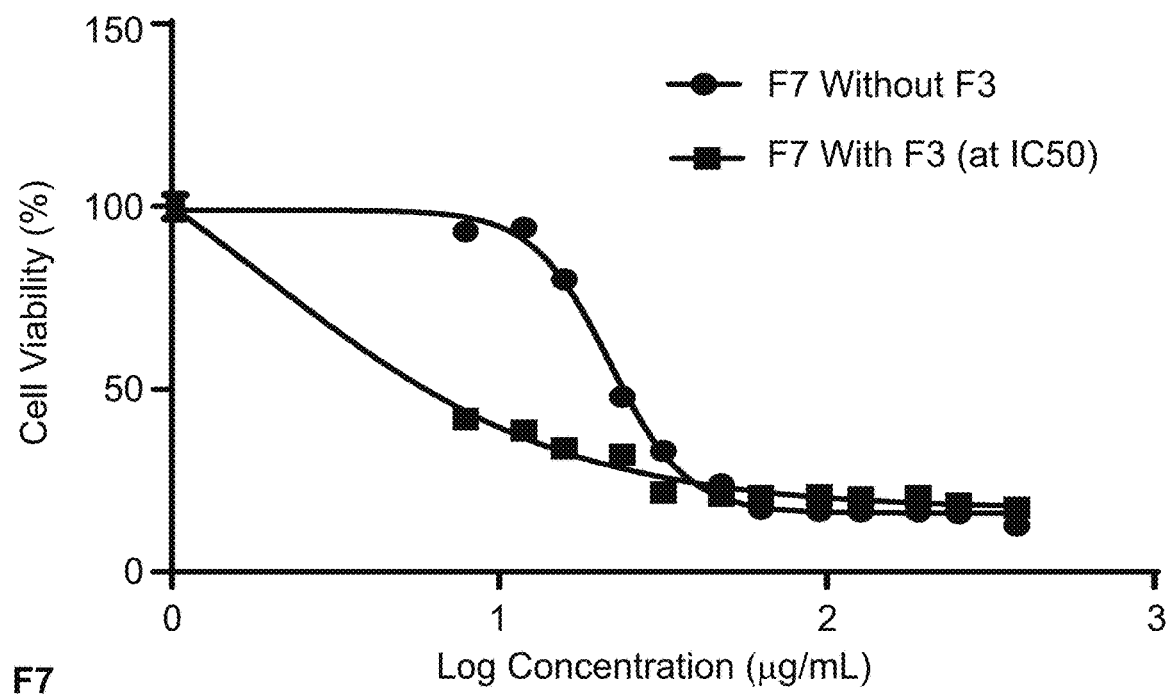

FIG. 7C

| | THCA 13.14 μg/ml | | | | | | |
|---|---|---|---|---|---|---|---|
| | CBGA 53.3 μg/ml | CBGA 40 μg/ml | CBGA 28 μg/ml | CBGA 20 μg/ml | CBGA 13.3 μg/ml | CBGA 6.67 μg/ml |
| Calculated value | 15.10 | 17.69 | 22.97 | 50.19 | 44.37 | 52.49 |
| Experimental value | 15.69 | 15.15 | 16.89 | 16.86 | 19.29 | 19.44 |

| | CBGA (28 μg/ml) | | | | | | |
|---|---|---|---|---|---|---|---|
| | THCA 50 μg/ml | THCA 30 μg/ml | THCA 25 μg/ml | THCA 15 μg/ml | THCA 12 μg/ml | THCA 6 μg/ml | THCA 4 μg/ml |
| Calculated value | 10.53 | 20.43 | 21.25 | 44.66 | 47.60 | 70.59 | 69.18 |
| Experimental value | 16.56 | 14.40 | 16.90 | 23.25 | 28.69 | 29.68 | 42.44 |

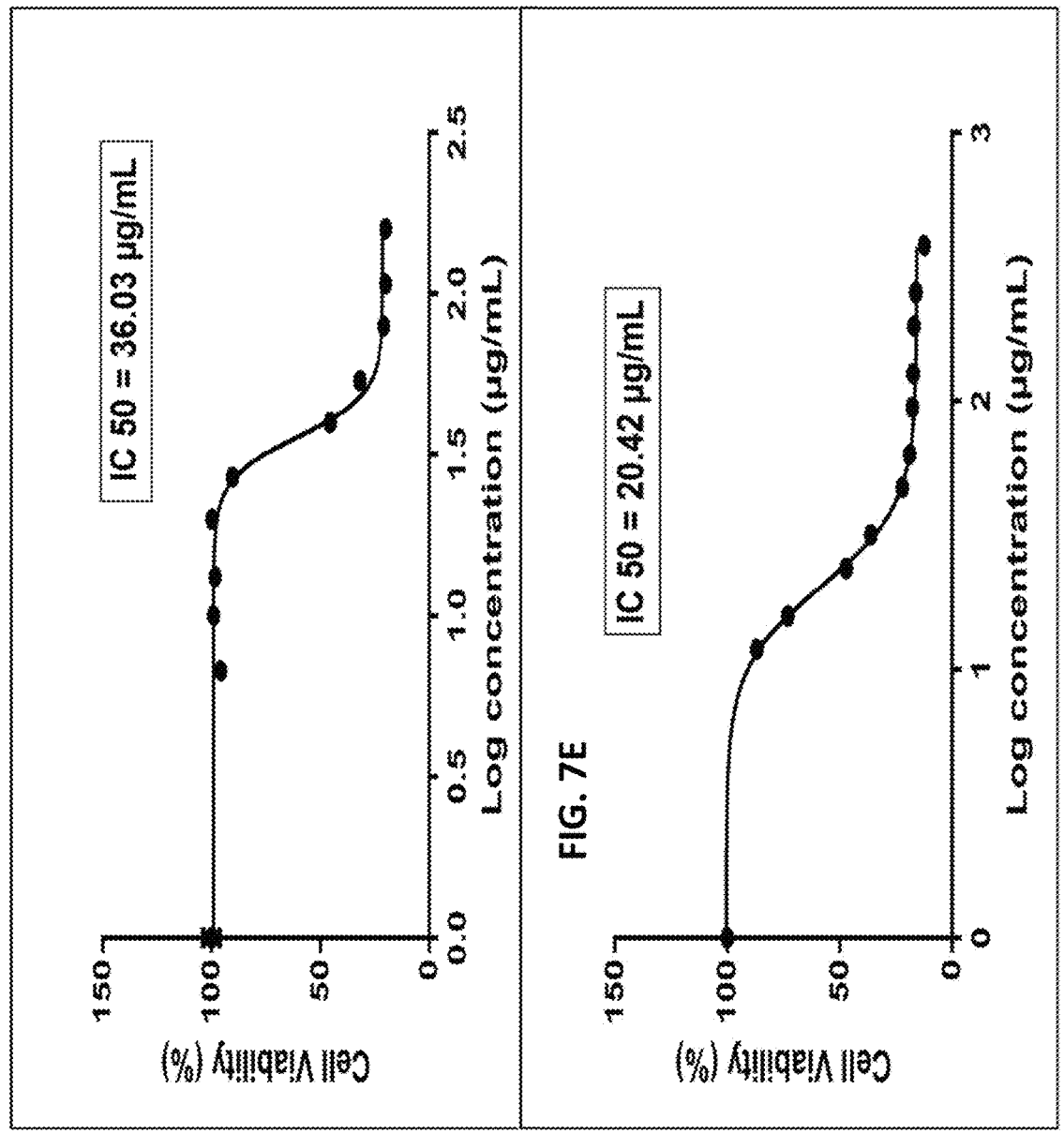

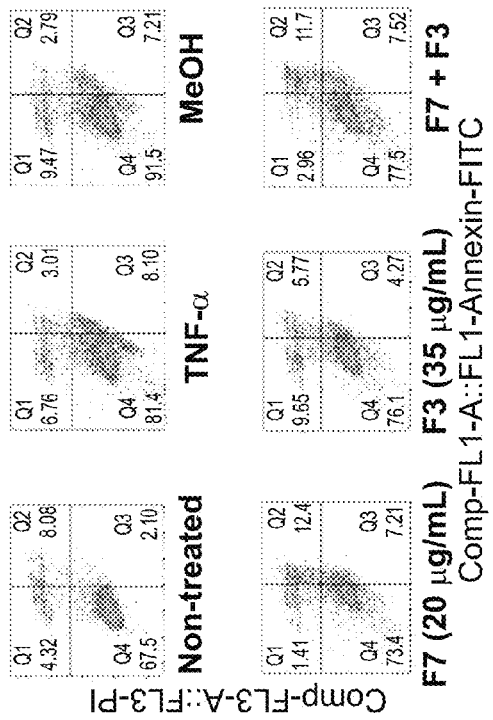
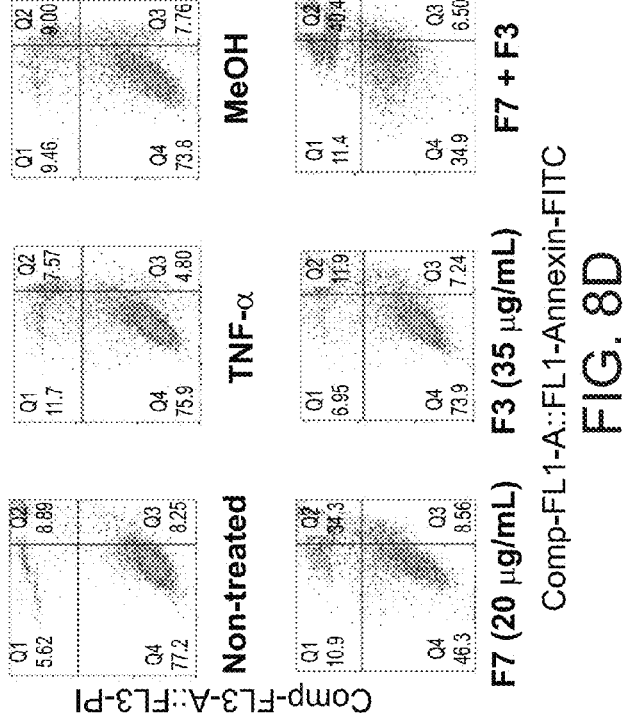
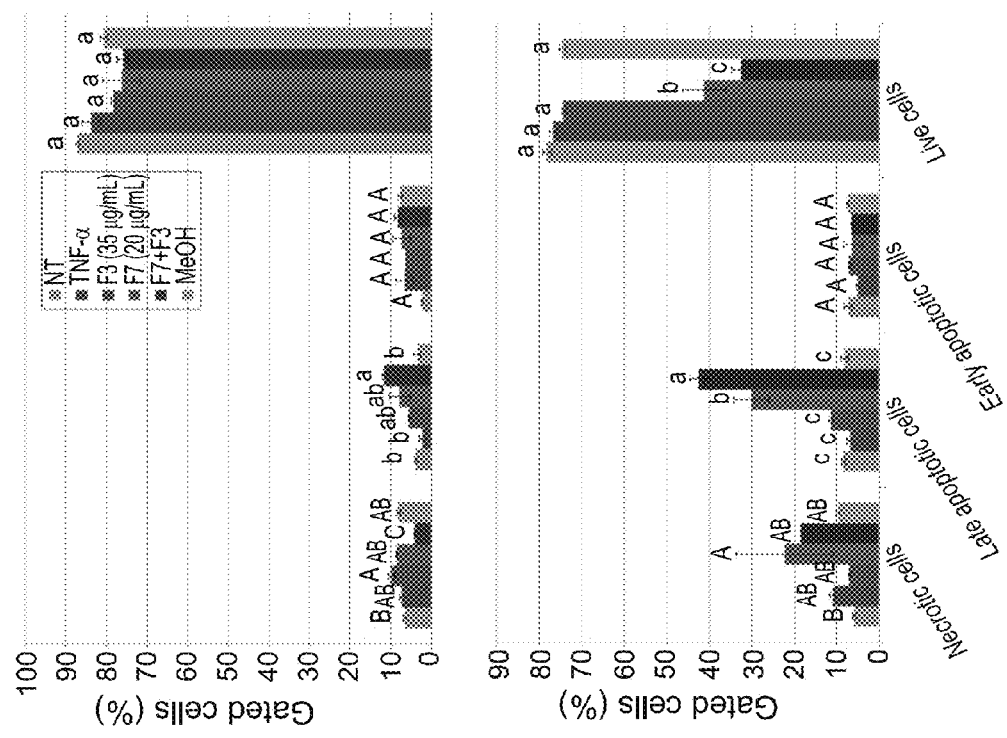
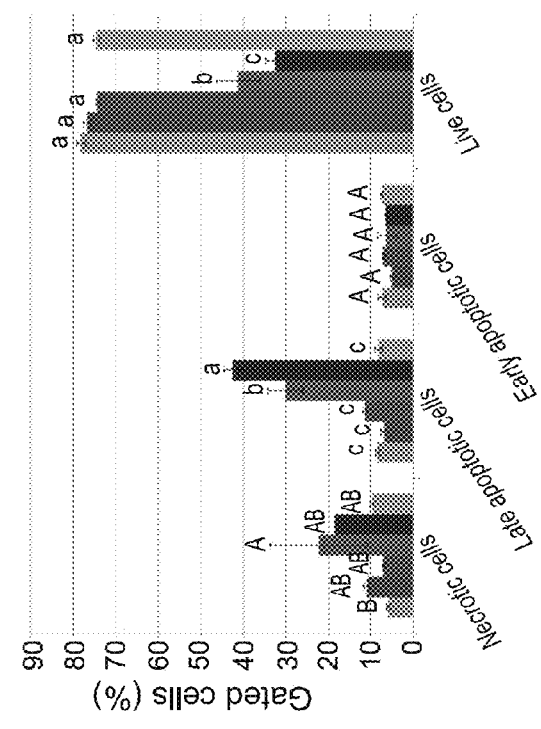

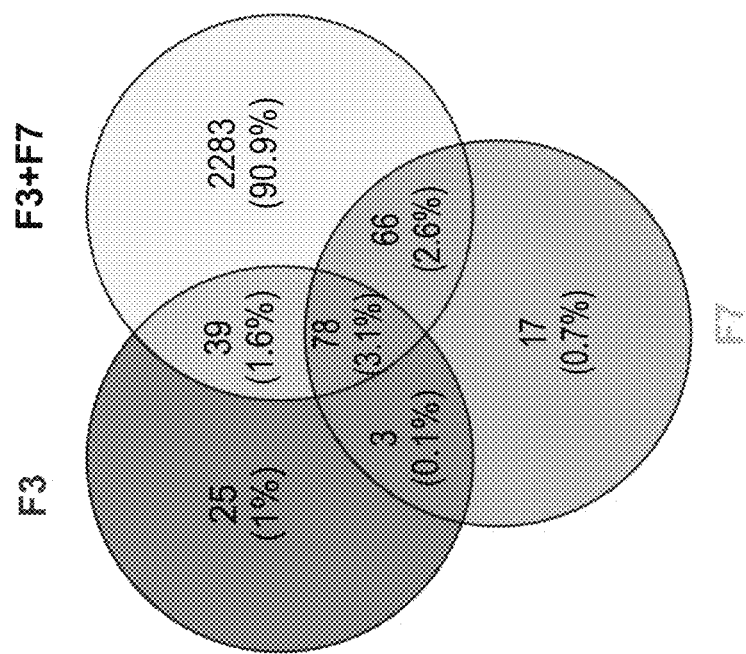
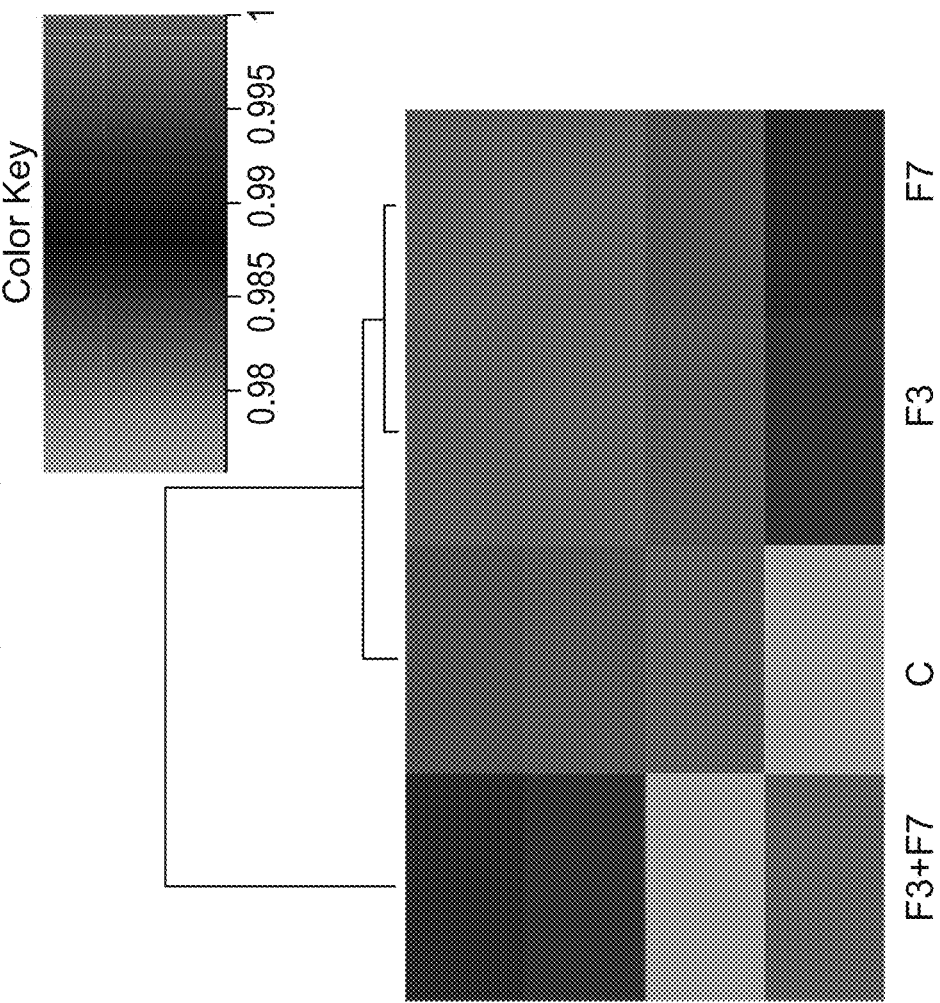
FIG. 10A
FIG. 10B

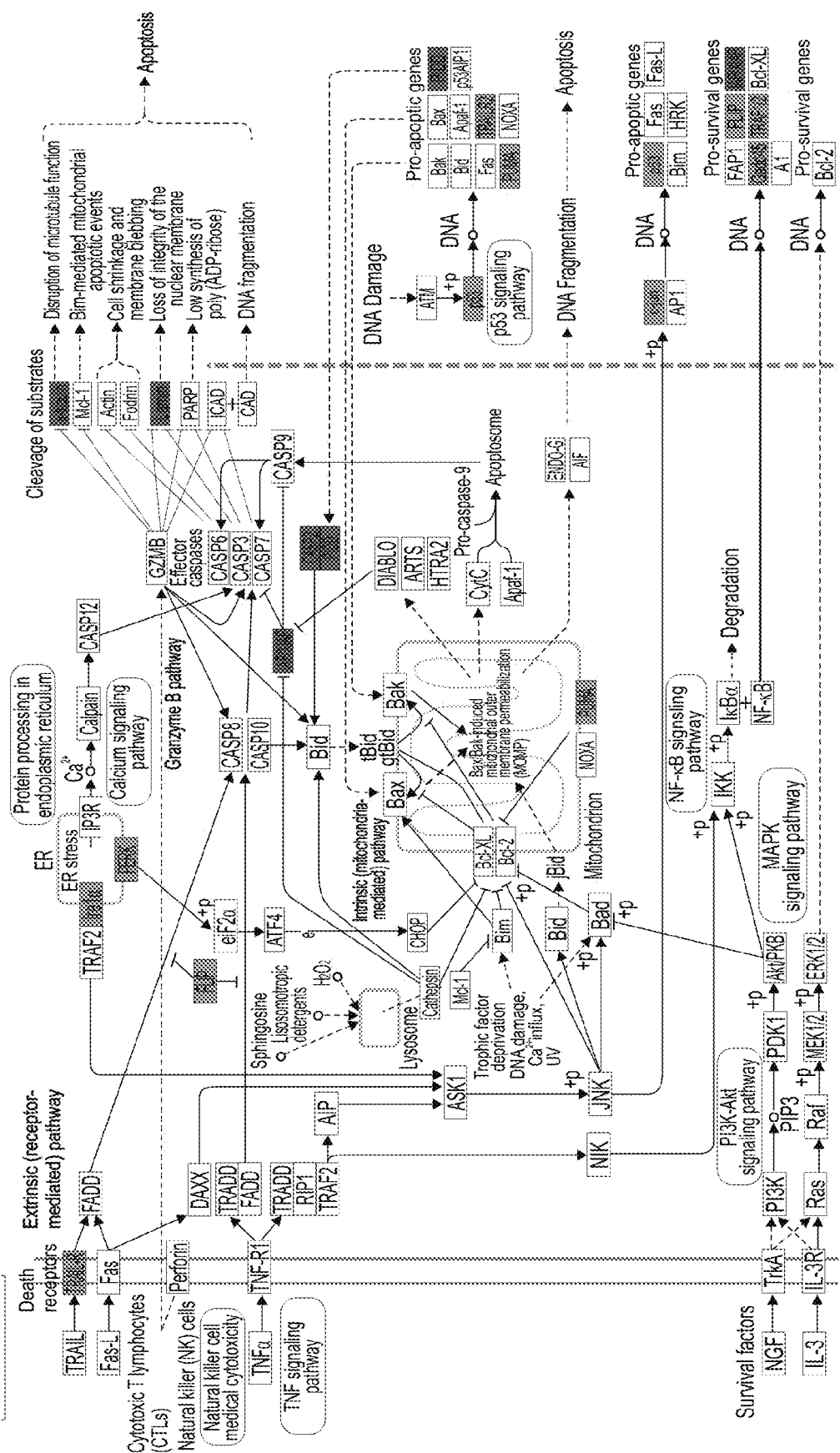

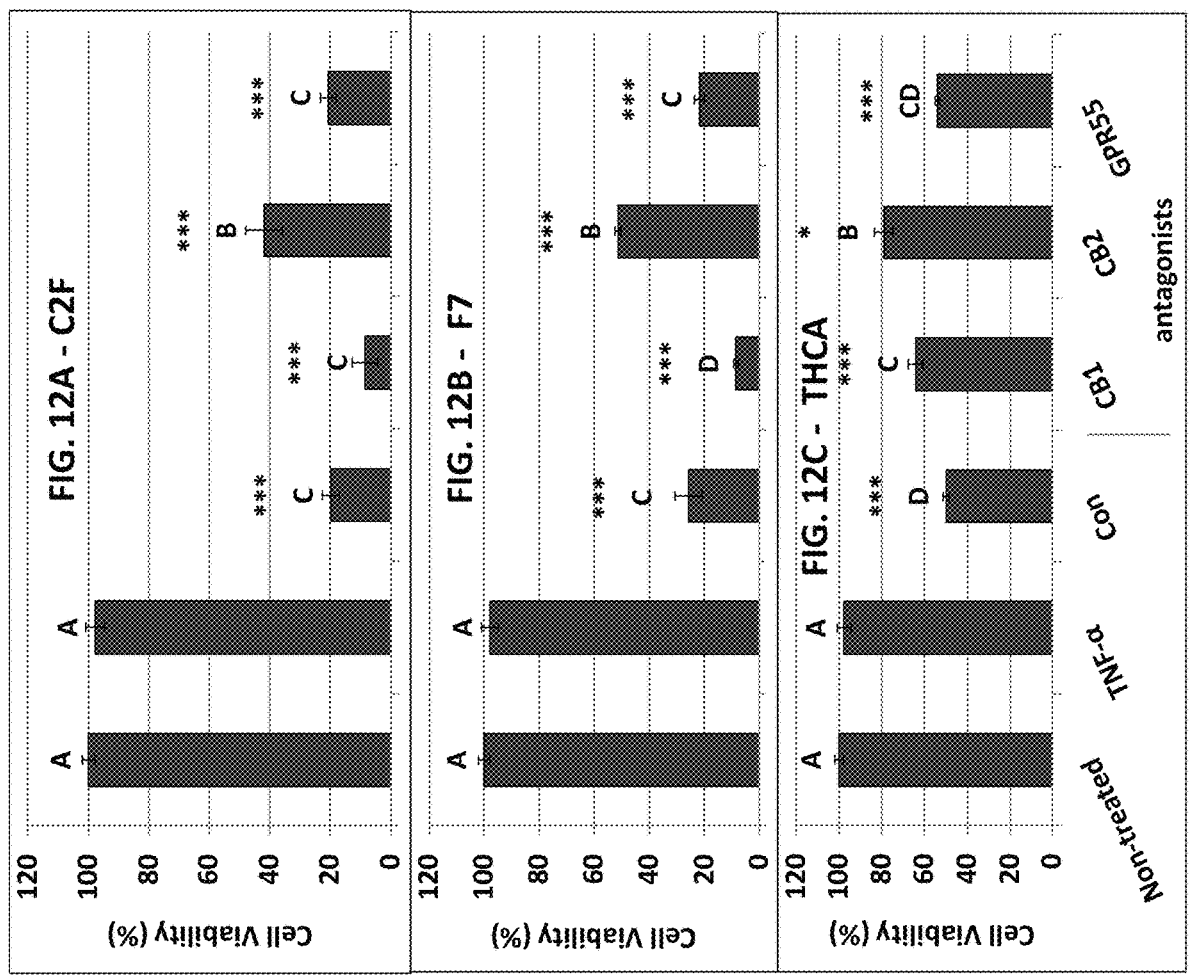

COMPOSITIONS AND METHODS FOR TREATING CANCER

FIELD AND BACKGROUND OF THE INVENTION

The present invention, in some embodiments thereof, relates to compositions and methods for the treatments of cancerous diseases.

Cancer is the second leading cause of human death next to coronary disease. Worldwide, millions of people die from cancer every year. While deaths from heart disease have been declining significantly, those resulting from cancer generally are on the rise. Despite billions of dollars spent in cancer research, complete and effective treatments have still not been developed. Part of the reason is that tumor cells are made up of a variety of cell types, produced as the cells proliferate and incur different mutations. Drug resistant cancer cells provide a strong selective advantage in comparison to other cells, and over time, those resistant cells increase in frequency. An effective cancer treatment would therefore benefit from attacking the cancer early, as well as attacking aggressively.

Although there has been some reduction in mortality caused by Colorectal cancer (CRC) due to advances in screening and preventive colonoscopy, it remains the third most common cancer diagnosis and fourth leading cause of cancer-related mortality worldwide. CRC is a heterogeneous disease that differs in clinical presentation, molecular characteristics, and prognosis. A series of histopathological and molecular changes lead the normal colonic epithelial cells to form aberrant crypt foci and polyps which can further transform into colorectal cancer, and adenomatous polyps are well established precursors of CRC. In addition to polypectomy, chemoprevention with natural or synthetic agents is another cornerstone in primary prevention. Because the natural history of CRC is protracted, clinical trials have concentrated on preventing adenomas, which represent a form of intraepithelial neoplasia and are the precursors to carcinoma.

Marijuana (*Cannabis sativa*) contains more than 500 constituents, among them more than a hundred terpenophenolic compounds termed phytocannabinoids [ElSohly et al., Phytochemistry of *Cannabis sativa* L. Phytocannabinoids, Springer (2017) 1-36]. An increasing number of studies have shown that phytocannabinoids can prevent proliferation, metastasis, angiogenesis and induce apoptosis in a variety of cancer cell types including breast, lung, prostate, skin, intestine, glioma, and others. This is due to their ability to regulate signaling pathways critical for cell growth and survival [David et al., European journal of pharmacology (2016) 775: 1-14]. Δ9-tetrahydrocannabinol (THC) treatment induced apoptosis in a CB1 dependent way in CRC cells and inhibited various survival signaling cascades while activating the pro-apoptotic BCL-2 family member BAD [Greenhough et al., International journal of cancer (2007) 121(10): 2172-2180]. Cannabidiol (CBD) reduced cell proliferation in colorectal carcinoma cell lines. In an animal model it reduced aberrant crypt foci (ACF, preneoplastic lesions), polyps, and tumor formation and counteracted colon cancer induced changes in gene expression [Aviello et al., Journal of molecular medicine (2012) 90(8): 925-934]. Also, a CBD-rich cannabis extract was shown to inhibit colorectal cancer cell proliferation and attenuate colon carcinogenesis. This activity involved both CB1 and CB2 receptor activation [Romano et al., Phytomedicine (2014) 21(5): 631-639]. Cannabigerol (CBG) promoted apoptosis, stimulated ROS production and reduced cell growth in CRC cells. In vivo, CBG inhibited the growth of chemically induced colon carcinogenesis and xenograft tumors [Borrelli et al., Carcinogenesis (2014) 35(12): 2787-2797]. Moreover, there seems to be an advantage of the unrefined content of the inflorescence versus an isolated compound [Russo, British journal of pharmacology (2011) 163(7): 1344-1364; Ben-Shabat et al., European journal of pharmacology (1998) 353(1): 23-31].

Additional background art includes:
U.S. Pat. Appls. 20160106705, 20100249223, 20130059018, 20140221469
www(dot)theleafonline(dot)com/c/science/2014/07/cannabinoid-profile-crash-course-thca/

SUMMARY OF THE INVENTION

According to an aspect of some embodiments of the present invention there is provided a method of treating a malignant disease in a subject in need thereof, the method comprising administering to the subject a therapeutically effective amount of a first liquid chromatography fraction of a cannabis extract comprising at least 75% tetrahydrocannabinolic acid (THCA), and a therapeutically effective amount of a second liquid chromatography fraction of a cannabis extract comprising at least 75% cannabigerolic acid (CBGA), wherein the first liquid chromatography fraction comprises cannabis derived active ingredients other than the THCA, and the second liquid chromatography fraction comprises cannabis derived active ingredients other than the CBGA, thereby treating the malignant disease in the subject.

According to an aspect of some embodiments of the present invention there is provided a method of treating a malignant disease in a subject in need thereof, the method comprising administering to the subject a therapeutically effective amount of a liquid chromatography fraction of a cannabis extract comprising at least 20% cannabichromene (CBC) and at least 20% tetrahydrocannabinolic acid (THCA), wherein the fraction comprises cannabis derived active ingredients other than the CBC and the THCA, thereby treating the malignant disease in the subject.

According to an aspect of some embodiments of the present invention there is provided a method of treating a malignant disease in a subject in need thereof, the method comprising administering to the subject a therapeutically effective amount of a first liquid chromatography fraction of a cannabis extract comprising at least 75% tetrahydrocannabinolic acid (THCA), and a therapeutically effective amount of a second liquid chromatography fraction of a cannabis extract comprising at least 20% cannabichromene (CBC) and at least 20% tetrahydrocannabinolic acid (THCA), wherein the first liquid chromatography fraction comprises cannabis derived active ingredients other than the THCA, and the second liquid chromatography fraction comprises cannabis derived active ingredients other than the CBC and the THCA, thereby treating the malignant disease in the subject.

According to an aspect of some embodiments of the present invention there is provided a therapeutically effective amount of a first liquid chromatography fraction of a cannabis extract comprising at least 75% tetrahydrocannabinolic acid (THCA), and a therapeutically effective amount of a second liquid chromatography fraction of a cannabis extract comprising at least 75% cannabigerolic acid (CBGA), wherein the first liquid chromatography fraction comprises cannabis derived active ingredients other than the THCA, and the second liquid chromatography fraction comprises cannabis derived active ingredients other than the CBGA, for use in treating a malignant disease in a subject in need thereof.

According to an aspect of some embodiments of the present invention there is provided a therapeutically effective amount of a liquid chromatography fraction of a cannabis extract comprising at least 20% cannabichromene (CBC) and at least 20% tetrahydrocannabinolic acid (THCA), wherein the fraction comprises cannabis derived active ingredients other than the CBC and the THCA, for use in treating a malignant disease in a subject in need thereof.

According to an aspect of some embodiments of the present invention there is provided a therapeutically effective amount of a first liquid chromatography fraction of a cannabis extract comprising at least 75% tetrahydrocannabinolic acid (THCA), and a therapeutically effective amount of a second liquid chromatography fraction of a cannabis extract comprising at least 20% cannabichromene (CBC) and at least 20% tetrahydrocannabinolic acid (THCA), wherein the first liquid chromatography fraction comprises cannabis derived active ingredients other than the THCA, and the second liquid chromatography fraction comprises cannabis derived active ingredients other than the CBC and the THCA, for use in treating a malignant disease in a subject in need thereof.

According to an aspect of some embodiments of the present invention there is provided a method of treating a malignant disease in a subject in need thereof, the method comprising administering to the subject a therapeutically effective amount of liquid chromatography pooled fractions of cannabis extract comprising active ingredients detectable by a detector operated at 220 nm, wherein the active ingredients comprise THCA and CBGA, thereby treating the malignant disease in the subject.

According to an aspect of some embodiments of the present invention there is provided a method of treating a malignant disease in a subject in need thereof, the method comprising administering to the subject a therapeutically effective amount of liquid chromatography pooled fractions of cannabis extract comprising active ingredients detectable by a detector operated at 220 nm, wherein the active ingredients comprise CBC and THCA, thereby treating the malignant disease in the subject.

According to an aspect of some embodiments of the present invention there is provided a therapeutically effective amount of liquid chromatography pooled fractions of cannabis extract comprising active ingredients detectable by a detector operated at 220 nm, wherein the active ingredients comprise THCA and CBGA, for use in treating a malignant disease in a subject in need thereof.

According to an aspect of some embodiments of the present invention there is provided a therapeutically effective amount of liquid chromatography pooled fractions of cannabis extract comprising active ingredients detectable by a detector operated at 220 nm, wherein the active ingredients comprise CBC and THCA, for use in treating a malignant disease in a subject in need thereof.

According to an aspect of some embodiments of the present invention there is provided a method of treating a malignant disease in a subject in need thereof, the method comprising administering to the subject a therapeutically effective amount of a composition comprising THCA and CBGA, wherein the composition is devoid of at least one of cannabichromene (CBC), cannabidiolic acid (CBDA), and/or cannabidiol (CBD), thereby treating the malignant disease in the subject.

According to an aspect of some embodiments of the present invention there is provided a method of treating a malignant disease in a subject in need thereof, the method comprising administering to the subject a therapeutically effective amount of a composition comprising CBC and THCA, wherein the composition is devoid of at least one of cannabidiolic acid (CBDA), cannabichromenic acid (CBCA), cannabigerolic acid (CBGA), thereby treating the malignant disease in the subject.

According to an aspect of some embodiments of the present invention there is provided a therapeutically effective amount of a composition comprising THCA and CBGA, wherein the composition is devoid of at least one of cannabichromene (CBC), cannabidiolic acid (CBDA), and/or cannabidiol (CBD), for use in treating a malignant disease in a subject in need thereof.

According to an aspect of some embodiments of the present invention there is provided a therapeutically effective amount of a composition comprising CBC and THCA, wherein the composition is devoid of at least one of cannabidiolic acid (CBDA), cannabichromenic acid (CBCA), cannabigerolic acid (CBGA), for use in treating a malignant disease in a subject in need thereof.

According to an aspect of some embodiments of the present invention there is provided a composition comprising liquid chromatography pooled fraction of a cannabis extract comprising active ingredients detectable by a detector operated at 220 nm, the active ingredients comprising CBGA.

According to an aspect of some embodiments of the present invention there is provided a composition comprising liquid chromatography pooled fractions of cannabis extract comprising active ingredients detectable by a detector operated at 220 nm, the active ingredients comprising CBC and THCA.

According to an aspect of some embodiments of the present invention there is provided a composition comprising liquid chromatography-purified cannabis extract obtainable by subjecting the cannabis extract to high pressure liquid chromatography (HPLC) and collecting fractions detectable by a detector operated at 220 nm, wherein the HPLC comprises a stationary phase comprising RP-18 end capped column, and a mobile phase of 15% solvent A (0.1% acetic acid in water) and 85% solvent B (methanol) at a flow rate of 1.5 mL/min for 9-12 minutes.

According to an aspect of some embodiments of the present invention there is provided a composition comprising liquid chromatography-purified cannabis extract obtainable by subjecting the cannabis extract to high pressure liquid chromatography (HPLC) and collecting fractions detectable by a detector operated at 220 nm, wherein conditions for the HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min for 9-12 minutes.

According to an aspect of some embodiments of the present invention there is provided a composition comprising liquid chromatography-purified cannabis extract obtainable by subjecting the cannabis extract to high pressure liquid chromatography (HPLC) and collecting fractions detectable by a detector operated at 220 nm, wherein the HPLC comprises a stationary phase comprising RP-18 end capped column, and a mobile phase of 15% solvent A (0.1% acetic acid in water) and 85% solvent B (methanol) at a flow rate of 1.5 mL/min for 5-9 minutes.

According to an aspect of some embodiments of the present invention there is provided a composition comprising liquid chromatography-purified cannabis extract obtainable by subjecting the cannabis extract to high pressure liquid chromatography (HPLC) and collecting fractions detectable by a detector operated at 220 nm, wherein conditions for the HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min for 5-9 minutes.

According to an aspect of some embodiments of the present invention there is provided a composition comprising liquid chromatography pooled fractions of cannabis extract comprising active ingredients detectable by a detector operated at 220 nm, the active ingredients comprising CBC and THCA, the composition being characterized by having a cytotoxic activity on cancer cells.

According to an aspect of some embodiments of the present invention there is provided a composition comprising THCA and CBGA, wherein the composition is devoid of at least one of cannabichromene (CBC), cannabidiolic acid (CBDA), and/or cannabidiol (CBD).

According to an aspect of some embodiments of the present invention there is provided a composition comprising CBC and THCA, wherein the composition is devoid of at least one of cannabidiolic acid (CBDA), cannabichromenic acid (CBCA), cannabigerolic acid (CBGA).

According to an aspect of some embodiments of the present invention there is provided a method of treating a malignant disease in a subject in need thereof, the method comprising administering to the subject a therapeutically effective amount of the composition of some embodiments of the invention, thereby treating the malignant disease in the subject.

According to an aspect of some embodiments of the present invention there is provided a therapeutically effective amount of the composition of some embodiments of the invention for use in treating a malignant disease in a subject in need thereof.

According to an aspect of some embodiments of the present invention there is provided a method of generating a cytotoxic composition, the method comprising: (i) adding a polar solvent to a dry cannabis inflorescence so as to obtain a crude extract; (ii) filtering the crude extract so as to obtain a filtered extract; (iii) fractionating the filtered extract on a high pressure liquid chromatography (HPLC); (iv) collecting the fractions detectable by a detector operated at 220 nm and comprising a component selected from the group consisting of (a) CBGA; and (b) CBC and THCA.

According to an aspect of some embodiments of the present invention there is provided a cytotoxic composition obtainable by the method of some embodiments of the invention.

According to an aspect of some embodiments of the present invention there is provided a method of treating a malignant disease in a subject in need thereof, the method comprising administering to the subject a therapeutically effective amount of the composition of some embodiments of the invention, thereby treating the malignant disease in the subject.

According to an aspect of some embodiments of the present invention there is provided a therapeutically effective amount of the composition of some embodiments of the invention for use in treating a malignant disease in a subject in need thereof.

According to an aspect of some embodiments of the present invention there is provided a method of determining a cytotoxic activity of the composition of some embodiments of the invention, the method comprising ex-vivo contacting a malignant tissue of a subject with the composition, wherein an increased cell death in cells of the malignant tissue above a predetermined threshold is indicative of the cytotoxic activity of the composition.

According to an aspect of some embodiments of the present invention there is provided a method of determining a cytotoxic activity of the composition of some embodiments of the invention, the method comprising ex-vivo contacting a malignant tissue of a subject with the composition, wherein a reduced cell proliferation in cells of the malignant tissue below a predetermined threshold is indicative of the cytotoxic activity of the composition.

According to some embodiments of the invention, the CBC to THCA ratio is 1:1.

According to some embodiments of the invention, the CBC to THCA ratio is higher than 1:1.

According to some embodiments of the invention, the composition comprises as an active ingredient CBGA.

According to some embodiments of the invention, the active ingredients in the composition comprise at least 75% CBGA.

According to some embodiments of the invention, the composition comprises as active ingredients CBC and THCA.

According to some embodiments of the invention, the CBC to THCA ratio is 1:1.

According to some embodiments of the invention, the CBC to THCA ratio is higher than 1:1.

According to some embodiments of the invention, the at least one of Aromadendrene, Epicedrol, alpha-Bisabolol, Lupeol, CBCA and/or CBN.

According to some embodiments of the invention, the composition comprises Aromadendrene, Epicedrol, alpha-Bisabolol, Lupeol, CBCA and CBN.

According to some embodiments of the invention, the composition comprises at least one of the components listed in Table 2.

According to some embodiments of the invention, the composition comprises at least one of Tumerone and/or Cystine.

According to some embodiments of the invention, the composition comprises Tumerone and Cystine.

According to some embodiments of the invention, the composition comprises as an active ingredient THCA.

According to some embodiments of the invention, the composition comprises at least one of D-Limonene, β-Caryophyllene, Humulene, malic acid, α-Farnesene, cannabinol (CBN), Δ9-tetrahydrocannabinol (THC), and/or cannabigerol (CBG).

According to some embodiments of the invention, the composition comprises D-Limonene, β-Caryophyllene, Humulene, malic acid, α-Farnesene, cannabinol (CBN), Δ9-tetrahydrocannabinol (THC), and cannabigerol (CBG).

According to some embodiments of the invention, the composition comprises at least one of the components listed in Table 3.

According to some embodiments of the invention, the composition comprises is characterized by having a cytotoxic activity on cancer cells.

According to some embodiments of the invention, the THCA comprises a synthetic THCA or analog thereof having a cytotoxic activity.

According to some embodiments of the invention, the THCA comprises a liquid chromatography fraction of a cannabis extract, the fraction comprising at least 75% tetrahydrocannabinolic acid (THCA), wherein the fraction comprises cannabis derived active ingredients other than the THCA.

According to some embodiments of the invention, the cannabis extract comprises at least about 80-95% THCA.

According to some embodiments of the invention, the composition comprises at least one of D-Limonene, β-Caryophyllene, Humulene, malic acid, α-Farnesene, cannabinol (CBN), Δ9-tetrahydrocannabinol (THC), and/or cannabigerol (CBG).

According to some embodiments of the invention, the composition comprises at least two of the D-Limonene, β-Caryophyllene, Humulene, malic acid, α-Farnesene, cannabinol (CBN), Δ9-tetrahydrocannabinol (THC), and/or cannabigerol (CBG).

According to some embodiments of the invention, composition comprises components as listed in Table 3.

According to some embodiments of the invention, CBGA comprises a synthetic CBGA or analog thereof having a cytotoxic activity.

According to some embodiments of the invention, CBGA comprises a liquid chromatography fraction of a cannabis extract, the fraction comprising at least 75% cannabigerolic acid (CBGA), wherein the fraction comprises cannabis derived active ingredients other than the CBGA.

According to some embodiments of the invention, the cannabis extract comprises at least about 80-95% CBGA.

According to some embodiments of the invention, the composition comprises at least one of Aromadendrene, Epicedrol, alpha-Bisabolol, Lupeol, CBCA and/or CBN.

According to some embodiments of the invention, the composition comprises Aromadendrene, Epicedrol, alpha-Bisabolol, Lupeol, CBCA and CBN.

According to some embodiments of the invention, the composition comprises at least one of the components listed in Table 2.

According to some embodiments of the invention, the CBC comprises a synthetic CBC or analog thereof having a cytotoxic activity.

According to some embodiments of the invention, the CBC and the THCA comprise a liquid chromatography fraction of a cannabis extract, the fraction comprising at least 20% cannabichromene (CBC) and at least 20% tetrahydrocannabinolic acid (THCA), wherein the fraction comprises cannabis derived active ingredients other than the CBC and the THCA.

According to some embodiments of the invention, the cannabis extract comprises at least about 20-35% CBC.

According to some embodiments of the invention, the cannabis extract comprises at least about 20-35% THCA.

According to some embodiments of the invention, the composition comprise at least one of Tumerone and/or Cystine.

According to some embodiments of the invention, the composition comprises Tumerone and Cystine.

According to some embodiments of the invention, the extract is a fresh extract.

According to some embodiments of the invention, the extract is an ethanol extract.

According to some embodiments of the invention, the liquid chromatography comprises high pressure liquid chromatography (HPLC).

According to some embodiments of the invention, the liquid chromatography is performed on a reverse stationary phase.

According to some embodiments of the invention, the liquid chromatography is performed using a mobile phase comprising from 10 to 30% acidic aqueous solution and from 90 to 70% alcohol.

According to some embodiments of the invention, the HPLC comprises a stationary phase comprising RP-18 end capped column, and a mobile phase of 15% solvent A (0.1% acetic acid in water) and 85% solvent B (methanol) at a flow rate of 1.5 mL/min for 9-12 minutes.

According to some embodiments of the invention, the conditions for the HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min for 9-12 minutes.

According to some embodiments of the invention, the HPLC comprises a stationary phase comprising RP-18 end capped column, and a mobile phase of 15% solvent A (0.1% acetic acid in water) and 85% solvent B (methanol) at a flow rate of 1.5 mL/min for 5-9 minutes.

According to some embodiments of the invention, the conditions for the HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min for 5-9 minutes.

According to some embodiments of the invention, the HPLC comprises a stationary phase comprising RP-18 end capped column, and a mobile phase of 15% solvent A (0.1% acetic acid in water) and 85% solvent B (methanol) at a flow rate of 1.5 mL/min for 28-35 minutes.

According to some embodiments of the invention, the conditions for the HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min for 28-35 minutes.

According to some embodiments of the invention, the detector is a diode array detector.

According to some embodiments of the invention, the malignant disease is a solid tumor or a hematologic malignancy.

According to some embodiments of the invention, the solid tumor is selected from the group consisting of an intestinal cancer, a glioma, a breast cancer, a lung cancer, a prostate cancer, skin cancer, a renal cancer, an ovarian cancer, a head and neck cancer, a fibrosarcoma, a uterine cervix cancer, an esophagus cancer, a rectum cancer, an oral cavity cancer, a liver cancer and a pancreatic cancer.

According to some embodiments of the invention, the subject is a human subject.

According to some embodiments of the invention, the fractions comprise at least about 75% CBGA.

According to some embodiments of the invention, the fractions comprise at least one of Aromadendrene, Epicedrol, alpha-Bisabolol, Lupeol, CBCA and/or CBN.

According to some embodiments of the invention, the fractions comprise components as listed in Table 2.

According to some embodiments of the invention, the fractions comprise at least about 20% CBC.

According to some embodiments of the invention, the fractions comprise at least 20% THCA.

According to some embodiments of the invention, the fractions comprise at least one of Tumerone and/or Cystine.

According to some embodiments of the invention, the HPLC comprises a stationary phase comprising RP-18 end capped column, and a mobile phase of 15% solvent A (0.1% acetic acid in water) and 85% solvent B (methanol) at a flow rate of 1.5 mL/min for 9-12 minutes.

According to some embodiments of the invention, the conditions for the HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min for 9-12 minutes.

According to some embodiments of the invention, the HPLC comprises a stationary phase comprising RP-18 end capped column, and a mobile phase of 15% solvent A (0.1% acetic acid in water) and 85% solvent B (methanol) at a flow rate of 1.5 mL/min for 5-9 minutes.

According to some embodiments of the invention, the conditions for the HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min for 5-9 minutes.

According to some embodiments of the invention, the detector is a diode array detector.

According to some embodiments of the invention, the malignant tissue is a cancer tissue biopsy.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D depict the dose-effect curves of C. sativa ethanol extracts on viability of HCT116 colon cancer and CCD18 colon healthy cells. Dose-effect curves of C. sativa ethanol extracts of fresh inflorescences (C2F) (FIG. 1A; $IC_{50}=83.9$ μg/mL), heated inflorescences (C2B) (FIG. 1B; $IC_{50}=84.1$ μg/mL) on viability of HCT116 colon cancer cells and C2F (FIG. 1C; $IC_{50}=144.2$ μg/mL), C2B (FIG. 1D; $IC_{50}=54.6$ μg/mL) on viability of CCD18 colon healthy cells. Cell viability determined by Alamar Blue fluorescence (Resazurin assay). HCT116 and CCD18 cells were seeded (50,000 per well) in triplicate in 500 μL growing media and incubated for 24 hours at 37° C. in a humidified 5% $CO_2$-95% air atmosphere. Cells were treated with C2F, C2B at different dilutions along with 50 ng/mL TNF-α for 16 hours. Next, the cells were incubated with Alamar Blue for 4 hours. Relative fluorescence at the excitation/emission of 544/590 nm was measured. Values were calculated as percentage of live cells relative to the non-treated (cells without TNF-α and treatments) control after reducing the autofluorescence of Alamar Blue without cells (n=3). For dose response assays, data points were connected by non-linear regression lines of the sigmoidal dose-response relation. GraphPad Prism was employed to produce dose-response curve and $IC_{50}$ doses for C2F and C2B.

Figure 2A:
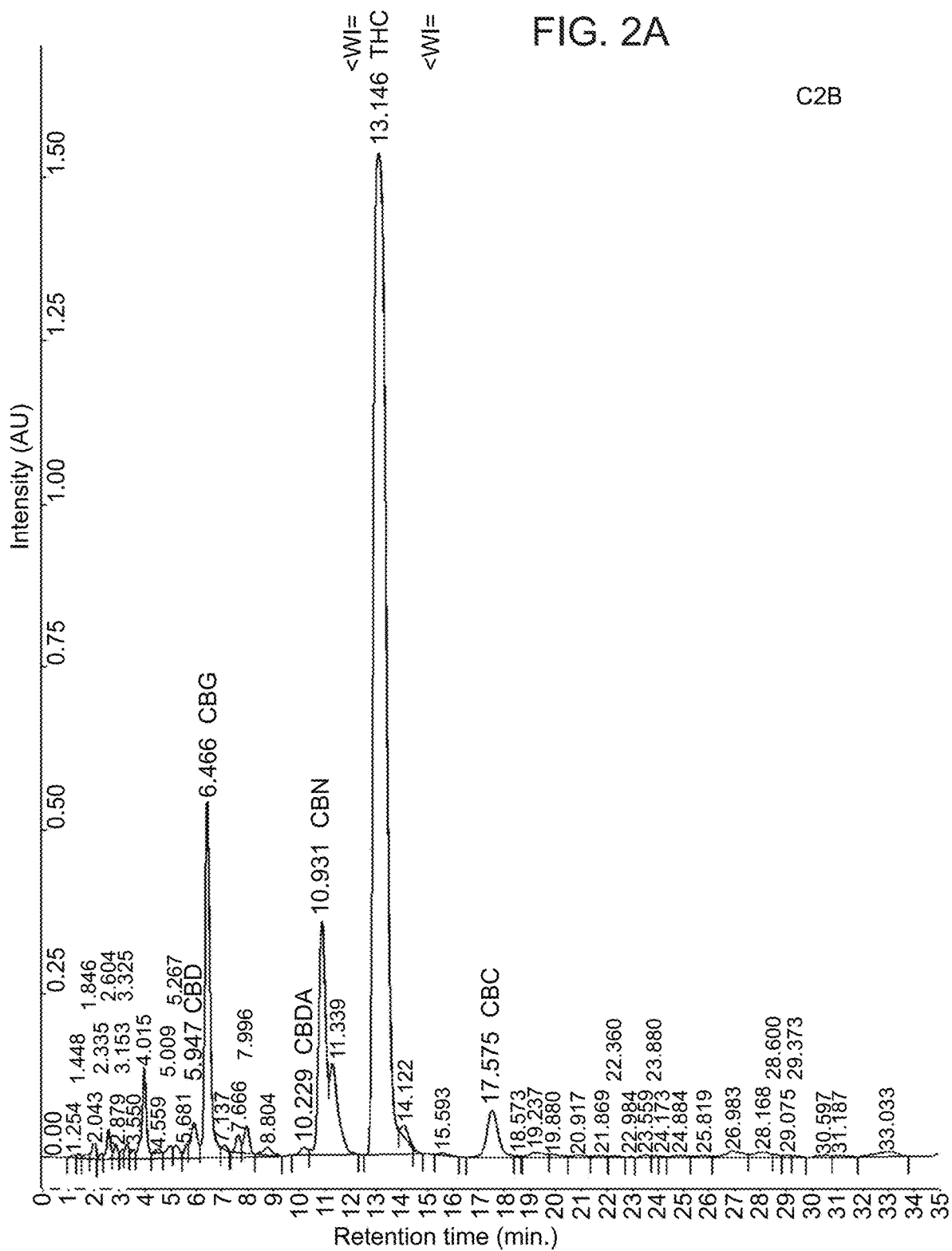
Figure 2B:
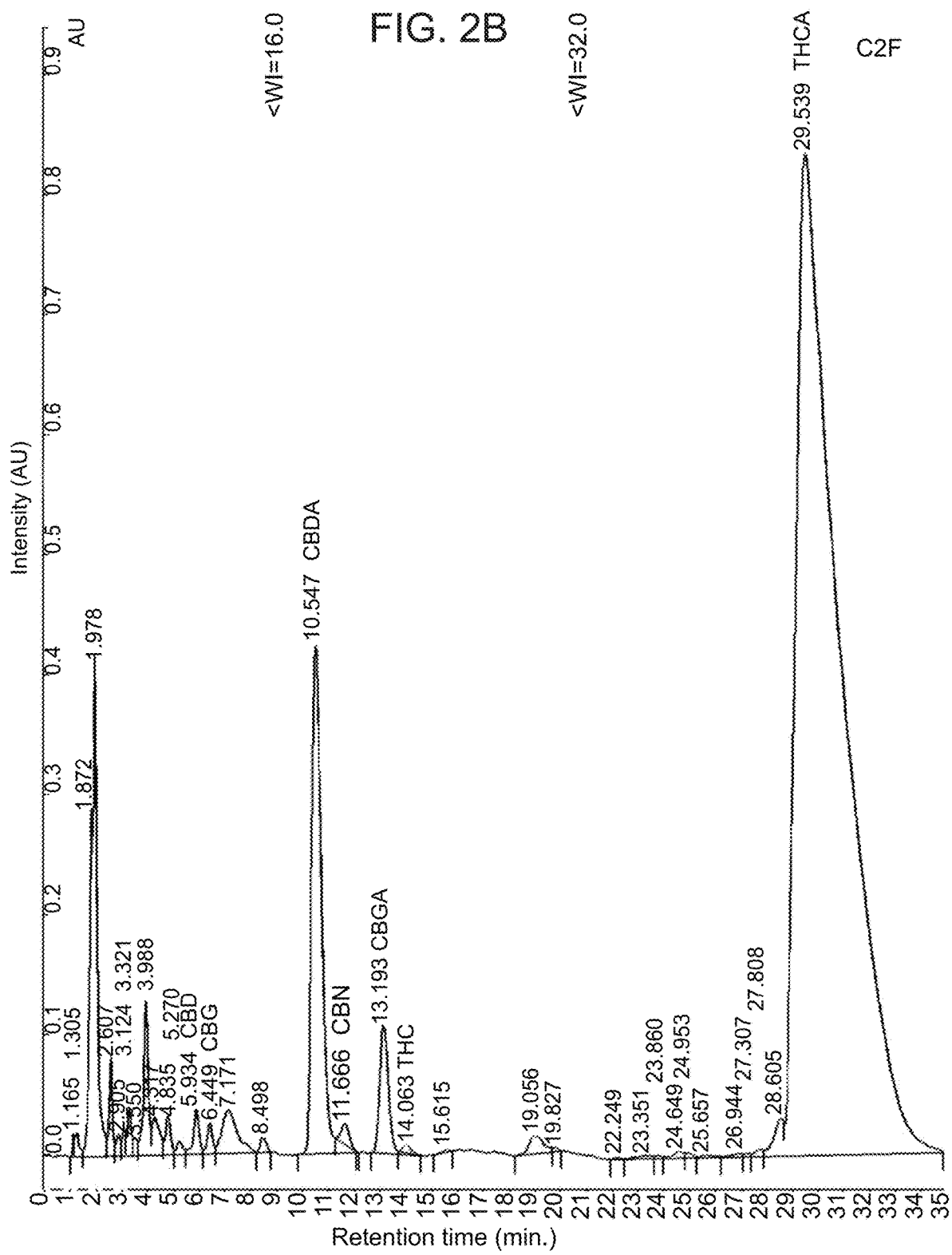

FIGS. 2A-B depict HPLC chromatograms of C. sativa ethanolic extracts. Chromatogram of fresh cannabis extract (FIG. 2B, C2F, 0.1 mg/mL) and baked (i.e., fresh flowers which were baked at 150° C. for 3 hours, FIG. 2A) cannabis extract (C2B, 0.1 mg/mL) obtained from isocratic elution with a mixture of 15% water containing 0.1% acetic acid (solvent A) and 85% MeOH (solvent B) for a total run time of 35 minutes at 220 nm. The samples were injected at a concentration of 0.58 mg/mL in a volume of 20 μL for C2B and 0.33 mg/mL in a volume of 20 μL for C2F.

Figure 3A:
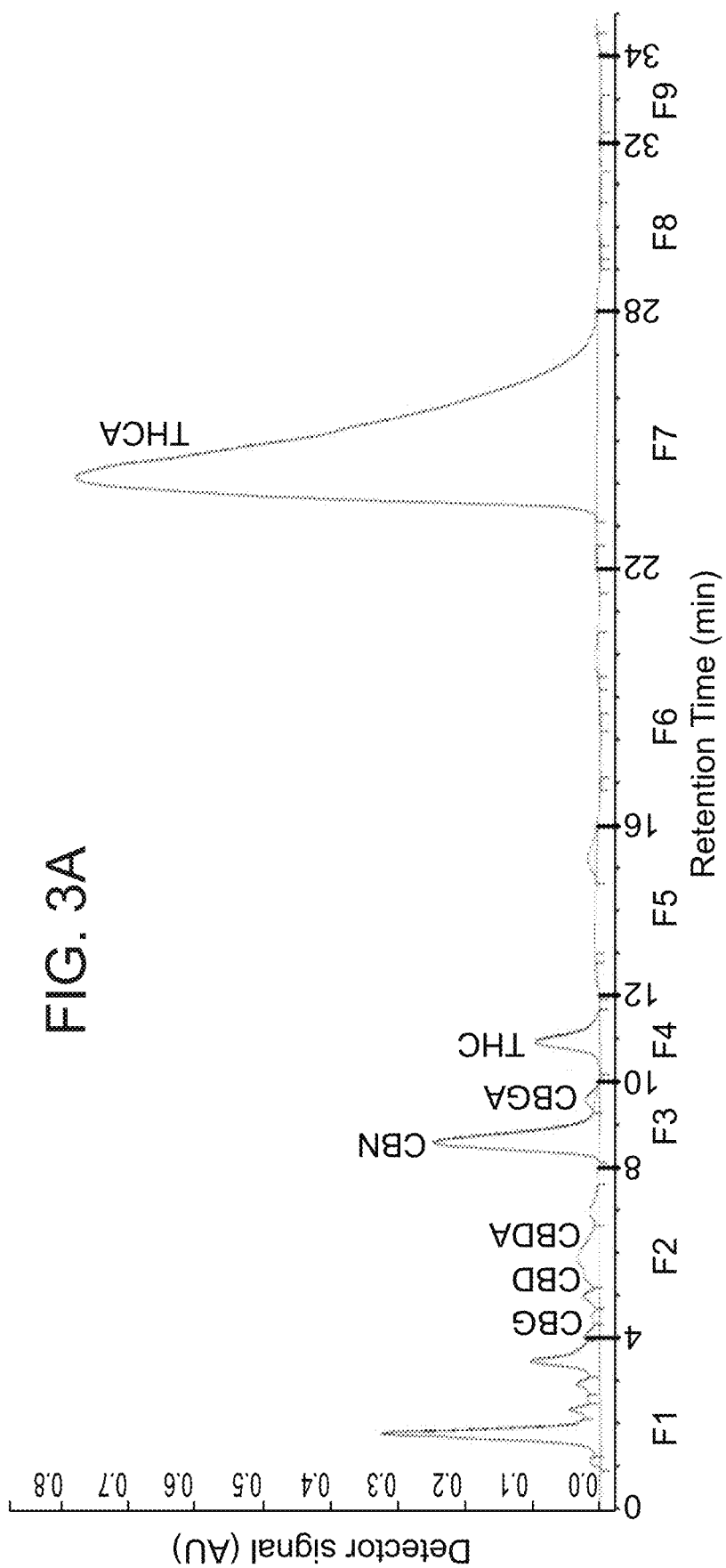

FIG. 3A depicts HPLC profile of fractions of C. sativa ethanolic extract. HPLC profile was obtained from isocratic elution with a mixture of 15% water containing 0.1% acetic acid (solvent A) and 85% MeOH (solvent B) for a total run time of 40 minutes at 220 nm. The sample was injected at a concentration of 0.1 mg crude dried extract/mL in a volume of 50 μL per cycle. Fractions were collected every 2 minutes. F1-F9 represent the nine fractions into which the peaks were divided.

Figure 3B:
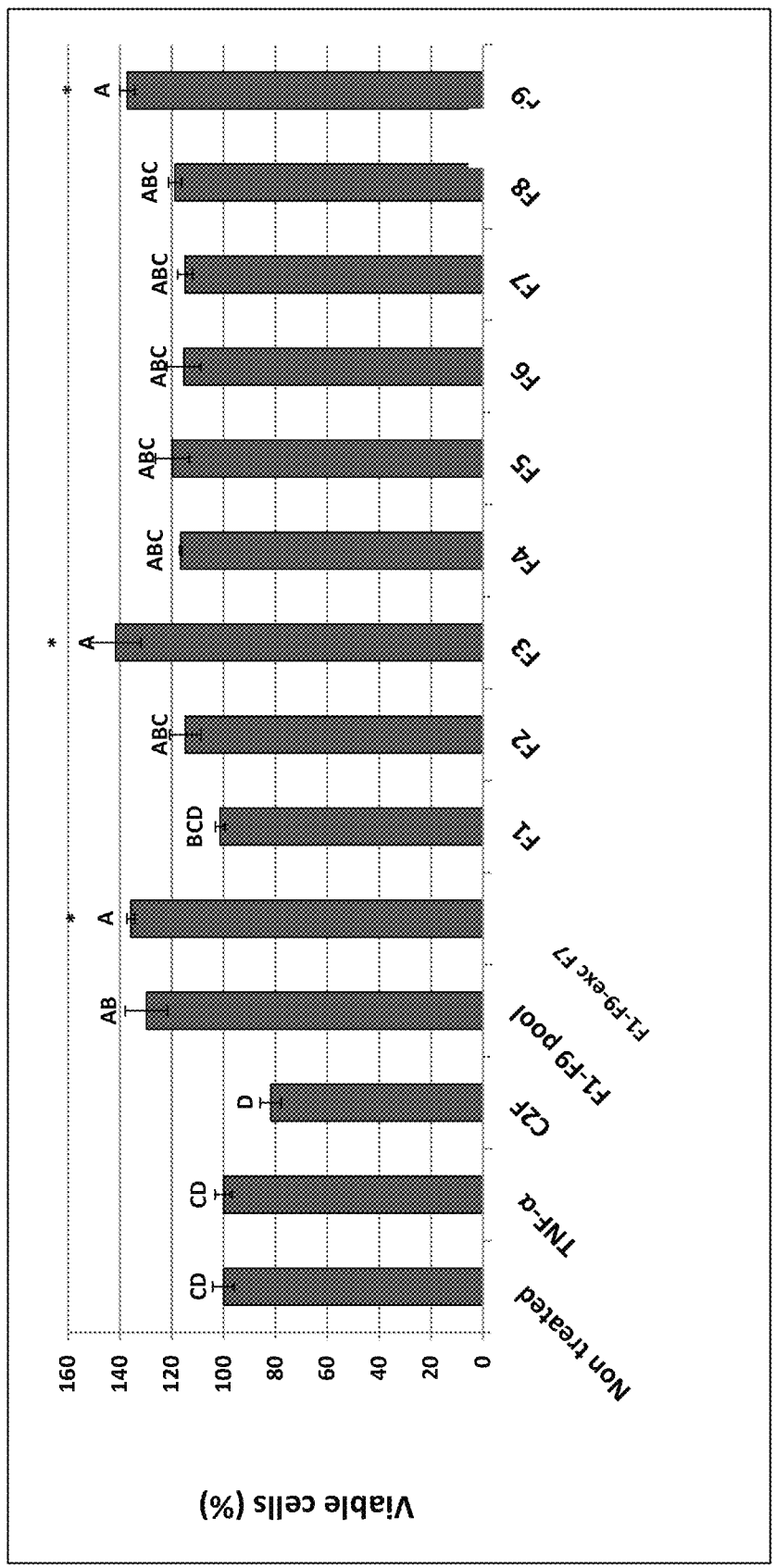

FIG. 3B depicts Determination of HCT116 cell viability using Alamar Blue fluorescence (resazurin assay) as a function of live cell number. HCT116 cells were seeded (50,000 per well) in triplicate in 500 μL growing media and incubated for 24 hours at 37° C. in a humidified 5% $CO_2$-95% air atmosphere. Cells were treated with 300 ng/mL TNF-α and 50 μL of C. sativa ethanol extract of C2F or fractions for 4 hours. Non-treated are the cells without TNF-α and treatments. Next, the cells were incubated with Alamar Blue for 2 hours. Relative fluorescence at the excitation/emission of 544/590 nm was measured. Values were calculated as percentage of live cells relative to the non-treated (cells without TNF-α and treatments) control after reducing the autofluorescence of Alamar Blue without cells. Error bars indicate SE (n=3). *, *** Indicate data statistically significantly different in comparison with the control (TNF-α treated cells) at p≤0.01 and p≤0.0001, respectively. Levels with different letters are significantly different from all combinations of pairs by Tukey's HSD.

FIG. 3C depicts Determination of HCT116 cell viability using Alamar Blue fluorescence (resazurin assay) as a function of live cell number. HCT116 cells were seeded (50,000 per well) in triplicate in 500 μL growing media and incubated for 24 hours at 37° C. in a humidified 5% $CO_2$-95% air atmosphere. Cells were treated with 300 ng/mL TNF-α and 50 μL of C. sativa ethanol extract of C2F or fractions for 4 hours. Non-treated are the cells without TNF-α and treatments. Next, the cells were incubated with Alamar Blue for 2 hours. Relative fluorescence at the excitation/emission of 544/590 nm was measured. Values were calculated as percentage of live cells relative to the non-treated (cells without TNF-α and treatments) control after reducing the autofluorescence of Alamar Blue without cells. Error bars indicate SE (n=3). , * Indicate data statistically significantly different in comparison with the control (TNF-α-treated cells) at p≤0.001 and p≤0.0001, respectively. Levels with different letters are significantly different from all combinations of pairs by Tukey's HSD.

Figure 4:
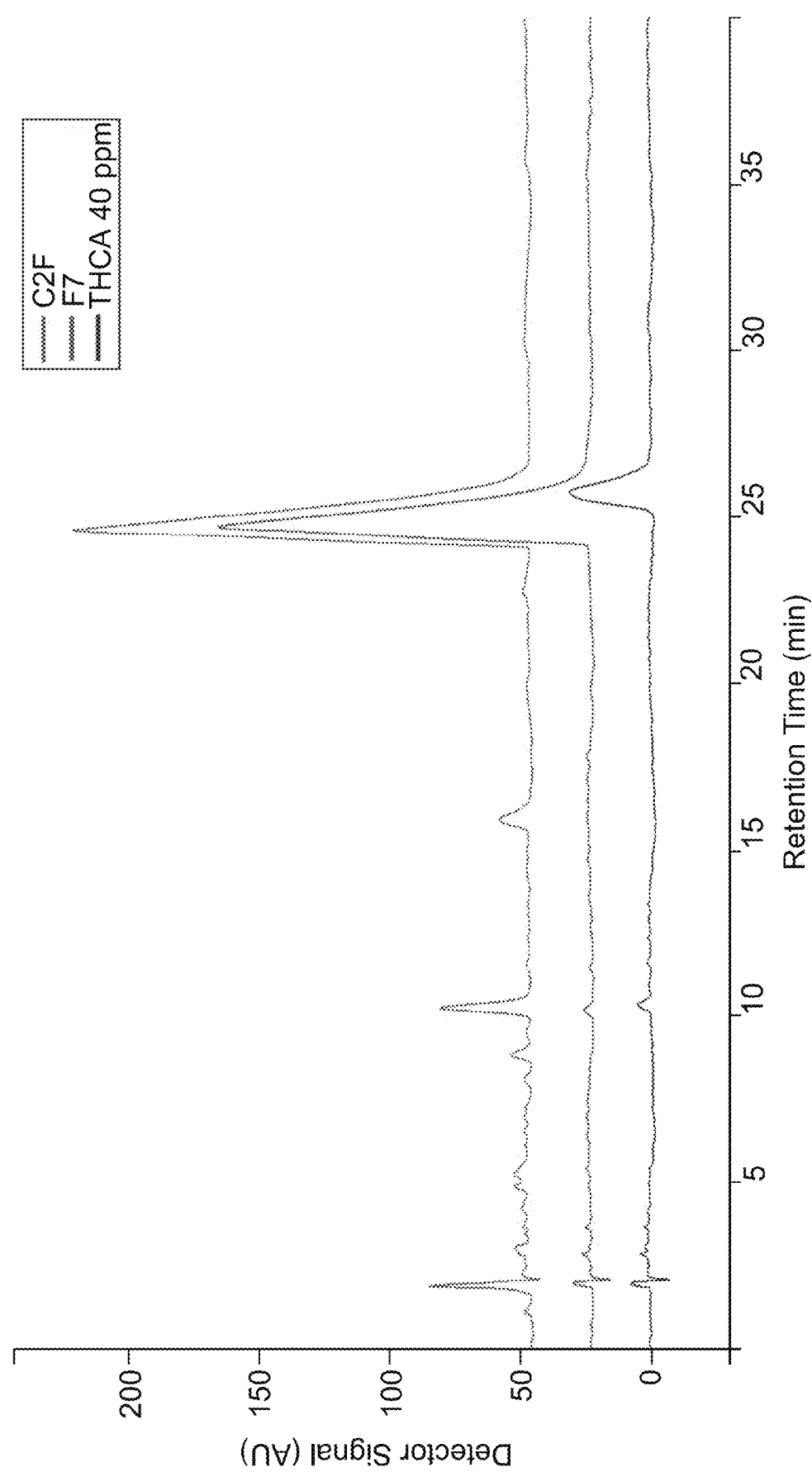

FIG. 4 depicts HPLC profile of C2F, F7 and THCA. Chromatograms of THCA standard at 40 ppm (marked in blue), whole C. sativa extract at 0.1 mg/mL (marked in green) and F7 at 0.04 mg/mL (marked in red). All samples were injected in a volume of 20 µL and were obtained from isocratic elution with a mixture of 15% water containing 0.1% acetic acid (solvent A) and 85% MeOH (solvent B) for a total run time of 40 minutes at 220 nm.

FIGS. 5A-B depict the effect of C. sativa C2F and HPLC-fractions (F1-F9) in different combinations on HCT116 cell viability. (FIG. 5A) Determination of HCT116 cell viability using XTT assay as a function of live cell number. Cells were seeded and treated with C. sativa ethanol extracts (C2F), F1-F9-excluding F7 (HPLC fractions of C2F) and Fractions F1-F9 including F7 (HPLC fractions of C2F) at $IC_{50}$ dose of C2F crude (58 µg/mL) and F-F9 diluted as C2F crude along with 50 ng/mL of TNF-α for 48 hours. Next, the cells were incubated with XTT reagent for 2 hours. Absorbance was recorded at 490 nm with 650 nm of reference wavelength. Values were calculated as percentage of live cells relative to the non-treated (cells without TNF-α and treatments) control after reducing the absorbance without cells. (FIG. 5B) Determination of synergism of C2F Fraction 7 (F7) in combination with Fraction 2 (F2) and Fraction 3 (F3) on HCT116 cell viability using XTT assay as a function of live cell number. Cells were seeded and treated with $IC_{50}$ doses of F2 (7 µg/mL), F3 (36 µg/mL), F7 (20 µg/mL), the combinations of F2 with F3, F7 with F2 and F7 with F3 along with 50 ng/mL of TNF-α for 48 hours. Next, the cells were incubated with XTT reagent for 2 hours. Absorbance was recorded at 490 nm with 650 nm of reference wavelength. Values were calculated as percentage of live cells relative to the non-treated (cells without TNF-α and treatments) control after reducing the absorbance without cells. Error bars indicate ±SE (n=3). Levels with different letters are significantly different from all combinations of pairs by Tukey's HSD.

FIGS. 6A-B depict the effect of C. sativa F1 and F3 on HT29 (FIG. 6A) cell and CaCO2 (FIG. 6B) cell viability. Cell viability was determined using XTT assay as a function of live cell number. Cells were seeded and treated with $IC_{50}$ doses of F3 (36 µg/mL), F7 (20 µg/mL) and the combination of F7 with F3 along with 50 ng/mL of TNF-α for 48 hours. Next, the cells were incubated with XTT reagent for 2 hours. Absorbance was recorded at 490 nm with 650 nm of reference wavelength. Values were calculated as percentage of live cells relative to the non-treated (cells without TNF-α and treatments) control after reducing the absorbance without cells. Error bars indicate ±SE (n=3). Levels with different letters are significantly different from all combinations of pairs by Tukey's HSD.

Figure 6C:
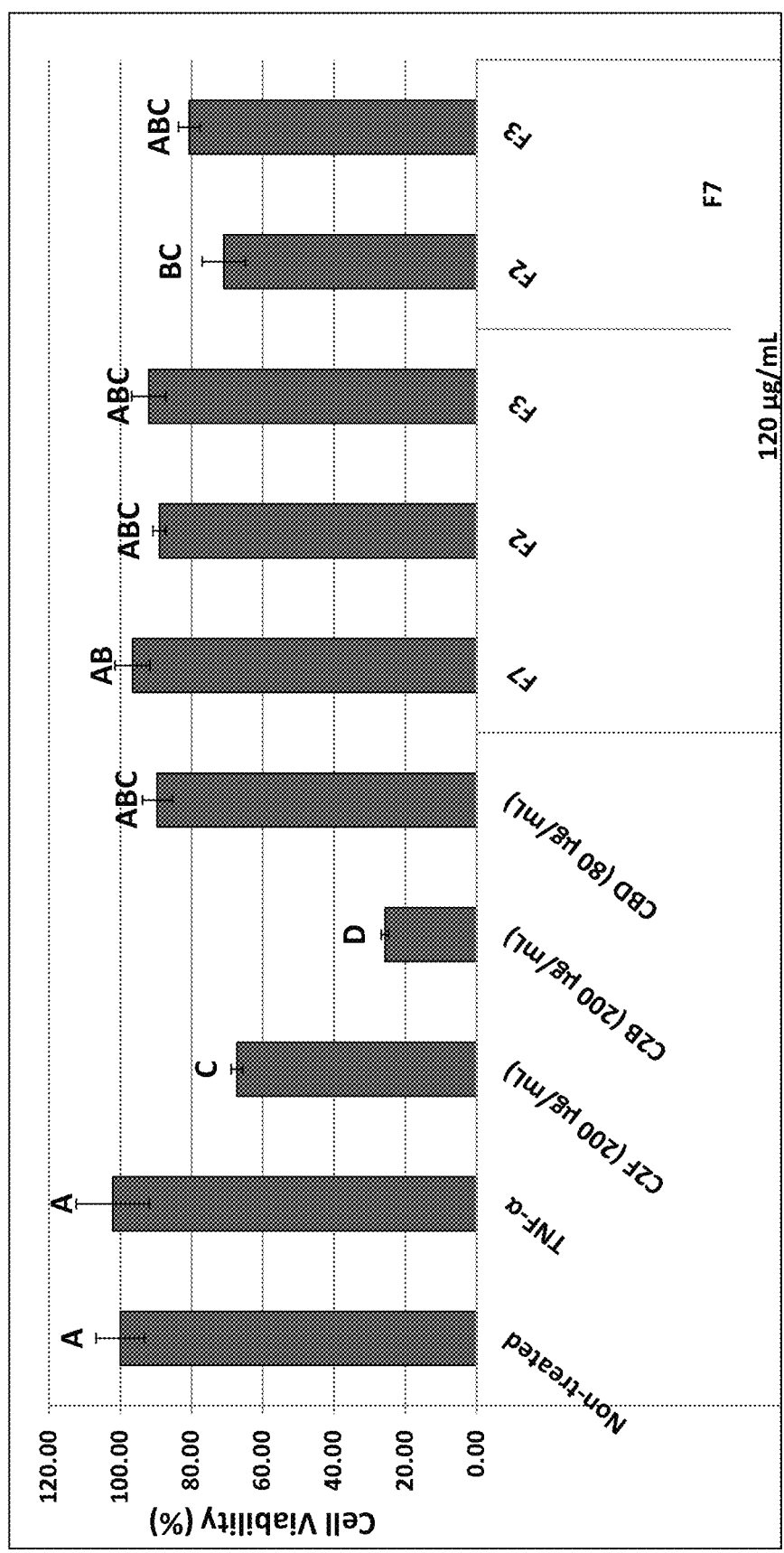

FIG. 6C depicts the effect of C. sativa C2F, C2B, CBD and active fraction combination on CCD18 healthy colon cell viability. Determination of CCD18 cell viability using Alamar Blue fluorescence (Resazurin assay) as a function of live cell number. Cells were seeded and treated with C. sativa ethanol extracts of fresh inflorescences (C2F, 200 µg/mL), heated inflorescences (C2B, 200 µg/mL), pure Cannabidiol (CBD, 8 µg/mL), F7 (120 µg/mL), F2 (120 µg/mL), F2 (120 µg/mL) and combination F7 with F2 & F3 along with 50 ng/mL of TNF-α for 16 hours. Next, the cells were incubated with Alamar Blue for 4 hours. Relative fluorescence at the excitation/emission of 544/590 nm was measured. Values were calculated as percentage of live cells relative to the non-treated (cells without TNF-α and treatments) control after reducing the auto fluorescence of Alamar Blue without cells. Error bars indicate ±SE (n=3). Levels with different letters are significantly different from all combinations of pairs by Tukey HSD.

FIGS. 7A-C depict the synergistic effect in the combination of C2F Fraction 7 (F7) and Fraction 3 (F3), and interaction between THCA and CBGA. (FIG. 7A) Dose-effect curves of F3 without F7 ($IC_{50}$=36.47 µg/mL) and F3 with F7 ($IC_{50}$=10.79 µg/mL) on viability of HCT116 colon cancer cells. Cells were seeded and treated with different concentration of F3 (3 µg/mL to 160 µg/mL) with and without $IC_{50}$ dose of F7 (20 µg/mL) along with 50 ng/mL of TNF-α for 48 hours. Next, the cells were incubated with XTT reagent for 2 hours. Absorbance was recorded at 490 nm with 650 nm of reference wavelength. Values were calculated as percentage of live cells relative to the non-treated (cells without TNF-α and treatments) control after reducing the absorbance without cells. (FIG. 7B) Dose-effect curves of F7 without F3 ($IC_{50}$=21.7 µg/mL) and F7 with F3 ($IC_{50}$=1.88 µg/mL) on viability of HCT116 colon cancer cells. Cells were seeded and treated with different concentration of F7 (7.9 µg/mL to 380 µg/mL) with and without $IC_{50}$ dose of F3 (36 µg/mL) along with 50 ng/mL of TNF-α for 48 hours. Next, the cells were incubated with XTT reagent as described in FIG. 7A. For dose response assays, data points were connected by non-linear regression lines of the sigmoidal dose-response relation. GraphPad Prism was employed to produce dose-response curve and $IC_{50}$ doses. (FIG. 7C) Synergism calculation for combinations of standards (THCA and CBGA). Top table, THCA in constant concentration of 13.14 µg/mL and CBGA in different concentrations (6.67 µg/mL 53.3 µg/mL). Marked in red are concentrations which showed synergism between standards as was determined by XTT assay on HCT116 cells. Bottom table, CBGA in constant concentration of 28 µg/mL and THCA in different concentrations (4 µg/mL-50 µg/mL). Marked in red are concentrations which showed synergism between standards as was determined by XTT assay on HCT116 cells.

FIGS. 7D-E depict the determination of $IC_{50}$ dose of Fraction 3 (F3) and Fraction 7 (F7). (FIG. 7D) Dose-effect curves of F3 on viability of HCT116 colon cancer cells. Cells were seeded and treated with different concentration of F3 (3 µg/mL to 160 µg/mL) along with 50 ng/mL of TNF-α for 48 hours. Next, the cells were incubated with XTT reagent for 2 hours. Absorbance was recorded at 490 nm with 650 nm of reference wavelength. Values were calculated as percentage of live cells relative to the non-treated (cells without TNF-α and treatments) control after reducing the absorbance without cells. For dose response assays, data points were connected by non-linear regression lines of the sigmoidal dose-response relation. GraphPad Prism was employed to produce dose-response curve and $IC_{50}$ doses. (FIG. 7E) Dose-effect curves of F7 on viability of HCT116 colon cancer cells. Cells were seeded and treated with different concentration of F7 (7.9 µg/mL to 380 µg/mL) along with 50 ng/mL of TNF-α for 48 hours. Next, the cells were incubated with XTT reagent for 2 hours. Absorbance was recorded at 490 nm with 650 nm of reference wavelength. Values were calculated as percentage of live cells relative to the non-treated (cells without TNF-α and treatments) control after reducing the absorbance without cells.

For dose response assays, data points were connected by non-linear regression lines of the sigmoidal close-response relation. GraphPad Prism was employed to produce dose-response curve and $IC_{50}$ doses.

FIGS. 8A-D depict determination of the cytotoxic effect of fraction 7 (F7), Fraction 3 (F3) and combination of F7 with F3 on cells occur through apoptosis or necrosis. HCT116 cells were treated with F7 (20 µg/mL), F3 (36 µg/mL), combination of F7 with F3 and solvent control (methanol) along with TNF-α (50 ng/ml) for 24 hours (FIGS. 8A, 8B) and 48 hours (FIGS. 8C, 8D). The treated cells were harvested and analyzed in FACS following Annexin V-FITC and PI staining. The percentage of live, necrotic, early and late apoptosis cells were analyzed from 10000 events per treatment.

Figure 9:
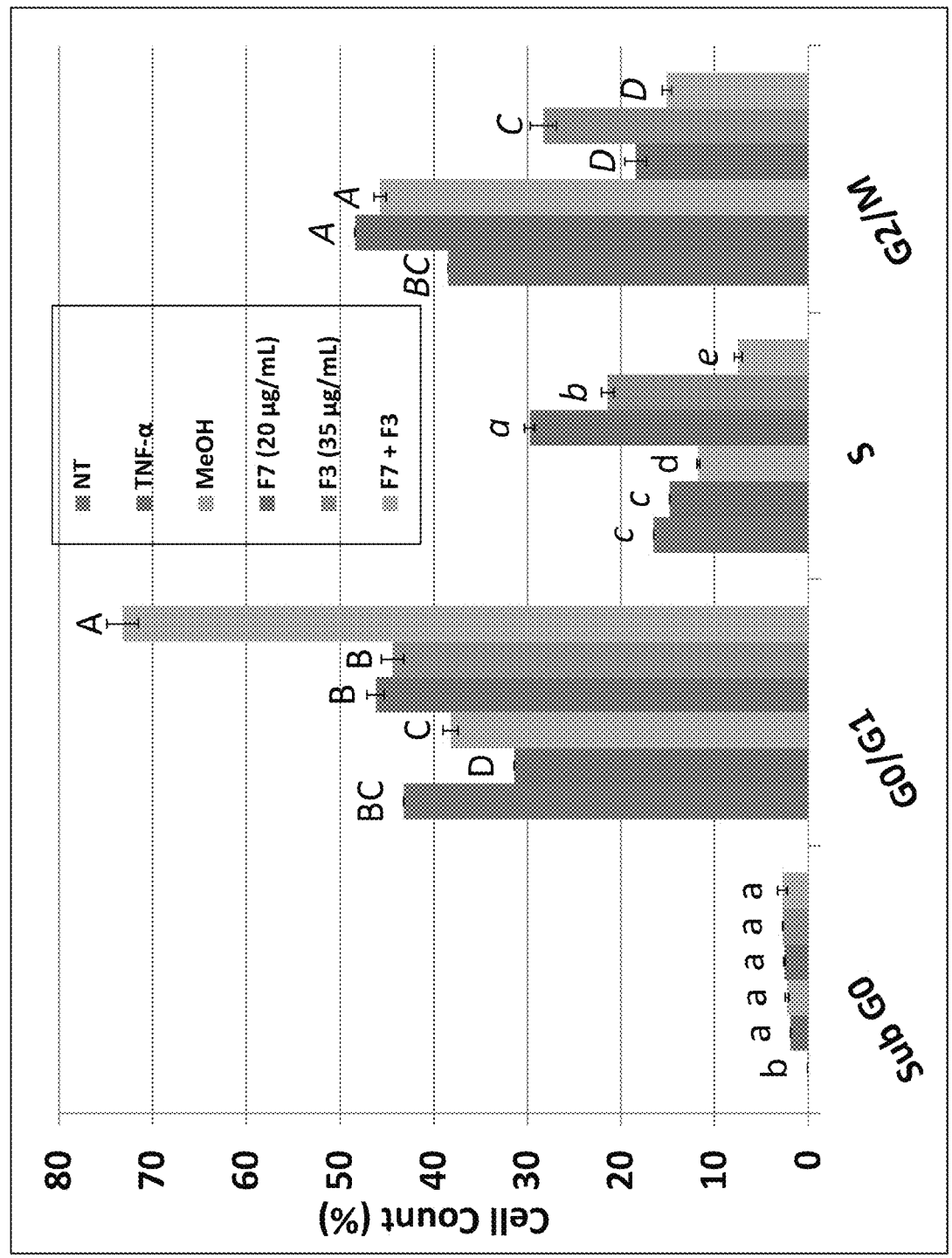

FIG. 9 depicts determination of the cell cycle arrest by the fraction 7 (F7), Fraction 3 (F3) and combination of F7 with F3. Starved HCT116 cells were treated with F7 (20 µg/mL), F3 (36 µg/mL), combination of F7 with F3 and solvent control (methanol) along with TNF-α (50 ng/ml) for 24 hours. The treated cells were harvested, fixed and analyzed in FACS following PI staining. The percentage of cells in Sub-G0, G0/G1, S and G2/M phase were analyzed from 10000 events per treatment.

FIGS. 10A-B depict the hierarchical clustering and Venn diagram of genes differentially expressed in HCT116 cells treated with combination of F7 with F3. (FIG. 10A) Hierarchical clustering and Pearson correlations among the 4 conditions based on the genes expression followed by a log 2 transform. Red and green colors represent positive and negative correlations, respectively. Pearson correlations were calculated with the R software. (FIG. 10B) Venn diagrams illustrating the relationships between significantly expressed genes in the three treatments against the control.

Figure 11A:
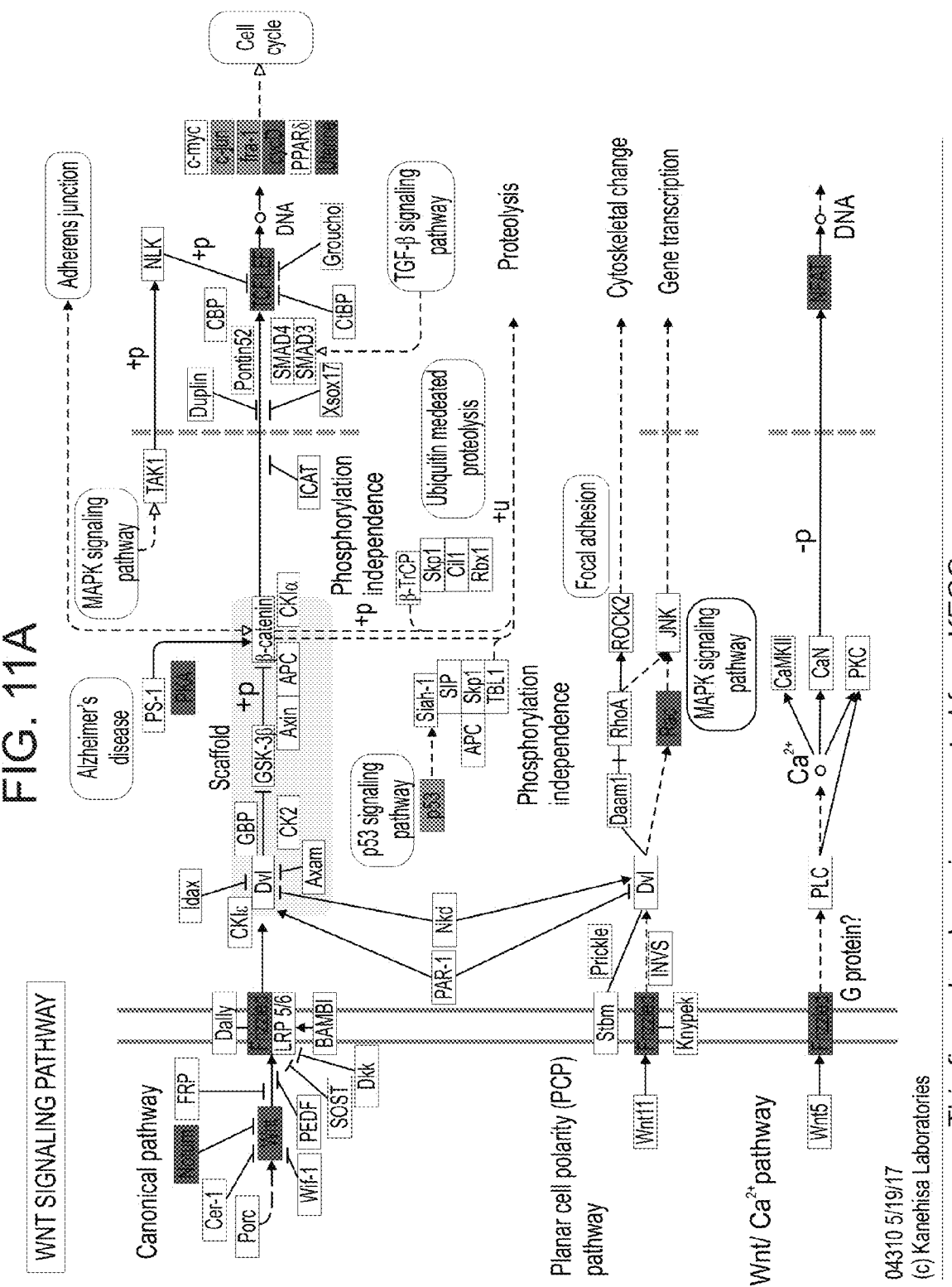

FIGS. 11A-B depict the genetic pathways of genes differentially expressed in HCT116 cells treated with combination of F7 with F3. Genes of Wnt (FIG. 11A) and apoptotic (FIG. 11B) signaling pathways according to KEGG (www(dot)genome(dot)jp/kegg/). Green boxes—significantly upregulated genes; red boxes—significantly downregulated genes. Of note, the figures were incorporated from KEGG (www(dot)genome(dot)jp/kegg/).

FIGS. 12A-C depict the determination of HCT116 cell viability using Alamar Blue fluorescence (Resazurin assay) as a function of cytotoxic effect. HCT116 cells were seeded (50,000 per well) in triplicate in 500 µL growing media and incubated for 24 h at 37° C. in a humidified 5% $CO_2$-95% air atmosphere. Cells were treated with 50 ng/mL TNF-α and the treatments [C. sativa ethanol extracts of C2F (0.2 mg/mL; FIG. 12A), F7 (0.08 mg/mL; FIG. 12B) and 0.12 mM THCA; FIG. 12C)], with and without antagonists to CB1, CB2 and GPR55 receptors. C2F (0.2 mg/mL; FIG. 12A), F7 (0.08 mg/mL; FIG. 12B) and 0.12 mM THCA (FIG. 12C) served as a positive control. Non-treated are the cells without TNF-α and treatments. Relative fluorescence at the excitation/emission of 544/590 nm was measured. Values were calculated as percentage of live cells relative to the non-treated (cells without TNF-α and treatments) control after reducing the autofluorescence of Alamar Blue without cells. Error bars indicate ±SEM (n=3). *, , * indicates data statistically significantly different in comparison with the control (TNF-α treated cells) at p≤0.05, p≤0.001, p≤0.0001 respectively. Levels with different letters are significantly different from all combinations of pairs by turkey HSD.

Figure 12D:
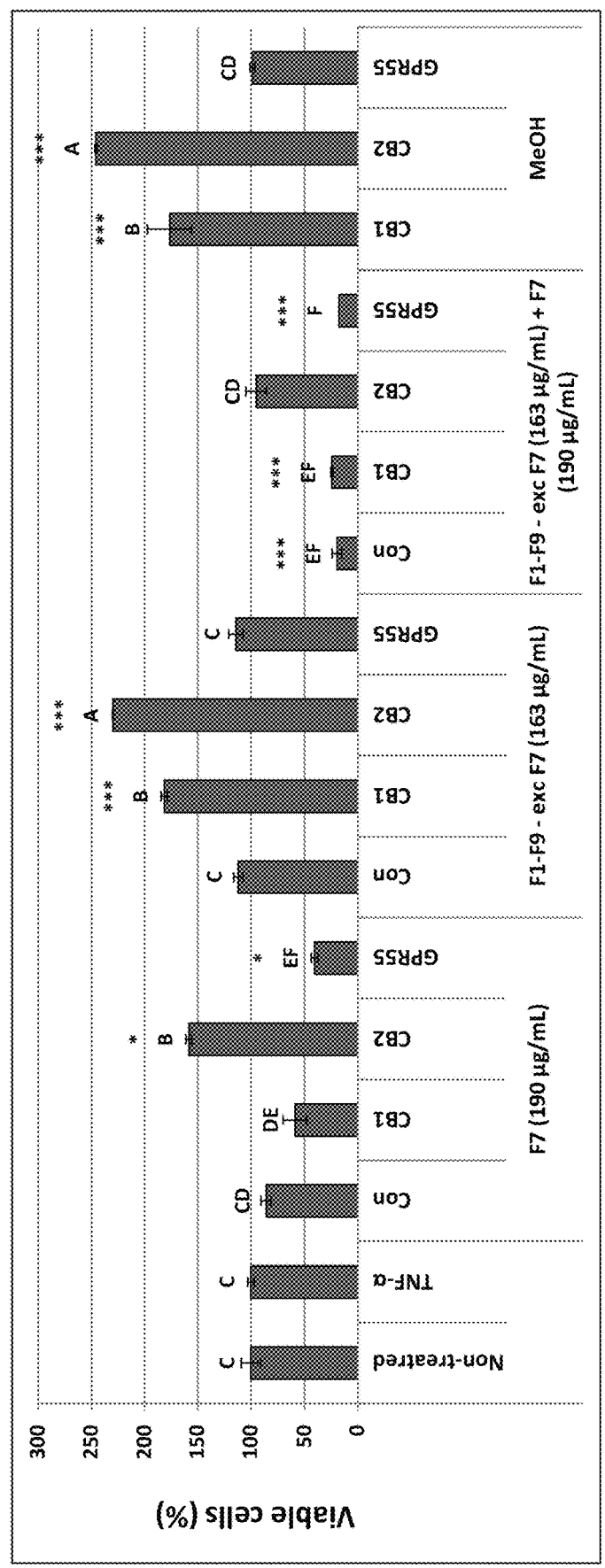

FIG. 12D depicts determination of HCT116 cell viability using Alamar Blue fluorescence (resazurin assay) as a function of cytotoxic effect. HCT116 cells were seeded (50,000 per well) in triplicate in 500 µL growing media and incubated for 24 hours at 37° C. in a humidified 5% $CO_2$-95% air atmosphere. Cells were treated with 300 ng/mL TNF-α and 50 µL of C. sativa ethanol extract of C2F fractions for 4 hours. Treatments with F7, F1-F9, and combination of fractions without antagonists served as a positive control (Con). Non-treated are the cells without TNF-α and treatments. Next, the cells were incubated with Alamar Blue for 2 hours. Relative fluorescence at the excitation/emission of 544/590 nm was measured. Values were calculated as percentage of live cells relative to the non-treated (cells without TNF-α and treatments) control after reducing the autofluorescence of Alamar Blue without cells. Error bars indicate—SE (n=3). *, *** Indicate data statistically significantly different in comparison with the control (TNF-α-treated cells) at p≤0.01 and p≤0.0001, respectively. Levels with different letters are significantly different from all combinations of pairs by Tukey's HSD. CB1, cannabinoid receptor type 1; CB2, cannabinoid receptor type 2.

Figure 13A:
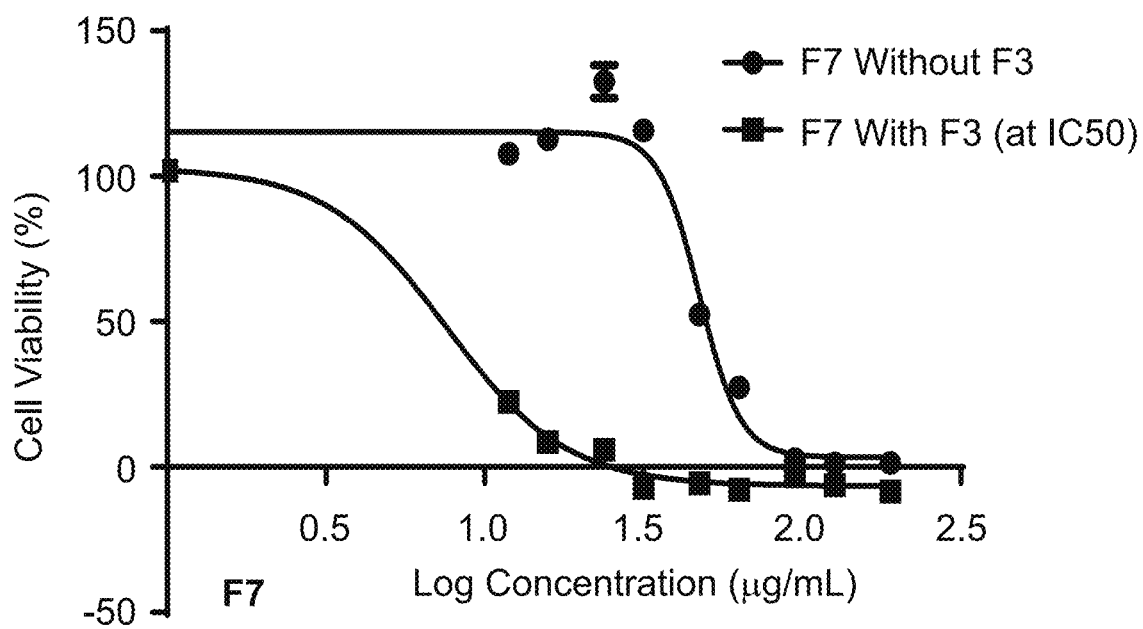
Figure 13B:
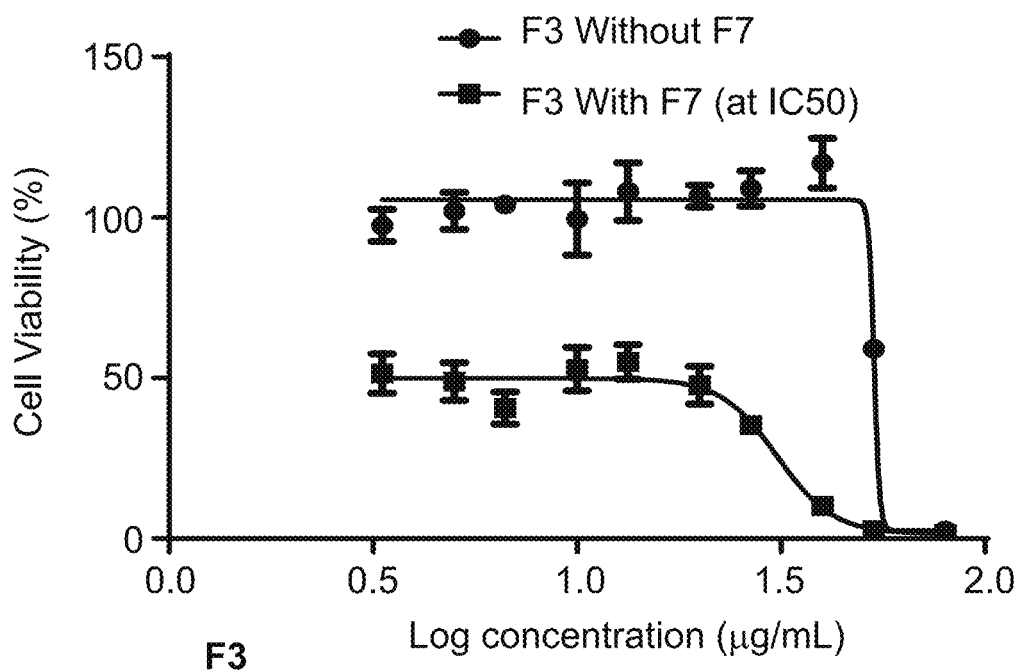

FIGS. 13A-B depict the (FIG. 13A) $IC_{50}$ of F7 with and without F3 and (FIG. 13B) $IC_{50}$ of F3 with and without F7 on MDA-MB-231 breast cancer cells. (FIG. 13A) Dose-effect curves of F3 without F7 ($IC_{50}$=36.47 µg/mL) and F3 with F7 ($IC_{50}$=10.79 µg/mL) on viability of MDA-MB-231 breast cancer cells. Cells were seeded and treated with different concentration of F3 (3 µg/mL to 160 µg/mL) with and without $IC_{50}$ dose of F7 (20 µg/mL) along with 50 ng/mL of TNF-α for 48 hours. Next, the cells were incubated with XTT reagent for 2 hours. Absorbance was recorded at 490 nm with 650 nm of reference wavelength. Values were calculated as the percentage of live cells relative to the non-treated control (cells without TNF-α and treatments) after reducing the absorbance without cells. (FIG. 13B) Dose-effect curves of F7 without F3 ($IC_{50}$=21.7 µg/mL) and F7 with F3 ($IC_{50}$=1.88 µg/mL) on the viability of MDA-MB-231 breast cancer cells. Cells were seeded and treated with different concentration of F7 (7.9 µg/mL to 380 µg/mL) with and without the $IC_{50}$ dose of F3 (36 µg/mL) and with 50 ng/mL of TNF-α for 48 hours. The cells were then incubated with XTT reagent as described in (FIG. 13A). For dose response assays, data points were connected by non-linear regression lines of the sigmoidal close-response relation. GraphPad Prism was employed to produce dose-response curves and $IC_{50}$ doses.

Figure 14A:
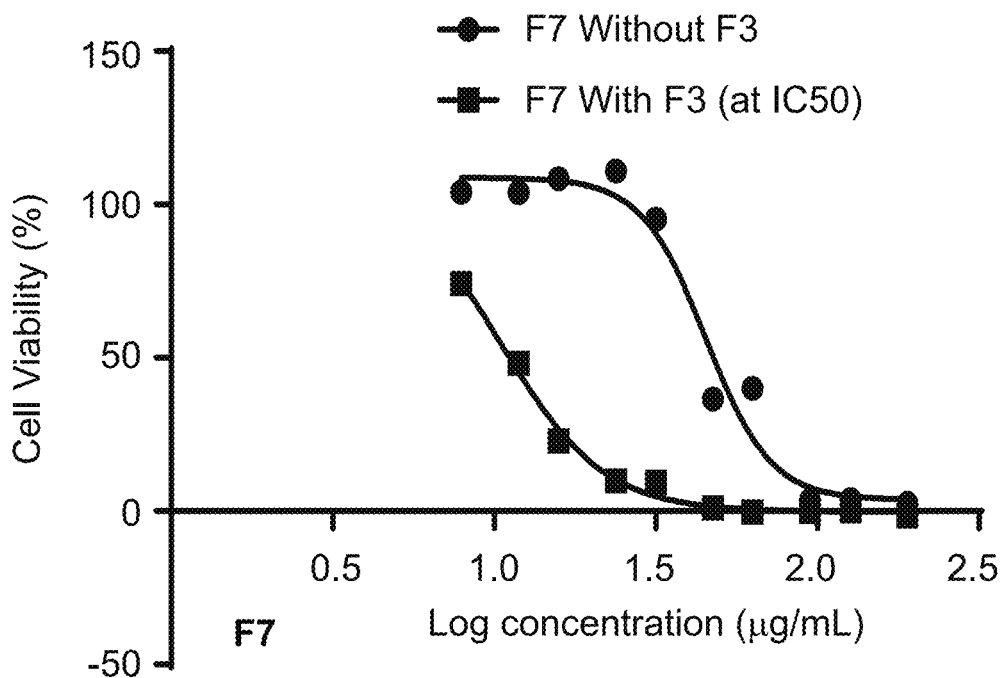
Figure 14B:
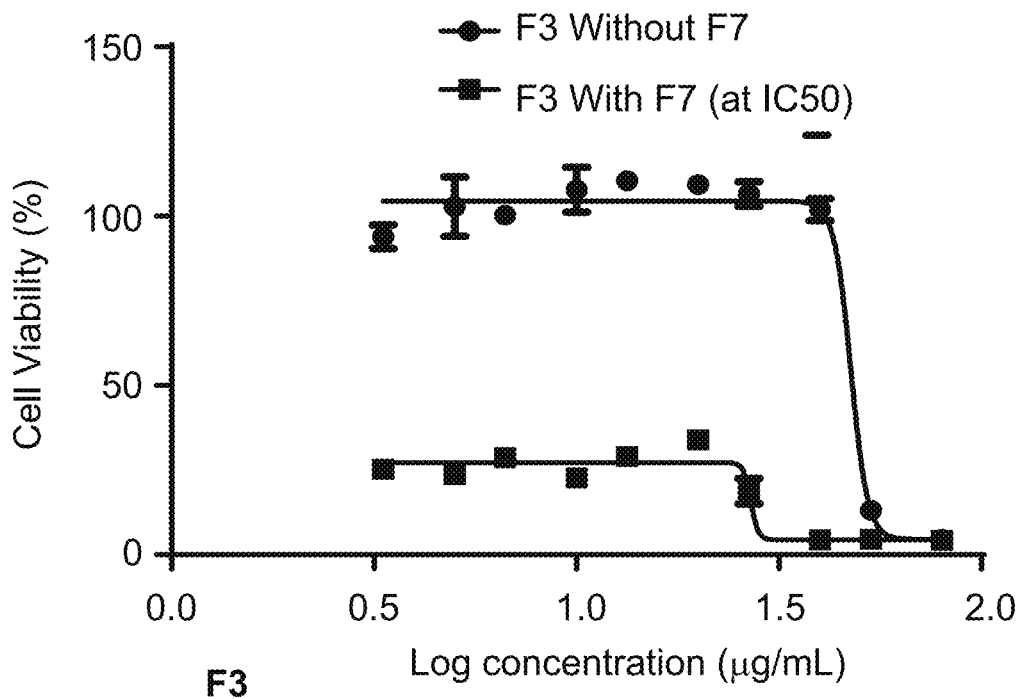

FIGS. 14A-B depict the (FIG. 14A) $IC_{50}$ of F7 with and without F3 and (FIG. 14B) $IC_{50}$ of F3 with and without F7 on A172 glioma cells. (FIG. 14A) Dose-effect curves of F3 without F7 ($IC_{50}$=36.47 µg/mL) and F3 with F7 ($IC_{50}$=10.79 µg/mL) on viability of A172 glioma cancer cells. Cells were seeded and treated with different concentration of F3 (3 µg/mL to 160 µg/mL) with and without $IC_{50}$ dose of F7 (20 µg/mL) along with 50 ng/mL of TNF-α for 48 hours. Next, the cells were incubated with XTT reagent for 2 hours. Absorbance was recorded at 490 nm with 650 nm of reference wavelength. Values were calculated as the percentage of live cells relative to the non-treated control (cells without TNF-α and treatments) after reducing the absorbance without cells. (FIG. 14B) Dose-effect curves of F7 without F3 ($IC_{50}$=21.7 µg/mL) and F7 with F3 ($IC_{50}$=1.88 µg/mL) on the viability of A172 glioma cancer cells. Cells were seeded and treated with different concentration of F7 (7.9 µg/mL to 380 µg/mL) with and without the $IC_{50}$ dose of F3 (36 µg/mL) and with 50 ng/mL of TNF-α for 48 hours. The cells were then incubated with XTT reagent as described in (FIG. 14A). For dose response assays, data points were connected by non-linear regression lines of the sigmoidal dose-response relation. GraphPad Prism was employed to produce dose-response curves and $IC_{50}$ doses.

DESCRIPTION OF SPECIFIC EMBODIMENTS OF THE INVENTION

The present invention, in some embodiments thereof, relates to compositions and methods for treating cancerous diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Colorectal cancer (CRC) is the third most common cancer diagnosis and fourth leading cause of cancer-related mortality worldwide. Different preparations of marijuana (*Cannabis sativa*) have been shown to have beneficial effects on proliferation, metastasis, angiogenesis and induction of apoptosis in a variety of cancer cell types. However, *C. sativa* extracts contain hundreds of compounds. Accumulating knowledge has indicated the benefits of Δ9-tetrahydrocannabinol (THC), cannabidiol (CBD) and cannabigerol (CBG), and receptor agonists or antagonists, however, only little is known on other compounds in cannabis extracts that may have anti-cancer activity.

The present inventor has now uncovered that liquid chromatography fractions of cannabis inflorescence extracts are effective as cytotoxic agents and can efficiently eradicate cancer cells. The cytotoxic activity of *C. sativa* inflorescence extracts and fractions obtained therefrom was tested on CRC, breast cancer and glioma cancer cells and adenomatous polyps.

Specifically, the present inventors obtained fresh cannabis flower polar extracts which exhibited specific cytotoxic activity towards cancer cells (Example 1 of the examples section which follows). These extracts were further fractionated into several distinct fractions among them fractions which illustrated specific cytotoxic activity, i.e. Fractions F2, F3 and F7. Fraction F7 was shown to comprise more than 80% THCA (Table 3 in the examples section which follows), Fraction F3 was shown to comprise more than 80% CBGA (Table 2 in the examples section which follows), and Fraction F2 was shown to comprise about 20% CBC and about 20% THCA (data not shown). Significant cytotoxic activity was observed for fraction F2 (see FIG. 5B and Example 7 of the Examples section which follows). Also, while fractions F7 and F3 exhibited only minor cytotoxic activity in the examined assays (see Examples 3 and 9 of the Examples section which follows), synergistic activity was evident in different cancerous cell types when combining treatment with fractions F7 and F3 or with F7 and F2 (see Examples 7-8 and 14 of the Examples section which follows). The cytotoxic activity of the interacting compounds induced cell cycle arrest and apoptotic cell death (see Examples 9-10 of the Examples section which follows). Moreover, the effect of Fraction F7 is likely mediated via CB2 receptors (see Examples 13 of the Examples section which follows).

Taken together, the present inventors propose that these cannabis extracts may be used as anti-cancer therapeutic agents.

Thus, according to one aspect of the present invention, there is provided a method of generating a cytotoxic composition, the method comprising: (i) adding a polar solvent to a dry Cannabis inflorescence so as to obtain a crude extract; (ii) filtering the crude extract so as to obtain a filtered extract; (iii) fractionating the filtered extract on a high pressure liquid chromatography (HPLC); (iv) collecting the fractions detectable by a detector operated at 220 nm and comprising a component selected from the group consisting of (a) CBGA; and (b) CBC and THCA.

*Cannabis* is a genus of flowering plants in the family Cannabaceae that includes three different species, *Cannabis sativa, Cannabis indica* and *Cannabis ruderalis*. The term *Cannabis* encompasses wild type *Cannabis* and also variants thereof, including cannabis chemovars which naturally contain different amounts of the individual cannabinoids. For example, some *Cannabis* strains have been selectively bred to produce high or low levels of THC and other cannabinoids. Accordingly, *Cannabis* cultivars that are rich in THCA, CBGA and/or CBC can be used in accordance with the present teachings.

According to one embodiment, the *Cannabis* plant is a wild-type plant.

According to one embodiment, the *Cannabis* plant is transgenic.

According to one embodiment, the *Cannabis* plant is genomically edited.

According to one embodiment, the *Cannabis* plant is *Cannabis sativa* (*C. sativa*).

The extract may be derived from a cultivated *Cannabis* plant (i.e. not grown in their natural habitat) or may be derived from *Cannabis* plants which grow in the wild.

The tissue of the *Cannabis* plant from which the extract is typically obtained is the inflorescence. Accordingly, the extract may be obtained from the complete flower head of a plant including stems, stalks, bracts, and flowers. However, it will be appreciated that a cannabis extract of the invention may be obtained from only part of the inflorescence, such as from the bracts and/or flowers.

According to one embodiment, the extract is obtained from a fresh plant (i.e. a plant not heated prior to the extraction process). Fresh plants include plants taken immediately following harvesting (e.g., up to an hour or several hours) for extraction as well as plants frozen immediately after harvesting (e.g. at about −70° C. to −90° C., e.g. at −80° C., for any required length of time) prior to extraction.

According to one embodiment, the extract is obtained from fresh inflorescence.

According to one embodiment, the extract is obtained from a frozen inflorescence (e.g. frozen immediately after harvesting at about −70° C. to −90° C., e.g. at −80° C., for any required length of time). Thus, for example, the extract may be obtained from a cryopreserved inflorescence, or from an inflorescence frozen in liquid nitrogen or in dry ice.

According to one embodiment, the extract is obtained from an inflorescence which has not been subjected to heating (such as heating at e.g. at 120° C. to 180° C., e.g. at 150° C., for any length of time, such as for 1-5 hours).

According to one embodiment, the extract is obtained from dry Cannabis inflorescence. Drying the inflorescence may be carried out using any method known in the art, such as by pulverizing with liquid nitrogen or with dry-ice/alcohol mixture.

In some embodiments, the polar solvent comprises a polar, protic solvent (e.g., ethanol or methanol). In some embodiments, the polar solvent comprises a polar, aprotic solvent (e.g., acetone). Polar solvents suitable for use with the present invention include, but are not limited to, ethanol, methanol, n-propanol, iso-propanol, a butanol, a pentanol, acetone, methylethylketone, ethylacetate, acetonitrile, tetrahydrofuran, dimethylformamide, dimethylsulfoxide, water, and combinations thereof.

In a particular embodiment, the polar solvent is ethanol (e.g. absolute ethanol i.e. above 99.8%, or in the range of 99-70% in water).

The concentration or amount of a polar solvent used to dry Cannabis inflorescence can be varied. Generally, the ratio of a dry Cannabis inflorescence to a polar solvent (weight to volume) is the amount of a polar solvent sufficient to extract about 70% or more, about 75% or more, about 85% or more, about 90% or more, about 95% or more, about 97% or more, or about 99% or more of a composition having a cytotoxic activity. In some embodiments, the ratio of polar solvent to dry Cannabis inflorescence is about 1:2 to about 1:20 (w/v), e.g. about 1:4 to about 1:10 (w/v).

In particular embodiments, the extract is an ethanol extract.

In particular embodiments, absolute ethanol is added to the dry inflorescence at a sample-to-absolute ethanol ratio of 1:4 (w/v).

In some embodiments, the dry Cannabis inflorescence is contacted with a polar solvent (e.g. ethanol) for about 15 minutes or more, about 30 minutes or more, about 1 hour or more, about 2 hours or more, or about 5 hours or more.

Temperature can also be controlled during the contacting. In some embodiments, the dry Cannabis inflorescence is contacted with a polar solvent at temperature of about 15° C. to about 35° C., or about 20° C. to about 25° C.

According to a specific embodiment, the dry Cannabis inflorescence is contacted with a polar solvent (e.g. ethanol) while being constantly mixed e.g. on a shaker.

In some embodiments, the process of the present invention comprises isolating a liquid extract (i.e. filtered extract) from the mixture (i.e. crude extract) comprising the liquid extract and solids. Suitable means for isolating the liquid extract (i.e. filtered extract) include those known in the art of organic synthesis and include, but are not limited to, gravity filtration, suction and/or vacuum filtration, centrifuging, setting and decanting, and the like. In some embodiments, the isolating comprises filtering a liquid extract through a porous membrane, syringe, sponge, zeolite, paper, or the like having a pore size of about 1-5 μm, about 0.5-5 μm, about 0.1-5 μm, about 1-2 μm, about 0.5-2 μm, about 0.1-2 μm, about 0.5-1 μm, about 0.1-1 μm, about 0.25-0.45 μm, or about 0.1-0.5 μm (e.g. about 2 μm, about 1 μm, about 0.45 μm, or about 0.25 μm).

According to a specific embodiment, the crude extract is filtered through a 0.45-μm syringe filter such as that commercially available from Merck, Darmstadt, Germany.

The present inventors contemplate drying (i.e. removal of the polar solvent) and/or freezing the filtered extract following generation thereof.

The method for drying the filtered extract (i.e. removing the polar solvent) is not particularly limited, and can include solvent evaporation at a reduced pressure (e.g., sub-atmospheric pressure) and/or an elevated temperature (e.g., above about 25° C.). In some embodiments, it can be difficult to completely remove a polar solvent from a liquid extract by standard solvent removal procedures such as evaporation. In some embodiments, processes such as co-evaporation, lyophilization, and the like can be used to completely remove the polar solvent from a liquid fraction to form a dry powder, dry pellet, dry granulate, paste, and the like. According to a specific embodiment the polar solvent is evaporated with a vacuum evaporator.

Following generation of the filtered extract, the present inventors further contemplate additional purification steps so as to further purify active agents from the extract.

Thus, for example, the present inventors further propose fractionating the filtered extract. Fractionating can be performed by processes such as, but not limited to: column chromatography, preparative high performance liquid chromatography ("HPLC"), reduced pressure distillation, and combinations thereof. According to a specific embodiment, fractionating is performed by HPLC.

In some embodiments, fractionating comprises resuspending the filtered extract in a polar solvent (such as methanol, as discussed above), applying the polar extract to a separation column, and isolating the cannabis extract having a cytotoxic activity by column chromatography.

An eluting solvent is applied to the separation column with the polar extract to elute fractions from the polar extract. Suitable eluting solvents for use include, but are not limited to, methanol, ethanol, propanol, acetone, acetic acid, carbon dioxide, methylethyl ketone, acetonitrile, butyronitrile, carbon dioxide, ethyl acetate, tetrahydrofuran, di-isopropylether, ammonia, triethylamine, N,N-dimethylformamide, N,N-dimethylacetamide, and the like, and combinations thereof.

According to an alternative or an additional embodiment, liquid chromatography comprises high performance liquid chromatography (HPLC).

According to an alternative or an additional embodiment, liquid chromatography is performed on a reverse stationary phase.

According to an alternative or an additional embodiment, liquid chromatography is performed using a mobile phase comprising from 10 to 30% acidic aqueous solution and from 90 to 70% alcohol.

According to a specific embodiment, an eluting solvent comprises 15% solvent A (0.1% acetic acid in water) and 85% solvent B (methanol).

According to an alternative or an additional embodiment, fraction separation may be carried out on a HPLC comprising a stationary phase comprising RP-18 end capped column (such as a 250 mm×4.6 mm available from e.g. Merck KGaA, Darmstadt, Germany) with a guard column (e.g. 4 mm×4 mm), and a mobile phase of 15% solvent A (0.1% acetic acid in water) and 85% solvent B (methanol) at a flow rate of 1.5 mL/min for 5-9 minutes (e.g. for fractions comprising mainly CBC and THCA).

According to an alternative or an additional embodiment, fraction separation may be carried out on a HPLC comprising a stationary phase comprising RP-18 end capped column (such as a 250 mm×4.6 mm available from e.g. Merck KGaA, Darmstadt, Germany) with a guard column (e.g. 4 mm×4 mm), and a mobile phase of 15% solvent A (0.1% acetic acid in water) and 85% solvent B (methanol) at a flow rate of 1.5 mL/min for 9-12 minutes (e.g. for fractions comprising mainly CBGA).

According to an alternative or an additional embodiment, fraction separation may be carried out on a HPLC comprising a stationary phase comprising RP-18 end capped column (such as a 250 mm×4.6 mm available from e.g. Merck KGaA, Darmstadt, Germany) with a guard column (e.g. 4 mm×4 mm), and a mobile phase of 15% solvent A (0.1% acetic acid in water) and 85% solvent B (methanol) at a flow rate of 1.5 mL/min for 28-35 minutes (e.g. for fractions comprising mainly THCA).

According to an alternative or an additional embodiment, fractions comprising components (active ingredients) are detectable by a detector operated at 220 nm are collected.

According to an alternative or an additional embodiment, the detector is a diode array detector.

According to an alternative or an additional embodiment, the detector is a DAD-300 detector.

According to a specific embodiment, the conditions for HPLC include, for example, an UltiMate 3000 HPLC system coupled with WPS-3000(T) Autosampler, HPG-3400 pump, and DAD-300 detector, a Purospher RP-18 end capped column (such as a 250 mm×4.6 mm available e.g. from Merck KGaA, Darmstadt, Germany) with a guard column (e.g. 4 mm×4 mm), and a mobile phase of 15% solvent A (0.1% acetic acid in water) and 85% solvent B (methanol) at a flow rate of 1.5 mL/min for 5-9 minutes (e.g. for fractions comprising mainly CBC and THCA).

According to a specific embodiment, the conditions for HPLC include, for example, an UltiMate 3000 HPLC system coupled with WPS-3000(T) Autosampler, HPG-3400 pump, and DAD-300 detector, a Purospher RP-18 end capped column (such as a 250 mm×4.6 mm available e.g. from Merck KGaA, Darmstadt, Germany) with a guard column (e.g. 4 mm×4 mm), and a mobile phase of 15% solvent A (0.1% acetic acid in water) and 85% solvent B (methanol) at a flow rate of 1.5 mL/min for 9-12 minutes (e.g. for fractions comprising mainly CBGA).

According to a specific embodiment, the conditions for HPLC include, for example, an UltiMate 3000 HPLC system coupled with WPS-3000(T) Autosampler, HPG-3400 pump, and DAD-300 detector, a Purospher RP-18 end capped column (such as a 250 mm×4.6 mm available e.g. from Merck KGaA, Darmstadt, Germany) with a guard column (e.g. 4 mm×4 mm), and a mobile phase of 15% solvent A (0.1% acetic acid in water) and 85% solvent B (methanol) at a flow rate of 1.5 mL/min for 28-35 minutes (e.g. for fractions comprising mainly THCA).

The extracts and/or fractions obtained may be tested for cytotoxic activity.

Exemplary methods for testing cytotoxic activity are described herein below as well as in the Examples section which follows.

For testing the effect of the extracts and/or fractions on cytotoxic activity, any in-vivo, in-vitro or ex-vivo assay known in the art for testing cytotoxic activity may be used. For example, cell viability assay on cancer cells (e.g. colon cancer cells) using Alamar Blue, XTT viability assay, Cell sorting (e.g. for annexin V), as discussed in detail in the examples section which follows.

The extracts and/or fractions of the present invention can also be characterized by analytical methods such as, but not limited to, spectroscopic methods such as, but not limited to, ultraviolet-visible spectroscopy ("UV-Vis"), infrared spectroscopy ("IR"), and the like; mass-spectrometry ("MS") methods such as, but not limited to, time-of-flight MS; quadrupole MS; electrospray MS, Fourier-transform MS, Matrix-Assisted Laser Desorption/Ionization ("MALDI"), and the like; chromatographic methods such as, but not limited to, gas-chromatography ("GC"), liquid chromatograph ("LC"), high-performance liquid chromatography ("HPLC"), and the like; and combinations thereof (e.g., GC/MS, LC/MS, HPLC/UV-Vis, and the like), and other analytical methods known to persons of ordinary skill in the art.

According to an alternative or an additional embodiment, the extracts and/or fractions obtained by the methods of some embodiments of the invention are kept frozen, e.g. in a freezer, until further use (e.g. at about −20° C. to −90° C., at about −70° C. to −90° C., e.g. at −80° C.), for any required length of time.

According to an alternative or an additional embodiment, the extracts and/or fractions obtained by the methods of some embodiments of the invention are immediately used (e.g. within a few minutes e.g., up to 30 minutes).

The extracts and/or fractions obtained by the methods of some embodiments of the invention may be used separately. Alternatively, different extracts (e.g. from different plants or from separate extraction procedures) may be pooled together. Likewise, different fractions (from the same extract, from different extracts, from different plants and/or from separate extraction procedures) may be pooled together.

The term "pooled" as used herein refers to collected from the liquid chromatography (e.g. HPLC) either as a single fraction or a plurality of fractions.

According to a specific embodiment, different fractions are obtained from a single extract of Cannabis inflorescence, by subjecting the cannabis extract to liquid chromatography and collecting fractions comprising ingredients that are detectable by a detector operated at 220 nm (as discussed in detail herein above). Thus, for examples, fractions may be obtained at the following retention times when the following conditions are used: HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min: F1 retention time 0-5 minutes, F2 retention time 5-9 minutes, F3 retention time 9-12 minutes, F4 retention time 12-14.5 minutes, F5 retention time 18-20, F6 retention time 24-26, F7 retention time 28-35 minutes, F8 retention time 35-37, F9 retention time 37-40.

According to an alternative or an additional embodiment, at least two, at least three, at least four, at least five, at least six, at least seven, at least eight or more of the fractions may be pooled together, at any combination thereof, as discussed in further detail below.

According to one embodiment, the fraction of some embodiments comprises THCA.

As used herein, the term "THCA" refers to Δ9-tetrahydrocannabinolic acid, the precursor of tetrahydrocannabinol (THC). The term THCA as used herein encompasses native THCA (i.e. originating from the Cannabis plant), or synthetic analogs or derivatives thereof. Any THCA analog may be used in accordance with the present teachings as long as it comprises cytotoxic activity (alone, or as part of the composition discussed herein).

The term "analog" refers to a structural derivative having at least the same cytotoxic activity. The analog may be synthetic or naturally occurring.

Exemplary THCA analogs include, but are not limited to, 11-OH-delta9-THCA-A and 11-Nor-delta9-THCA-A carboxylic acid [as discussed in detail in Guillermo Moreno-Sanz, Critical Review and Novel Therapeutic Perspectives of D9-Tetrahydrocannabinolic Acid A, Cannabis and Cannabinoid Research Volume 1.1, (2016)].

According to an alternative or an additional embodiment, the extracts and/or fractions comprise at least about 5-100% THCA, at least about 5-50% THCA, at least about 10-50% THCA, at least about 20-50% THCA, at least about 20-40% THCA, at least about 30-80% THCA, at least about 75-95% THCA, at least about 80-90% THCA, at least about 80-95% THCA, at least about 80-100% THCA, or at least about 90-100% THCA.

According to an alternative or an additional embodiment, the extracts and/or fractions comprise about 5% THCA, at least about 10% THCA, at least about 15% THCA, at least about 20% THCA, at least about 25% THCA, at least about 30% THCA, at least about 35% THCA, at least about 40% THCA, at least about 45% THCA, at least about 50% THCA, at least about 55% THCA, at least about 60% THCA, at least about 65% THCA, at least about 70% THCA, at least about 75% THCA, at least about 80% THCA, at least about 81% THCA, at least about 82% THCA, at least about 83% THCA, at least about 84% THCA, at least about 85% THCA, at least about 86% THCA, at least about 87% THCA, at least about 88% THCA, at least about 89% THCA, at least about 90% THCA, at least about 91% THCA, at least about 92% THCA, at least about 93% THCA, at least about 94% THCA, at least about 95% THCA, at least about 96% THCA, at least about 97% THCA, at least about 98% THCA, at least about 99% THCA, or about 100% THCA.

According to a specific embodiment, the cannabis extracts or fractions comprise 15% or more THCA.

According to a specific embodiment, the cannabis extracts or fractions comprise 20% or more THCA.

According to a specific embodiment, the cannabis extracts or fractions comprise 25% or more THCA.

According to a specific embodiment, the cannabis extracts or fractions comprise 30% or more THCA.

According to a specific embodiment, the cannabis extracts or fractions comprise 50% or more THCA.

According to a specific embodiment, the cannabis extracts or fractions comprise 75% or more THCA.

According to a specific embodiment, the cannabis extracts or fractions comprise 80% or more THCA.

According to a specific embodiment, the cannabis extracts or fractions comprise 85% or more THCA.

According to a specific embodiment, the cannabis extracts or fractions comprise 95% or more THCA.

According to an alternative or an additional embodiment, the extracts and/or fractions comprise cannabis derived active ingredients other than the THCA.

According to an alternative or an additional embodiment, the extracts and/or fractions comprise at least one of D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the extracts and/or fractions comprise at least two, at least three, at least four, at least five, at least six, at least seven of D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the extracts and/or fractions comprise D-Limonene, β-Caryophyllene, Humulene, malic acid, α-Farnesene, cannabinol (CBN), Δ9-tetrahydrocannabinol (THC), and cannabigerol (CBG).

According to an alternative or an additional embodiment, the extracts and/or fractions comprise THCA and any one, two, three, four, five, six or seven of D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the extracts and/or fractions comprise THCA, D-Limonene, β-Caryophyllene, Humulene, malic acid, α-Farnesene, cannabinol (CBN), Δ9-tetrahydrocannabinol (THC), and cannabigerol (CBG).

According to an alternative or an additional embodiment, any one of D-Limonene, β-Caryophyllene, Humulene, malic acid, α-Farnesene, cannabinol (CBN), Δ9-tetrahydrocannabinol (THC), and/or cannabigerol (CBG) may be provided as a synthetic analog.

According to an alternative or an additional embodiment, the extracts and/or fractions comprise components as listed in Table 3, herein below.

According to an alternative or an additional embodiment, the extracts and/or fractions of some embodiments of the invention comprise at least one, two, three, four, five, six, seven, eight, nine, ten or more components as listed in Table 3.

According to an alternative or an additional embodiment, the extracts and/or fractions of some embodiments of the invention comprise THCA as well as at least one, two, three, four, five, six, seven, eight, nine, ten or more components as listed in Table 3.

According to one embodiment, the fraction of some embodiments comprises CBGA.

As used herein, the term "CBGA" refers to cannabigerolic acid, the precursor of THCA, CBDA, and CBCA. The term CBGA as used herein encompasses native CBGA (i.e. originating from the Cannabis plant or synthetic analogs or derivatives thereof. Any CBGA analog may be used in accordance with the present teachings as long as it comprises a cytotoxic activity (alone, or as part of the composition discussed herein).

An exemplary CBGA analog includes, but is not limited to, CBGVA.

According to an alternative or an additional embodiment, the extracts and/or fractions comprise at least about 75-95% CBGA, at least about 80-90% CBGA, at least about 80-95% CBGA, at least about 80-100% CBGA, or at least about 90-100% CBGA.

According to an alternative or an additional embodiment, the extracts and/or fractions comprise at least about 60% CBGA, at least about 65% CBGA, at least about 70% CBGA, at least about 75% CBGA, at least about 80% CBGA, at least about 81% CBGA, at least about 82% CBGA, at least about 83% CBGA, at least about 84% CBGA, at least about 85% CBGA, at least about 86% CBGA, at least about 87% CBGA, at least about 88% CBGA, at least about 89% CBGA, at least about 90% CBGA, at least about 91% CBGA, at least about 92% CBGA, at least about 93% CBGA, at least about 94% CBGA, at least about 95% CBGA, at least about 96% CBGA, at least about 97% CBGA, at least about 98% CBGA, at least about 99% CBGA, or about 100% CBGA.

According to a specific embodiment, the cannabis extracts or fractions comprise 75% or more CBGA.

According to a specific embodiment, the cannabis extracts or fractions comprise 80% or more CBGA.

According to a specific embodiment, the cannabis extracts or fractions comprise 85% or more CBGA.

According to a specific embodiment, the cannabis extracts or fractions comprise 95% or more CBGA.

According to an alternative or an additional embodiment, the extracts and/or fractions comprise cannabis derived active ingredients other than the CBGA.

According to an alternative or an additional embodiment, the extracts and/or fractions comprise at least one of Aromadendrene, Epicedrol, alpha-Bisabolol, Lupeol, CBCA and/or CBN.

According to an alternative or an additional embodiment, the extracts and/or fractions comprise at least two, at least three, at least four, at least five, at least six, at least seven of Aromadendrene, Epicedrol, alpha-Bisabolol, Lupeol, CBCA and/or CBN.

According to an alternative or an additional embodiment, the extracts and/or fractions comprise Aromadendrene, Epicedrol, alpha-Bisabolol, Lupeol, CBCA and CBN.

According to an alternative or an additional embodiment, the extracts and/or fractions comprise CBGA and any one, two, three, four, five, six or seven of Aromadendrene, Epicedrol, alpha-Bisabolol, Lupeol, CBCA and/or CBN.

According to an alternative or an additional embodiment, the extracts and/or fractions comprise CBGA, Aromadendrene, Epicedrol, alpha-Bisabolol, Lupeol, CBCA and CBN.

According to an alternative or an additional embodiment, any one of Aromadendrene, Epicedrol, alpha-Bisabolol, Lupeol, CBCA and CBN may be provided as a synthetic analog.

According to an alternative or an additional embodiment, the extracts and/or fractions comprise components as listed in Table 2, herein below.

According to an alternative or an additional embodiment, the extracts and/or fractions of some embodiments of the invention comprise at least one, two, three, four, five, six, seven, eight, nine, ten or more components as listed in Table 2, herein below.

According to an alternative or an additional embodiment, the extracts and/or fractions of some embodiments of the invention comprise CBGA as well as at least one, two, three, four, five, six, seven, eight, nine, ten or more components as listed in Table 2, herein below.

According to an alternative or an additional embodiment, the extracts and/or fractions comprise CBGA, THCA and any one, two, three, four, five, six or seven of Aromadendrene, Epicedrol, alpha-Bisabolol, Lupeol, CBCA, CBN, D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the extracts and/or fractions comprise CBGA, THCA, Aromadendrene, Epicedrol, alpha-Bisabolol, Lupeol, CBCA, CBN, D-Limonene, β-Caryophyllene, Humulene, malic acid, α-Farnesene, cannabinol (CBN), Δ9-tetrahydrocannabinol (THC), and cannabigerol (CBG).

According to an alternative or an additional embodiment, the extracts and/or fractions of some embodiments of the invention comprise CBGA, THCA as well as at least one, two, three, four, five, six, seven, eight, nine, ten or more components as listed in Table 2 or 3, herein below.

According to an alternative or an additional embodiment, the extracts and/or fractions comprise CBGA to THCA a ratio of 1:1.

According to an alternative or an additional embodiment, the extracts and/or fractions comprise CBGA to THCA ratio higher than 1:1.

According to an alternative or an additional embodiment, the extracts and/or fractions comprise CBGA to THCA ratio of 1:1-1.5:1 (THCA:CBGA).

According to one embodiment, the fraction of some embodiments comprises CBC.

As used herein, the term "CBC" refers to Cannabichromene. The term CBC as used herein encompasses native CBC (i.e. originating from the Cannabis plant), or synthetic analogs or derivatives thereof. Any CBC analog may be used in accordance with the present teachings as long as it comprises a cytotoxic activity (alone, or as part of the composition discussed herein).

According to an alternative or an additional embodiment, the extracts and/or fractions comprise at least about 5-60% CBC, at least about 5-50% CBC, at least about 10-50% CBC, at least about 20-50% CBC, or at least about 20-40% CBC.

According to an alternative or an additional embodiment, the extracts and/or fractions comprise at least about 5% CBC, at least about 10% CBC, at least about 15% CBC, at least about 20% CBC, at least about 25% CBC, at least about 30% CBC, at least about 35% CBC, at least about 40% CBC, at least about 45% CBC, at least about 50% CBC, at least about 55% CBC, at least about 60% CBC, at least about 65% CBC, at least about 70% CBC, at least about 75% CBC, at least about 80% CBC, at least about 85% CBC, at least about 90% CBC, at least about 95% CBC, at least about 99% CBC, or about 100% CBC.

According to a specific embodiment, the cannabis extracts or fractions comprise 15% or more CBC.

According to a specific embodiment, the cannabis extracts or fractions comprise 20% or more CBC.

According to a specific embodiment, the cannabis extracts or fractions comprise 25% or more CBC.

According to a specific embodiment, the cannabis extracts or fractions comprise 30% or more CBC.

According to an alternative or an additional embodiment, the extracts and/or fractions comprise cannabis derived active ingredients other than the CBC.

According to an alternative or an additional embodiment, the extracts and/or fractions comprise cannabis derived active ingredients other than the THCA.

According to an alternative or an additional embodiment, the extracts and/or fractions comprise at least about 10-40% cannabichromene (CBC) and at least about 10-40% tetrahydrocannabinolic acid (THCA).

According to an alternative or an additional embodiment, the extracts and/or fractions comprise at least one of Tumerone and/or Cystine.

According to an alternative or an additional embodiment, the extracts and/or fractions comprise Tumerone and Cystine.

According to an alternative or an additional embodiment, the extracts and/or fractions comprise CBC, THCA and at least one of Tumerone and/or Cystine.

According to an alternative or an additional embodiment, the extracts and/or fractions comprise at least one of CBC, THCA, Tumerone and/or Cystine.

According to an alternative or an additional embodiment, Tumerone and/or Cystine may be provided as a synthetic analog.

According to an alternative or an additional embodiment, the extracts and/or fractions comprise CBC to THCA a ratio of 1:1.

According to an alternative or an additional embodiment, the extracts and/or fractions comprise CBC to THCA ratio higher than 1:1.

According to an alternative or an additional embodiment, the extracts and/or fractions comprise CBC to THCA ratio of 1:3 (CBC:THCA).

According to an alternative or an additional embodiment, the extracts and/or fractions of some embodiments of the invention comprise CBC, THCA as well as at least one, two, three, four, five, six, seven, eight, nine, ten or more components as listed in Table 3, herein below.

According to an alternative or an additional embodiment, the extracts and/or fractions of some embodiments of the invention comprise CBC, THCA, Tumerone and/or Cystine, as well as at least one, two, three, four, five, six, seven, eight, nine, ten or more components as listed in Table 3, herein below.

According to an alternative or an additional embodiment, the extracts and/or fractions of some embodiments of the invention comprise CBC, THCA and at least one of Tumerone, Cystine, D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the extracts and/or fractions comprise at least two, at least three, at least four, at least five, at least six, at least seven or more of Tumerone, Cystine, D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the extracts and/or fractions of some embodiments of the invention comprise CBC, THCA, Tumerone, Cystine, D-Limonene, β-Caryophyllene, Humulene, malic acid, α-Farnesene, cannabinol (CBN), Δ9-tetrahydrocannabinol (THC), and cannabigerol (CBG).

According to an alternative or an additional embodiment, the extracts and/or fractions of some embodiments of the invention comprise CBC, THCA, CBGA, as well as at least one, two, three, four, five, six, seven, eight, nine, ten or more components as listed in Tables 2 or 3, herein below.

According to an alternative or an additional embodiment, the extracts and/or fractions of some embodiments of the invention comprise CBC, THCA, CBGA, Tumerone and/or Cystine, as well as at least one, two, three, four, five, six, seven, eight, nine, ten or more components as listed in Tables 2 or 3, herein below.

According to an alternative or an additional embodiment, the extracts and/or fractions comprise CBC, THCA, CBGA, and any one, two, three, four, five, six or seven or more of Tumerone, Cystine, Aromadendrene, Epicedrol, alpha-Bisabolol, Lupeol, CBCA, CBN, D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the extracts and/or fractions comprise CBC, THCA, CBGA, Tumerone, Cystine, Aromadendrene, Epicedrol, alpha-Bisabolol, Lupeol, CBCA, CBN, D-Limonene, β-Caryophyllene, Humulene, malic acid, α-Farnesene, cannabinol (CBN), Δ9-tetrahydrocannabinol (THC), and cannabigerol (CBG).

The present invention is also directed to a product prepared by the process of the present invention. In some embodiments, there is provided a cytotoxic composition obtainable by the method of some embodiments of the invention.

According to an aspect of the invention, there is provided a composition comprising liquid chromatography pooled fractions of cannabis extract comprising active ingredients detectable by a detector operated at 220 nm, the active ingredients comprising CBC and THCA.

According to an aspect of the invention, there is provided a composition comprising liquid chromatography-purified cannabis extract obtainable by subjecting the cannabis extract to high pressure liquid chromatography (HPLC) and collecting fractions detectable by a detector operated at 220 nm, wherein the HPLC comprises a stationary phase comprising RP-18 end capped column, and a mobile phase of 15% solvent A (0.1% acetic acid in water) and 85% solvent B (methanol) at a flow rate of 1.5 mL/min for 5-9 minutes (e.g. for fractions comprising mainly CBC and THCA).

According to an aspect of the invention, there is provided a composition comprising liquid chromatography-purified cannabis extract obtainable by subjecting the cannabis extract to high pressure liquid chromatography (HPLC) and collecting fractions detectable by a detector operated at 220 nm, wherein conditions for the HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min for 5-9 minutes (e.g. for fractions comprising mainly CBC and THCA).

According to an aspect of the invention, there is provided a composition comprising liquid chromatography pooled fractions of cannabis extract comprising active ingredients detectable by a detector operated at 220 nm, the active ingredients comprising CBC and THCA, the composition being characterized by having a cytotoxic activity on cancer cells.

According to an alternative or an additional embodiment, the composition comprises THCA (e.g. as an active ingredient).

According to an alternative or an additional embodiment, the composition comprises at least about 5-100% THCA, at least about 5-50% THCA, at least about 10-50% THCA, at least about 20-50% THCA, at least about 20-40% THCA, at least about 30-80% THCA, at least about 75-95% THCA, at least about 80-90% THCA, at least about 80-95% THCA, at least about 80-100% THCA, or at least about 90-100% THCA.

According to an alternative or an additional embodiment, the composition comprises about 5% THCA, at least about 10% THCA, at least about 15% THCA, at least about 20% THCA, at least about 25% THCA, at least about 30% THCA, at least about 35% THCA, at least about 40% THCA, at least about 45% THCA, at least about 50% THCA, at least about 55% THCA, at least about 60% THCA, at least about 65% THCA, at least about 70% THCA, at least about 75% THCA, at least about 80% THCA, at least about 81% THCA, at least about 82% THCA, at least about 83% THCA, at least about 84% THCA, at least about 85% THCA, at least about 86% THCA, at least about 87% THCA, at least about 88% THCA, at least about 89% THCA, at least about 90% THCA, at least about 91% THCA, at least about 92% THCA, at least about 93% THCA, at least about 94% THCA, at least about 95% THCA, at least about 96% THCA, at least about 97% THCA, at least about 98% THCA, at least about 99% THCA, or about 100% THCA.

According to a specific embodiment, the composition comprises 15% or more THCA.

According to a specific embodiment, the composition comprises 20% or more THCA.

According to a specific embodiment, the composition comprises 25% or more THCA.

According to a specific embodiment, the composition comprises 30% or more THCA.

According to a specific embodiment, the composition comprises 50% or more THCA.

According to a specific embodiment, the composition comprises 75% or more THCA.

According to a specific embodiment, the composition comprises 80% or more THCA.

According to a specific embodiment, the composition comprises 85% or more THCA.

According to a specific embodiment, the composition comprises 95% or more THCA.

According to an alternative or an additional embodiment, the composition comprising THCA (as an active ingredient)

may comprise a dose range of THCA of 0.1-1000 mg/ml, 0.1-100 mg/ml, 0.1-50 mg/ml, 0.1-10 mg/ml, 0.1-5 mg/ml, 0.1-2.5 mg/ml, 0.1-1 mg/ml, 0.2-2000 mg/ml, 0.2-200 mg/ml, 0.2-20 mg/ml, 0.2-2 mg/ml, 1-1000 mg/ml, 10-100 mg/ml, 10-50 mg/ml, 2-2000 mg/ml, 20-200 mg/ml, 20-100 mg/ml, e.g. 20-30 mg/ml or e.g. 0.2-0.7 mg/ml.

According to an alternative or an additional embodiment, the composition comprises THCA at a range of 5-100 mg/ml/gr of fresh Cannabis, e.g. 20-30 mg/ml mg/ml/gr of fresh Cannabis.

According to an alternative or an additional embodiment, the composition comprises CBC (e.g. as an active ingredient).

According to an alternative or an additional embodiment, the composition comprises at least about 5-60% CBC, at least about 5-50% CBC, at least about 10-50% CBC, at least about 20-50% CBC, or at least about 20-40% CBC.

According to an alternative or an additional embodiment, the composition comprises at least about 5% CBC, at least about 10% CBC, at least about 15% CBC, at least about 20% CBC, at least about 25% CBC, at least about 30% CBC, at least about 35% CBC, at least about 40% CBC, at least about 45% CBC, at least about 50% CBC, at least about 55% CBC, at least about 60% CBC, at least about 65% CBC, at least about 70% CBC, at least about 75% CBC, at least about 80% CBC, at least about 85% CBC, at least about 90% CBC, at least about 95% CBC, at least about 99% CBC, or about 100% CBC.

According to a specific embodiment, the composition comprises 15% or more CBC.

According to a specific embodiment, the composition comprises 20% or more CBC.

According to a specific embodiment, the composition comprises 25% or more CBC.

According to a specific embodiment, the composition comprises 30% or more CBC.

According to an alternative or an additional embodiment, the composition comprises CBC to THCA a ratio of 1:1.

According to an alternative or an additional embodiment, the composition comprises CBC to THCA ratio higher than 1:1.

According to an alternative or an additional embodiment, the composition comprises CBC to THCA ratio of 1:3 (CBC:THCA)

According to an alternative or an additional embodiment, the composition comprises cannabis derived active ingredients other than the THCA and CBC.

According to an alternative or an additional embodiment, the composition comprises CBC, THCA as well as at least one, two, three, four, five, six, seven, eight, nine, ten or more components as listed in Table 3, herein below.

According to an alternative or an additional embodiment, the composition comprises CBC, THCA, Tumerone and/or Cystine, as well as at least one, two, three, four, five, six, seven, eight, nine, ten or more components as listed in Table 3, herein below.

According to an alternative or an additional embodiment, the composition comprises CBC, THCA and at least one of Tumerone, Cystine, D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the composition comprises at least two, at least three, at least four, at least five, at least six, at least seven or more of Tumerone, Cystine, D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the composition comprises CBC, THCA, Tumerone, Cystine, D-Limonene, β-Caryophyllene, Humulene, malic acid, α-Farnesene, cannabinol (CBN), Δ9-tetrahydrocannabinol (THC), and cannabigerol (CBG).

According to an alternative or an additional embodiment, the composition comprises CBC, THCA, CBGA, as well as at least one, two, three, four, five, six, seven, eight, nine, ten or more components as listed in Tables 2 or 3, herein below.

According to an alternative or an additional embodiment, the composition comprises CBC, THCA, CBGA, Tumerone and/or Cystine, as well as at least one, two, three, four, five, six, seven, eight, nine, ten or more components as listed in Tables 2 or 3, herein below.

According to an alternative or an additional embodiment, the composition comprises CBC, THCA, CBGA, and any one, two, three, four, five, six or seven or more of Tumerone, Cystine, Aromadendrene, Epicedrol, alpha-Bisabolol, Lupeol, CBCA, CBN, D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the composition comprises CBC, THCA, CBGA, Tumerone, Cystine, Aromadendrene, Epicedrol, alpha-Bisabolol, Lupeol, CBCA, CBN, D-Limonene, β-Caryophyllene, Humulene, malic acid, α-Farnesene, cannabinol (CBN), Δ9-tetrahydrocannabinol (THC), and cannabigerol (CBG).

According to an aspect of the invention, there is provided a composition comprising liquid chromatography pooled fraction of a cannabis extract comprising active ingredients detectable by a detector operated at 220 nm, the active ingredients comprising CBGA.

According to an aspect of the invention, there is provided a composition comprising liquid chromatography-purified cannabis extract obtainable by subjecting the cannabis extract to high pressure liquid chromatography (HPLC) and collecting fractions detectable by a detector operated at 220 nm, wherein the HPLC comprises a stationary phase comprising RP-18 end capped column, and a mobile phase of 15% solvent A (0.1% acetic acid in water) and 85% solvent B (methanol) at a flow rate of 1.5 mL/min for 9-12 minutes (e.g. for fractions comprising mainly CBGA).

According to an aspect of the invention, there is provided a composition liquid chromatography-purified cannabis extract obtainable by subjecting the cannabis extract to high pressure liquid chromatography (HPLC) and collecting fractions detectable by a detector operated at 220 nm, wherein conditions for the HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min for 9-12 minutes (e.g. for fractions comprising mainly CBGA).

According to an alternative or an additional embodiment, the composition comprises CBGA (e.g. as an active ingredient).

According to an alternative or an additional embodiment, the composition comprises at least about 75-95% CBGA, at least about 80-90% CBGA, at least about 80-95% CBGA, at least about 80-100% CBGA, or at least about 90-100% CBGA.

According to an alternative or an additional embodiment, the composition comprises at least about 60% CBGA, at least about 65% CBGA, at least about 70% CBGA, at least about 75% CBGA, at least about 80% CBGA, at least about 81% CBGA, at least about 82% CBGA, at least about 83% CBGA, at least about 84% CBGA, at least about 85% CBGA, at least about 86% CBGA, at least about 87% CBGA, at least about 88% CBGA, at least about 89% CBGA, at least about 90% CBGA, at least about 91% CBGA, at least about 92% CBGA, at least about 93% CBGA, at least about 94% CBGA, at least about 95% CBGA, at least about 96% CBGA, at least about 97% CBGA, at least about 98% CBGA, at least about 99% CBGA, or about 100% CBGA.

According to a specific embodiment, the composition comprises 75% or more CBGA.

According to a specific embodiment, the composition comprises 80% or more CBGA.

According to a specific embodiment, the composition comprises 85% or more CBGA.

According to a specific embodiment, the composition comprises 95% or more CBGA.

According to an alternative or an additional embodiment, the composition comprising CBGA (as an active ingredient) may comprise a dose range of CBGA of 0.1-1000 mg/ml, 0.1-100 mg/ml, 0.1-50 mg/ml, 0.1-10 mg/ml, 0.1-5 mg/ml, 0.1-2.5 mg/ml, 0.1-1 mg/ml, 1-1000 mg/ml, 1-100 mg/ml, 1-50 mg/ml, e.g. 3-40 mg/ml, e.g. 4 mg/ml.

According to an alternative or an additional embodiment, the composition comprises CBGA at a range of 0.4-40 mg/ml/gr of fresh Cannabis, e.g. 3.5-4 mg/ml/gr of fresh cannabis.

According to an alternative or an additional embodiment, the composition comprises cannabis derived active ingredients other than the CBGA.

According to an alternative or an additional embodiment, the composition comprises (as active ingredients) CBGA and THCA.

According to an alternative or an additional embodiment, the composition comprises CBGA and THCA at a ratio of 1:1.

According to an alternative or an additional embodiment, the composition comprises CBGA and THCA at ratio higher than 1:1.

According to an alternative or an additional embodiment, the composition comprises THCA to CBGA ratio of 1-1.5:1-4.5 (THCA:CBGA).

According to an alternative or an additional embodiment, the composition comprises at least one of Aromadendrene, Epicedrol, alpha-Bisabolol, Lupeol, CBCA and/or CBN.

According to an alternative or an additional embodiment, the composition comprises at least two, at least three, at least four, at least five, at least six, at least seven of Aromadendrene, Epicedrol, alpha-Bisabolol, Lupeol, CBCA and/or CBN.

According to an alternative or an additional embodiment, the composition comprises Aromadendrene, Epicedrol, alpha-Bisabolol, Lupeol, CBCA and CBN.

According to an alternative or an additional embodiment, the composition comprises CBGA and any one, two, three, four, five, six or seven of Aromadendrene, Epicedrol, alpha-Bisabolol, Lupeol, CBCA and/or CBN.

According to an alternative or an additional embodiment, the composition comprises CBGA, Aromadendrene, Epicedrol, alpha-Bisabolol, Lupeol, CBCA and CBN.

According to an alternative or an additional embodiment, the composition comprises components as listed in Table 2, herein below.

According to an alternative or an additional embodiment, the composition comprises at least one, two, three, four, five, six, seven, eight, nine, ten or more components as listed in Table 2, herein below.

According to an alternative or an additional embodiment, the composition comprises CBGA as well as at least one, two, three, four, five, six, seven, eight, nine, ten or more components as listed in Table 2, herein below.

According to an alternative or an additional embodiment, the composition comprises CBGA, THCA and any one, two, three, four, five, six or seven of Aromadendrene, Epicedrol, alpha-Bisabolol, Lupeol, CBCA, CBN, D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the composition comprises CBGA, THCA, Aromadendrene, Epicedrol, alpha-Bisabolol, Lupeol, CBCA, CBN, D-Limonene, β-Caryophyllene, Humulene, malic acid, α-Farnesene, cannabinol (CBN), Δ9-tetrahydrocannabinol (THC), and cannabigerol (CBG).

According to an alternative or an additional embodiment, the composition comprises CBGA, THCA as well as at least one, two, three, four, five, six, seven, eight, nine, ten or more components as listed in Table 2 or 3, herein below.

According to aspect of the invention, there is provided a composition comprising THCA and CBGA, wherein the composition is devoid of at least one of cannabichromene (CBC), cannabidiolic acid (CBDA), and/or cannabidiol (CBD).

According to aspect of the invention, there is provided a composition comprising CBC and THCA, wherein the composition is devoid of at least one of cannabidiolic acid (CBDA), cannabichromenic acid (CBCA), cannabigerolic acid (CBGA).

According to an alternative or an additional embodiment, the different components (e.g. THCA, CBC and/or CBD) are discrete i.e. not comprised in the same fraction.

According to an alternative or an additional embodiment, the fractions are combined into a single composition.

According to an alternative or an additional embodiment, the fractions are comprised in different formulations/compositions.

According to an alternative or an additional embodiment, the composition comprising THCA and CBGA (as active ingredients) may comprise the dose ranges of THCA and CBGA as discussed above.

According to an alternative or an additional embodiment, the composition comprising CBC and THCA (as active ingredients) may comprise a dose range of CBC and THCA as discussed above.

Since the extracts of the present invention, active fractions derived therefrom, and compositions comprising same have cytotoxic activity, they may be used for treating malignant diseases.

Thus, according to one aspect of the present invention, there is provided a method of treating a malignant disease in a subject in need thereof, the method comprising administering to the subject a therapeutically effective amount of the composition of some embodiments of the invention, thereby treating the malignant disease in the subject.

According to one aspect of the present invention, there is provided a therapeutically effective amount of the composition of some embodiments of the invention for use in treating a malignant disease in a subject in need thereof.

According to one aspect of the present invention, there is provided a method of treating a malignant disease in a subject in need thereof, the method comprising administering to the subject a therapeutically effective amount of a first liquid chromatography fraction of a cannabis extract comprising at least 75% tetrahydrocannabinolic acid (THCA), and a therapeutically effective amount of a second liquid chromatography fraction of a cannabis extract comprising at least 75% cannabigerolic acid (CBGA), wherein the first liquid chromatography fraction comprises cannabis derived active ingredients other than the THCA, and the second liquid chromatography fraction comprises cannabis derived active ingredients other than the CBGA, thereby treating the malignant disease in the subject.

According to one aspect of the present invention, there is provided a therapeutically effective amount of a first liquid chromatography fraction of a cannabis extract comprising at least 75% tetrahydrocannabinolic acid (THCA), and a therapeutically effective amount of a second liquid chromatography fraction of a cannabis extract comprising at least 75% cannabigerolic acid (CBGA), wherein the first liquid chromatography fraction comprises cannabis derived active ingredients other than the THCA, and the second liquid chromatography fraction comprises cannabis derived active ingredients other than the CBGA, for use in treating a malignant disease in a subject in need thereof.

According to one aspect of the present invention, there is provided a method of treating a malignant disease in a subject in need thereof, the method comprising administering to the subject a therapeutically effective amount of a liquid chromatography fraction of a cannabis extract comprising at least 20% cannabichromene (CBC) and at least 20% tetrahydrocannabinolic acid (THCA), wherein the fraction comprises cannabis derived active ingredients other than the CBC and the THCA, thereby treating the malignant disease in the subject.

According to one aspect of the present invention, there is provided a therapeutically effective amount of a liquid chromatography fraction of a cannabis extract comprising at least 20% cannabichromene (CBC) and at least 20% tetrahydrocannabinolic acid (THCA), wherein the fraction comprises cannabis derived active ingredients other than the CBC and the THCA, for use in treating a malignant disease in a subject in need thereof.

According to one aspect of the present invention, there is provided a method of treating a malignant disease in a subject in need thereof, the method comprising administering to the subject a therapeutically effective amount of a first liquid chromatography fraction of a cannabis extract comprising at least 75% tetrahydrocannabinolic acid (THCA), and a therapeutically effective amount of a second liquid chromatography fraction of a cannabis extract comprising at least 20% cannabichromene (CBC) and at least 20% tetrahydrocannabinolic acid (THCA), wherein the first liquid chromatography fraction comprises cannabis derived active ingredients other than the THCA, and the second liquid chromatography fraction comprises cannabis derived active ingredients other than the CBC and the THCA, thereby treating the malignant disease in the subject.

According to one aspect of the present invention, there is provided a therapeutically effective amount of a first liquid chromatography fraction of a cannabis extract comprising at least 75% tetrahydrocannabinolic acid (THCA), and a therapeutically effective amount of a second liquid chromatography fraction of a cannabis extract comprising at least 20% cannabichromene (CBC) and at least 20% tetrahydrocannabinolic acid (THCA), wherein the first liquid chromatography fraction comprises cannabis derived active ingredients other than the THCA, and the second liquid chromatography fraction comprises cannabis derived active ingredients other than the CBC and the THCA, for use in treating a malignant disease in a subject in need thereof.

According to one aspect of the present invention, there is provided a method of treating a malignant disease in a subject in need thereof, the method comprising administering to the subject a therapeutically effective amount of a cannabis extract comprising at least 75% tetrahydrocannabinolic acid (THCA), wherein the liquid chromatography fraction comprises cannabis derived active ingredients other than the THCA, thereby treating the malignant disease in the subject.

According to one aspect of the present invention, there is provided a therapeutically effective amount of a cannabis extract comprising at least 75% tetrahydrocannabinolic acid (THCA), wherein the liquid chromatography fraction comprises cannabis derived active ingredients other than the THCA, for use in treating a malignant disease in a subject in need thereof.

According to one aspect of the present invention, there is provided a method of treating a malignant disease in a subject in need thereof, the method comprising administering to the subject a therapeutically effective amount of liquid chromatography pooled fractions of cannabis extract comprising active ingredients detectable by a detector operated at 220 nm, wherein the active ingredients comprise THCA and CBGA, thereby treating the malignant disease in the subject.

According to one aspect of the present invention, there is provided a therapeutically effective amount of liquid chromatography pooled fractions of cannabis extract comprising active ingredients detectable by a detector operated at 220 nm, wherein the active ingredients comprise THCA and CBGA, for use in treating a malignant disease in a subject in need thereof.

According to one aspect of the present invention, there is provided a method of treating a malignant disease in a subject in need thereof, the method comprising administering to the subject a therapeutically effective amount of liquid chromatography pooled fractions of cannabis extract comprising active ingredients detectable by a detector operated at 220 nm, wherein the active ingredients comprise CBC and THCA, thereby treating the malignant disease in the subject.

According to one aspect of the present invention, there is provided a therapeutically effective amount of liquid chromatography pooled fractions of cannabis extract comprising active ingredients detectable by a detector operated at 220 nm, wherein the active ingredients comprise CBC and THCA, for use in treating a malignant disease in a subject in need thereof.

According to one aspect of the present invention, there is provided a method of treating a malignant disease in a subject in need thereof, the method comprising administering to the subject a therapeutically effective amount of liquid chromatography pooled fractions of cannabis extract comprising active ingredients detectable by a detector operated at 220 nm, wherein the active ingredients comprise THCA, thereby treating the malignant disease in the subject.

According to one aspect of the present invention, there is provided a therapeutically effective amount of liquid chromatography pooled fractions of cannabis extract comprising active ingredients detectable by a detector operated at 220 nm, wherein the active ingredients comprise THCA, for use in treating a malignant disease in a subject in need thereof.

According to one aspect of the present invention, there is provided a method of treating a malignant disease in a subject in need thereof, the method comprising administering to the subject a therapeutically effective amount of a composition comprising THCA and CBGA, wherein the composition is devoid of at least one of cannabichromene (CBC), cannabidiolic acid (CBDA), and/or cannabidiol (CBD), thereby treating the malignant disease in the subject.

According to one aspect of the present invention, there is provided a therapeutically effective amount of a composition comprising THCA and CBGA, wherein the composition is devoid of at least one of cannabichromene (CBC), cannabidiolic acid (CBDA), and/or cannabidiol (CBD), for use in treating a malignant disease in a subject in need thereof.

According to one aspect of the present invention, there is provided a method of treating a malignant disease in a subject in need thereof, the method comprising administering to the subject a therapeutically effective amount of a composition comprising at least about 20% THCA and at least about 20% CBGA.

According to one aspect of the present invention, there is provided a therapeutically effective amount of a composition comprising at least about 20% THCA and at least about 20% CBGA, for use in treating a malignant disease in a subject in need thereof.

According to one embodiment, the composition comprises at least about 10%, 20%, 30%, 40%, 50%, 60%, 70%, 80% or 90% THCA and at least about 10% 20%, 30%, 40%, 50%, 60%, 70%, 80% or 90% CBGA.

According to one aspect of the present invention, there is provided a method of treating a malignant disease in a subject in need thereof, the method comprising administering to the subject a therapeutically effective amount of a composition comprising CBC and THCA, wherein the composition is devoid of at least one of cannabidiolic acid (CBDA), cannabichromenic acid (CBCA), cannabigerolic acid (CBGA), thereby treating the malignant disease in the subject.

According to one aspect of the present invention, there is provided a therapeutically effective amount of a composition comprising CBC and THCA, wherein the composition is devoid of at least one of cannabidiolic acid (CBDA), cannabichromenic acid (CBCA), cannabigerolic acid (CBGA), for use in treating a malignant disease in a subject in need thereof.

According to one aspect of the present invention, there is provided a method of treating a malignant disease in a subject in need thereof, the method comprising administering to the subject a therapeutically effective amount of a composition comprising at least about 10% THCA and at least about 10% CBC.

According to one aspect of the present invention, there is provided a therapeutically effective amount of a composition comprising at least about 10% THCA and at least about 10% CBC, for use in treating a malignant disease in a subject in need thereof.

According to one embodiment, the composition comprises at least about 10%, 20%, 30%, 40%, 50%, 60%, 70%, 80% or 90% THCA and at least about 10%, 20%, 30%, 40%, 50%, 60%, 70%, 80% or 90% CBC.

According to an alternative or an additional embodiment, the THCA constitutes at least about 10%, about 20%, about 30%, about 40%, about 50%, about 60%, about 70%, about 75%, about 80%, about 85%, about 90%, about 95%, about 99%, or about 100% of the active ingredients in the composition.

According to an alternative or an additional embodiment, the CBC constitutes at least about 10%, about 20%, about 30%, about 40%, about 50%, about 60%, about 70%, about 75%, about 80%, about 85%, about 90%, about 95%, about 99%, or about 100% of the active ingredients in the composition.

According to an alternative or an additional embodiment, the CBGA constitutes at least about 30%, about 40%, about 50%, about 60%, about 70%, about 75%, about 80%, about 85%, about 90%, about 95%, about 99%, or about 100% of the active ingredients in the composition.

As used herein, the terms "subject" or "subject in need thereof" include mammals, preferably human beings at any age or gender. The subject may be healthy or showing preliminary signs of a pathology, e.g. a malignancy or a pathology associated with the malignancy. This term also encompasses individuals who are at risk to develop the pathology (e.g. malignancy).

As used herein the term "treating" refers to curing, reversing, attenuating, alleviating, minimizing, suppressing or halting the deleterious effects of a disease or disorder (e.g. a malignancy). Those of skill in the art will understand that various methodologies and assays can be used to assess the development of a pathology, and similarly, various methodologies and assays may be used to assess the reduction, remission or regression of a pathology (e.g. a malignancy), as discussed below.

According to a specific embodiment, treating is preventing.

As used herein the terms "malignancy" or "malignant disease" refer to any cancerous disease, also referred to herein as "cancer". Cancer cells may be associated with phenotypes such uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor, such cells may exist locally within an animal (e.g. solid tumor), alternatively, cancer cells may circulate in the blood stream or in the lymphatic system as independent cells, for example, leukemic cells or lymphoma cells, respectively (e.g. non-solid tumor such as a hematologic malignancy), or may be dispersed throughout the body (e.g. metastasis). It will be appreciated that the term cancer as used herein encompasses all types of cancers, at any stage and in any form.

Types of cancerous diseases amenable to treatment by the methods of some embodiments of the invention include benign tumors, warts, polyps, pre-cancers, malignant tumors/cancers and metastasis.

Specific examples of cancerous diseases which can be treated using the methods of the present invention include, but are not limited to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

Pre-cancers are well characterized and known in the art (refer, for example, to Berman J J, and Henson D E., 2003. Classifying the pre-cancers: a metadata approach. *BMC Med Inform Decis Mak.* 3:8). Classes of pre-cancers amenable to treatment via the method of the invention include acquired small or microscopic pre-cancers, acquired large lesions with nuclear atypia, precursor lesions occurring with inherited hyperplastic syndromes that progress to cancer, and acquired diffuse hyperplasias and diffuse metaplasias. Examples of small or microscopic pre-cancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

According to a specific embodiment of this aspect of the present invention, the cancer comprises intestinal cancer, a glioma, a breast cancer, a lung cancer, a prostate cancer, skin cancer, a renal cancer, an ovarian cancer, a head and neck cancer, a fibrosarcoma, a uterine cervix cancer, an esophagus cancer, a rectum cancer, an oral cavity cancer, a liver cancer and a pancreatic cancer.

Each of the compositions of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the cannabis derived active ingredients accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For transdermal administration, the composition can be formulated in a form of a gel, a cream, an ointment, a paste, a lotion, a milk, a suspension, an aerosol, a spray, a foam, a serum, a swab, a pledget, a pad or a patch. Formulations for transdermal delivery can typically include carriers such as water, liquid alcohols, liquid glycols, liquid polyalkylene glycols, liquid esters, liquid amides, liquid protein hydrolysates, liquid alkylated protein hydrolysates, liquid lanolin, lanolin derivatives, glycerin, mineral oil, silicone, petroleum jelly, lanolin, fatty acids, vegetable oils, parabens, waxes, and like materials commonly employed in topical compositions. Various additives, known to those skilled in the art, may be included in the transdermal formulations of the invention. For example, solvents may be used to solubilize certain active ingredients substances. Other optional additives include skin permeation enhancers, opacifiers, antioxidants, gelling agents, thickening agents, stabilizers, and the like.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran.

Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (cannabis derived active ingredients) effective to prevent, alleviate or ameliorate symptoms of a disorder (e.g., IBD) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Animal models for cancer are described for example in Cheon and Orsulic, *Annu. Rev. Pathol.* (2011) 6:95-119 and in Abate-Shen, *Clinic. Cancer. Res.* (2006) 12(18).

According to one embodiment, a therapeutically effective amount of a composition comprising liquid chromatography pooled fractions of cannabis extract comprising active ingredients detectable by a detector operated at 220 nm, wherein the active ingredients comprise THCA, is in the range of 0.1-1000 mg/day/kg, 0.1-100 mg/day/kg, 0.1-50 mg/day/kg, 0.1-10 mg/day/kg, 0.1-5 mg/day/kg, 0.1-2.5 mg/day/kg, 0.1-1 mg/day/kg, 0.2-2000 mg/ml/kg, 0.2-200 mg/ml/kg, 0.2-20 mg/ml/kg, 0.2-2 mg/ml/kg, 1-1000 mg/ml/kg, 10-100 mg/ml/kg, 10-50 mg/ml/kg, 2-2000 mg/ml/kg, 20-200 mg/ml/kg, 20-100 mg/ml/kg, e.g. 20-30 mg/ml/kg or e.g. 0.2-0.7 mg/ml/kg, e.g. 0.7 mg/day/kg.

According to one embodiment, a therapeutically effective amount of a composition comprising liquid chromatography pooled fractions of cannabis extract comprising active ingredients detectable by a detector operated at 220 nm, wherein the active ingredients comprise CBGA, is in the range of 0.11 mg/mL/Kg 0.95 mg/mL/Kg is in the range of 0.1-1000 mg/ml, 0.1-100 mg/ml, 0.1-50 mg/ml, 0.1-10 mg/ml, 0.1-5 mg/ml, 0.1-2.5 mg/ml, 0.1-1 mg/ml, 0.2-2000 mg/ml/kg, 0.2-200 mg/ml/kg, 0.2-20 mg/ml/kg, 0.2-2 mg/ml/kg, 1-1000 mg/ml/kg, 10-100 mg/ml/kg, 10-50 mg/ml/kg, 2-2000 mg/ml/kg, 20-200 mg/ml/kg, 20-100 mg/ml/kg, e.g. 0.1-1 mg/ml/kg.

According to one embodiment, a therapeutically effective amount of a composition comprising liquid chromatography pooled fractions of cannabis extract comprising active ingredients detectable by a detector operated at 220 nm, wherein the active ingredients comprises CBC.

As mentioned, a synergistic cytotoxic affect has been observed when THCA (or compositions comprising same) is administered along with CBGA (or compositions comprising same).

Likewise, a synergistic cytotoxic affect has been observed when THCA (or compositions comprising same) is administered along with CBC (or compositions comprising same).

Thus, according to one embodiment, when the composition comprising THCA as an active ingredient is administered at a dose of 0.7 mg/day/kg, the composition comprising CBGA as an active ingredient is administered at a dose of 0.6 mg/day/kg, i.e. at a relation of 1.2:1 (THCA:CBGA).

According to one embodiment when the composition comprising THCA as an active ingredient is administered at a dose of 0.7 mg/day/kg, the composition comprising CBGA as an active ingredient is administered at a dose of 0.4 mg/day/kg, i.e. at a relation of 1.75:1 (THCA:CBGA).

According to one embodiment when the composition comprising THCA as an active ingredient is administered at a dose of 0.7 mg/day/kg, the composition comprising CBGA as an active ingredient is administered at a dose of 0.3 mg/day/kg, i.e. at a relation of 2.3:1 (THCA:CBGA).

According to one embodiment when the composition comprising THCA as an active ingredient is administered at a dose of 0.7 mg/day/kg, the composition comprising CBGA as an active ingredient is administered at a dose of 0.2 mg/day/kg, i.e. at a relation of 3.5:1 (THCA:CBGA).

According to one embodiment when the composition comprising THCA as an active ingredient is administered at a dose of 0.7 mg/day/kg, the composition comprising CBGA as an active ingredient is administered at a dose of 0.14 mg/day/kg, i.e. at a relation of 5:1 (THCA:CBGA).

According to one embodiment when the composition comprising THCA as an active ingredient is administered at a dose of 0.7 mg/day/kg, the composition comprising CBGA as an active ingredient is administered at a dose of 0.07 mg/day/kg, i.e. at a relation of 10:1 (THCA:CBGA).

According to one embodiment when the composition comprising THCA as an active ingredient is administered at a dose of 0.7 mg/day/kg, the composition comprising CBGA as an active ingredient is administered at a dose of 0.04 mg/day/kg, i.e. at a relation of 17:1 (THCA:CBGA).

According to one embodiment when the composition comprises THCA and CBC as active ingredients, the composition is administered at a dose ratio of CBC to THCA of 1:3 (CBC:THCA).

Such a dosing can be adjusted as long as the relation of THCA:CBGA or THCA:CBC is maintained as described above, a person of skill in the art can make the proper adjustments based on the subject being treated and the level of the components (e.g. THCA, CBGA, CBC) in the composition.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cannabis derived active ingredients (the intestinal tissue) levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to another embodiment, in order to enhance treatment of the malignant disease, the present invention further envisions administering to the subject an additional therapy which may benefit treatment. One of skill in the art is capable of making such a determination.

Thus, for example, the compositions described herein may be administered in conjunction with chemotherapy, radiation therapy, hormonal therapy, targeted therapy, immunotherapy or surgical therapy. Such anti-cancer therapies and methods of utilizing same are well known to one of skill in the art.

Exemplary anti-cancer drugs that can be co-administered with the compounds of the invention include, but are not limited to, Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

Any of the above described agents may be administered individually or in combination.

The cannabis extract of the present invention can be administered to a subject (e.g., a human) in need thereof in a variety of other forms including a nutraceutical composition.

As used herein, a "nutraceutical composition" refers to any substance that may be considered a food or part of a food and provides medical or health benefits, including the prevention and treatment of disease. In some embodiments, a nutraceutical composition is intended to supplement the diet and contains at least one or more of the following ingredients: a vitamin; a mineral; an herb; a botanical; a fruit; a vegetable; an amino acid; or a concentrate, metabolite, constituent, or extract of any of the previously mentioned ingredients; and combinations thereof.

In some embodiments, a nutraceutical composition of the present invention can be administered as a "dietary supplement," as defined by the U.S. Food and Drug Administration, which is a product taken by mouth that contains a "dietary ingredient" such as, but not limited to, a vitamin, a mineral, an herb or other botanical, an amino acid, and substances such as an enzyme, an organ tissue, a glandular, a metabolite, or an extract or concentrate thereof.

Non-limiting forms of nutraceutical compositions of the present invention include: a tablet, a capsule, a pill, a softgel, a gelcap, a liquid, a powder, a solution, a tincture, a suspension, a syrup, or other forms known to persons of skill in the art. A nutraceutical composition can also be in the form of a food, such as, but not limited to, a food bar, a beverage, a food gel, a food additive/supplement, a powder, a syrup, and combinations thereof.

According to another aspect of the invention, there is provided a method of determining a cytotoxic activity of the composition of some embodiments of the invention, the method comprising ex-vivo contacting a malignant tissue of a subject with the composition, wherein an increased cell death in cells of the malignant tissue above a predetermined threshold is indicative of the cytotoxic activity of the composition.

According to another aspect of the invention, there is provided a method of determining a cytotoxic activity of the composition of some embodiments of the invention, the method comprising ex-vivo contacting a malignant tissue of a subject with the composition, wherein a reduced cell proliferation in cells of the malignant tissue below a predetermined threshold is indicative of the cytotoxic activity of the composition.

According to one embodiment, the malignant tissue is a cancer tissue biopsy.

Exemplary tissues include oesophagus, gallbladder, liver, pancreas, stomach, small intestine, bowel (large intestine or colon and rectum), anus, breast, lung, skin and brain tissues.

According to one embodiment, a predetermined threshold can be established by determining normal cell death and cell proliferation by a healthy tissue (e.g. of a healthy donor subject, of the subject before disease onset or during disease remission, or from tissue cultures available commercially).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat.

Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

GENERAL MATERIALS AND EXPERIMENTAL PROCEDURES

Extraction of Cannabis Inflorescence

Fresh flowers of *C. sativa* strain AD were harvested from plants. They were either taken immediately for extraction and frozen at −80° C., or heated (baked) for 2.5-3 hours at 150° C. prior to extraction. Fresh and baked *Cannabis* flowers (2 g) were pulverized with liquid nitrogen. Absolute ethanol was added to each tube containing the powder at a sample-to-absolute ethanol ratio of 1:4 (w/v). The tubes were mixed thoroughly on a shaker for 30 minutes and then the extract was filtered through a filter paper. The filtrate was transferred to new tubes. The solvent was evaporated with a vacuum evaporator. The dried extract was resuspended in 1 mL of absolute methanol and filtered through a 0.45-μm syringe filter. The filtered liquid was collected for the treatments, the resuspended extract was diluted for cell cultures and biopsies in enzyme-linked immunosorbent assay (ELISA) experiments. Sample dry weight was determined by crushing 1 g of plant material with known fresh weight and incubating overnight at 60° C., then weighing again for dry weight calculation.

Chemical Characterization

Standard Preparation

The cannabinoid standards cannabigerol (CBG), cannabidiol (CBD), cannabidiolic acid (CBDA), cannabinol (CBN), cannabigerolic acid (CBGA), tetrahydrocannabinol (THC), cannabichromene (CBC) and tetrahydrocannabinolic acid (THCA) were diluted to 10 ppm concentration with methanol and then subjected to HPLC separation. For quantification of THC and THCA, the standards were dissolved in methanol at different concentrations from 5 ppm to 40 ppm.

Sample Preparation

For HPLC, the dry extract (the ethanol crude) was resuspended in 1 mL methanol and filtered through a 0.45-μm syringe filter (Merck, Darmstadt, Germany). The filtered extract (the filtrate) was diluted 10 times with methanol and then separated by HPLC.

HPLC Separation

Sample separation was carried out in an UltiMate 3000 HPLC system coupled with WPS-3000(T) Autosampler, HPG-3400 pump, and DAD-300 detector. The separation was performed on a Purospher RP-18 end capped column (250 mm×4.6 mm I.D.; Merck KGaA, Darmstadt, Germany) with a guard column (4 mm×4 mm I.D.). Solvent gradients were formed by isocratic proportion with 15% solvent A (0.1% acetic acid in water) and 85% solvent B (methanol) at a flow rate of 1.5 mL/min for 35 min. The compound peaks were detected at 220, 240 and 280 nm. The 220-nm peaks were taken for further processing. The extracts were fractionated into nine fractions according to the obtained chromatogram.

Mass Spectrometry (MS) Analysis

Analysis of the fractions was carried out using ESI (Q-TOF) 6545 (high resolution) (Agilent). The MS conditions were as follows: ESI positive mode, m/z 50-1500, gas temperature 350° C., injection volume 5 μL, solvent composition 0.1% formic acid in water (46%), acetonitrile (50%) and water (4%) (v/v).

Nuclear Magnetic Resonance (NMR) Analysis $^1$H and $^{13}$C spectra were recorded in a Bruker Avance-400 instrument (400.1 and 100.6 MHz, respectively) in $CDCl_3$ as the solvent, containing Tetramethylsilane (TMS) as an internal reference, at 300K. In addition, three 2D experiments were performed: COSY ($^1$H-$^1$H correlation), HMQC (one-bond $^1$H-$^{13}$C correlation) and HMBC (long-range $^1$H-$^{13}$C correlation).

Gas Chromatograph (GC) with Mass Selective Detector (MSD) (GC/MS) Analysis

GC/MS analyses were carried out using a HP7890 gas chromatograph coupled to a HP6973 mass spectrometer with electron multiplier potential 2 KV, filament current 0.35 mA, electron energy 70 eV, and the spectra were recorded over the range m/z 40 to 400. An Agilent 7683 autosampler was used for sample introduction. Helium was used as a carrier gas at a constant flow of 1.1 ml s-1. One μl of each sample was injected to the GC/MS using a 1:10 split ratio injection mode. An isothermal hold at 50° C. was kept for 2 minutes, followed by a heating gradient of 6° C. min-1 to 300° C., with the final temperature held for 4 minutes. A 30 m, 0.25 mm ID 5% cross-linked phenylmethyl siloxane capillary column (HP-5MS) with a 0.25 μm film thickness was used for separation and the injection port temperature was 220° C. The MS interface temperature was 280° C. Peak assignments were carried out with the aid of library spectra (NIST 14.0) and compared with published data and MS data obtained from the injection of standards purchased from Sigma-Aldrich.

Cell Cultures

HCT116 (ATCC CCL-247), HT29 (ATCC HTB-38), CaCO2 (ATCC HTB-37) and CCD-112CoN (ATCC CRL-1541) colon cells were grown at 37° C. in a humidified 5% $CO_2$-95% air atmosphere. Cells were maintained in McCoy's 5a Modified Medium, DMEM Medium (for CaCO2 cells) and EMEM medium (for CCD-112CoN cell line).

Breast cancer cell line MDA-MB231 and glioblastoma cell line A172 were grown at 37° C. in a humidified 5% $CO_2$-95% air atmosphere. Cells were maintained in DMEM medium.

Determination of Extracts and Compounds Cytotoxic Activity in Cell Lines

Resazurin (Alamar blue, R&D Systems, Minneapolis, USA) was used to check the cytotoxic effect of extracts. For this, 10% Resazurin was added to each well of the treatments and incubated for 4 hours at 37° C. in a humidified 5% $CO_2$-95% air atmosphere. Supernatant (100 µL from each well) was transferred to a 96-well plate and the relative fluorescence at the excitation/emission of 544/590 nm was measured. Percentage of live cells was calculated relative to the non-treated control after reducing the auto fluorescence of Alamar Blue without cells. Dose-effect curves of *C. sativa* ethanol extracts of fresh inflorescences (C2F), heated inflorescences (C2B) for HCT116 colon cancer cells and CCD18 colon healthy cells were determined. HCT116 and CCD18 cells were seeded (10,000 per well) in triplicate in 100 µL growing media and incubated for 24 hours at 37° C. in a humidified 5% $CO_2$-95% air atmosphere. Cells were treated with C2F, C2B at different dilutions (35 µg/mL to 1600 µg/mL) along with 50 ng/mL TNF-0, for 16 hours. Next, the cells viability was determined with Alamar Blue. GraphPad Prism was employed to produce dose-response curve and $IC_{50}$ doses of C2F and C2B.

XTT Viability

Cells were seeded into a 96-well plates at 10,000 cells per well in triplicate in normal growing media. The following day, media was replaced with normal growing media containing plant extracts/fractions, standards (THCA and CBGA) or media only for control (all concentrations of the different treatments are indicated in the figures). Cells were incubated for 48 hours then XTT (2,3,-bis(2-methoxy-4-nitro-5-sulfophenyl)-5-[(phenylamine)-carbonyl]-2H-tetrazolium inner salt) reduction was used to quantify viability according to manufacturer's instruction (BI, Kibbutz Beit-Haemek, Israel). Cells were incubated with XTT reagent for 2 hours at 37° C. in a humidified 5% $CO_2$-95% air atmosphere. Absorbance was recorded by a photometer SPEKTRA Fluor Plus (Tecan, Salzburg, Austria) at 490 nm with 650 nm of reference wavelength. Cell survival was estimated from the equation: % cell survival=100×(At−Ac)(treatment)/(At−Ac)(control); At and Ac are the absorbencies (490 nm) of the XTT colorimetric reaction (BI, Kibbutz Beit-Haemek, Israel) in treated and control cultures, respectively, minus non-specific absorption that was measured at 650 nm. Absorbance of medium alone was also deducted from specific readings.

Analysis of Combined Effects

In order to examine synergy between F3 and F7 cytotoxic activity, XTT assay was used on HCT116 cells as described above. Different concentrations of F3 (3 µg/mL to 160 µg/mL) with and without $IC_{50}$ dose of F7 (20 µg/mL) or different concentration of F7 (7.9 µg/mL to 380 µg/mL) with and without $IC_{50}$ dose of F3 (36 µg/mL) were used to treat the cells for 48 hours. Next, the cells were incubated with XTT reagent for 2 hours as described above. For standards synergy examination, different concentrations of THCA (4 µg/mL to 50 µg/mL) with and without CBGA (28 µg/mL) or different concentrations of CBGA (6.67 µg/mL to 53.3 µg/mL) with and without THCA (13.14 µg/mL) were used. Drug synergy was determined by the Bliss independence drug interaction model previously described [) (Delaney W E et al., Antimicrob Agents Chemother. (2004) 48:3702-3710] which is defined by the following equation:

$$Exy=Ex+Ey-(ExEy)$$

Where (Exy) is the additive effect of the drug x and y as predicted by their individual effects (Ex and Ey). For calculation purpose, in this paper, the drug's anti-cancer effect was defined as complementary to the obtained results (1-Exy). In case the observed value of Exy is greater than the calculated Exy value, the combination treatment is considered antagonistic. If the observed value is less than the calculated one, then the combination treatment is considered synergistic. If both values are equal, the combination treatment is considered additive (independent).

Annexin V Assay

Apoptosis was assessed using MEBCYTO Apoptosis Kit with Annexin V-FITC and PI (MBL, Enco, 4700). Staining was done according to manufacturer instructions. In brief, cells were seeded in 6-well plate culture dishes, at density of 1×10⁶ cells per well in McCoy's 5a Modified Medium. The following day, the media was replaced with medium containing IC-50 dose of F7 (20 µg/mL), F3 (35 µg/mL) and combination of F7 & F3 along with TNF-α (50 ng/mL) and incubated for 24 and 48 hours at 37° C. in a humidified 5% $CO_2$-95% air atmosphere. After incubation, cells were harvested and collected separately. Then tubes were centrifuged for 10 minutes at 900 g RCF and cell pellets were resuspended and washed twice with 1 mL of PBS. The cells in each sample were counted and if necessary the number of cells was adjusted to a concentration of 2×10⁵ cells in 85 µL of Annexin binding buffer. Cells were stained using 10 µL of Annexin V− FITC solution and 5 µL of propidium iodide (PI) working solution followed by incubation at room temperature for 15 minutes in the dark. Then 400 µL of Annexin V binding buffer were added to each tube and flow cytometry was performed using GALLIOS flow cytometer (FACS). Cells were considered to be apoptotic if they were Annexin V+/PI− (early apoptotic) and Annexin V+/PI+ (late apoptotic). Live cells were Annexin V−/PI− and Annexin V−/PI+ are the necrosis.

Cell Cycle Analysis

Cells were seeded in 6-well plate culture dishes at a density of 1×10⁶ cells per well. After 24 hours of seeding the cell culture media was replaced with starvation media and incubated for 24 hours at 37° C. in a humidified 5% $CO_2$-95% air atmosphere. After 24 hours of incubation, the cells were treated with F7 (20 µg/mL), F3 (36 µg/mL), F7 in combination with F3 and its Solvent control along with TNF-α (50 ng/mL) for another 24 hours. Then the cells from each well were harvested and collected separately and centrifuged for 10 minutes at 900 g. The cells pellet was washed once with 1 ml of PBS and fixed with 70% cold ethanol at 4° C. for 1 hour. Then the fixed cells were pelleted out and washed twice with 1 ml of PBS. The cell pellet was then stained by resuspending in 250 µL of propidium iodide solution (50 µg/ml) containing RNase A (100 µg/ml) for 15 minutes in the dark. Then 400 µl of PBS were added to each tube and the cells were analyzed using GALLIOS flow cytometer.

Culture of Biopsies

Biopsies from polyps and from healthy colonic tissue of the same patient were obtained from 7 patients scheduled for colonoscopy as deemed necessary by their physician, the study was approved by our Institutional Ethical Committee (Helsinki approval no. 0121-16), and all patients gave their written informed consent prior to the colonoscopy. Biopsies taken during colonoscopy were placed in tissue culture media and immediately transported to the laboratory. Upon receiving the biopsies, PBS was replaced with Hank's balanced salt solution and then the samples were centrifuged at 8000 rpm (11,885×g) for 1 minute. Then the supernatant was removed and tissues were washed four times with Hank's balanced salt solution. After each wash, samples were centrifuged as described above. Then the tissues were placed on a small petri dish and cut into 4-5 pieces with a clean scalpel. The pieces were then placed on Millicel hydrophilic PTFE tissue-culture inserts (Millipore, 30 mm, 0.4 µm). The inserts were placed in 6-well plastic tissue-culture dishes (Costar 3506) along with 1.5 mL of tissue-culture medium (Dulbecco's modified Eagle's medium supplemented with 10% v/v heat-inactivated fetal calf serum, 100 U/mL penicillin, 100 µg/mL streptomycin, 50 µg/mL leupeptin, 1 mM PMSF, and 50 µg/mL soybean trypsin inhibitor). This was followed by treating the tissues with extracts, or leaving them untreated (control). For the treatment medium was replaced with medium containing C2F (1.25 mg/mL), F7 (at different concentrations: 100 µg/mL, 125 µg/mL, 250 µg/mL or 400 µg/mL), F3 (75 µg/mL, 107 µg/mL or X µg/mL) or F3+F7 (at the desired concentrations) and incubated overnight at 37° C. in a humidified 5% $CO_2$-95% air atmosphere.

Cell Separation and Resazurin for Biopsies

After 16 hours the treated and untreated tissues from the above section were taken into a tube and washed twice with PBS. Then the tissues were transferred into a petri dish and chopped into very fine pieces using a surgical scalpel. The finely chopped pieces were transferred into tubes and 500 µL of R10 medium (RPMI 1640 supplemented with 10% FBS, 10 mM HEPES, 100 U/mL penicillin, 100 µg/mL streptomycin and 50 µg/mL gentamycin) was added along with 20 IU/mL of DNase, 0.13 units/mL of dispase and 1 mg/mL of collagenase 1 A. Then the tissues were vortexed and incubated at 37° C. for 1 hour by vortexing every 15 minutes in between. Then the cell suspensions were pelleted at 950 g for 10 minutes and washed twice with PBS buffer. The cell suspension pellets were resuspended with 500 µL R10 medium and incubated at 37° C. in a humidified 5% $CO_2$-95% air atmosphere with 10% Resazurin for 4 hours and the supernatant (100 µL from each well) was transferred to a 96-well plate and the relative fluorescence at the excitation/emission of 544/590 nm was measured. Percentage of live cells was calculated relative to the non-treated control after reducing the auto fluorescence of Alamar Blue without cells.

RNA Sequencing and Transcriptome Analysis

For preparation of RNA, cells were seeded into a six-well plate at a concentration of 1,500,000 cell/mL per well. After 24 hours of incubation at 37° C. in a humidified 5% $CO_2$-95% air atmosphere, cells were treated with F3 (36 µg/mL), F7 (20 µg/mL) and combination of F3 with F7 at these concentrations along with TNF-α (50 ng/mL) for 8 hours. Then, cells were harvested and total RNA was extracted using TRI reagent (Sigma-Aldrich) according to the manufacturer's protocol. RNA was kept at −80° C. until further analysis. Sequencing libraries were prepared using the INCPM mRNA Seq protocol. 60 bp single reads were sequenced on 1 lanes of an Illumina hiseq.

For transcriptome analysis the raw-reads were subjected to a filtering and cleaning procedure. The SortMeRNA tool was used to filter out rRNA [Kopylova et al., Bioinformatics (2012) 28(24): 3211-3217]. Then, the FASTX Toolkit (www(dot)hannonlab(dot)cshl(dot)edu/fastx_toolkit/index(dot)html, version 0.0.13.2) was used to trim read-end nucleotides with quality scores <30, using the fastq_quality_trimmer, and to remove reads with less than 70% base pairs with a quality score ≤30 using the Fastq_quality_filter.

Clean-reads were aligned to the human genome extracted from National Center for Biotechnology Information (NCBI) (GRCh38; www(dot)ncbi(dot)nlm(dot)nih.gov/genome/guide/human/) using Tophat2 software (v2.1; Kim D. et al., Genome biology (2013) 14(4): R36). Gene abundance estimation was performed using Cufflinks [v2.2; Trapnell et al., Nat Biotechnol. (2010) 28:511] combined with gene annotations from the NCBI. Heatmap visualization was performed using R Bioconductor [Gentleman, R C. et al., Genome biology (2004) 5(10): R80). Differential expression analysis was done using the edgeR R package [Robinson M D. et al., Bioinformatics (2010) 26(1): 139-140). Genes that varied from the control more than twofold, with an adjusted P-value of no more than 0.05, were considered differentially expressed [Benjamini Y. and Y. Hochberg Journal of the royal statistical society. Series B (Methodological) (1995) 289-300]. Venn diagrams were generated using the online tool at bioinformatics.psb.ugent.be/webtools/Venn/. Functional annotation of the significant expressed genes was extended using PANTHER (www(dot)pantherdb(dot)org/), based on gene ontology (GO) categories assigned to the human. The KEGG database (www(dot)genome(dot)jp/kegg/) was used for pathways analysis using the KEAGG mapper tool (www(dot)genome(dot)jp/kegg/tool/map_pathway2(dot)html).

Statistical Analyses

Results are presented as mean±SE of replicate analyses and are either representative of or include at least two independent experiments. Means of replicates were subjected to statistical analysis by Tukey-Kramer test (P≤0.05) using the JMP statistical package and considered significant when P≤0.05.

For dose response assays, data points were connected by non-linear regression lines of the sigmoidal dose-response relation. GraphPad. Prism was employed to produce dose-response curve and $IC_{50}$ doses. Flowjo software was used to analyze FACS data.

Example 1

Figure 1C:
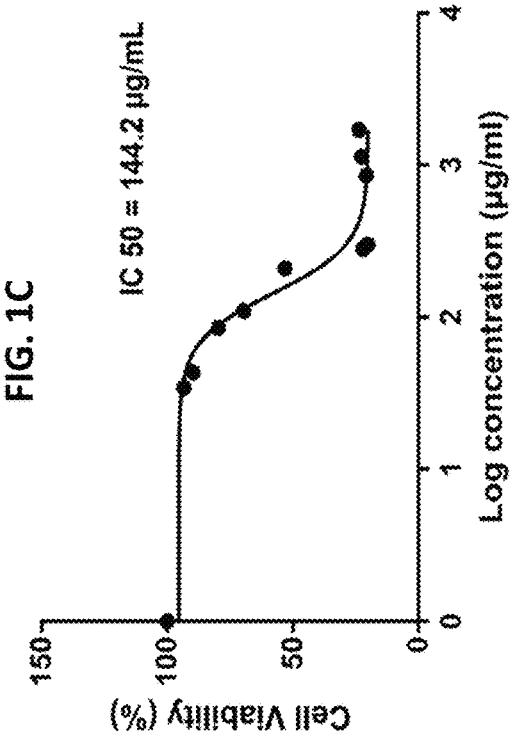
Figure 1D:
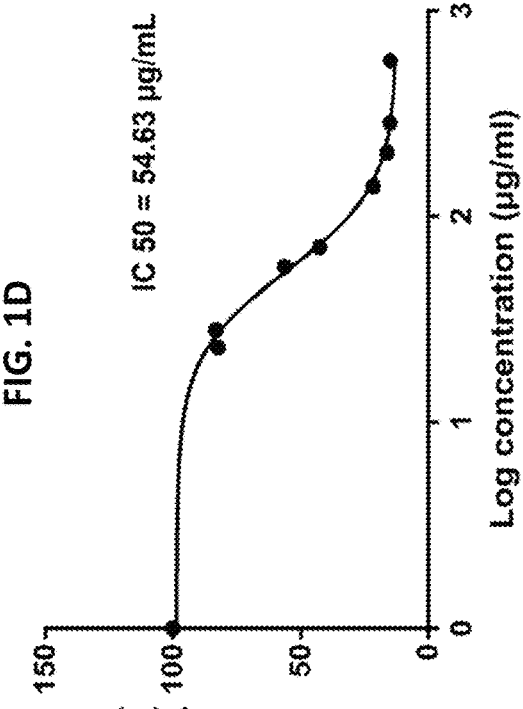
Figure 1A:
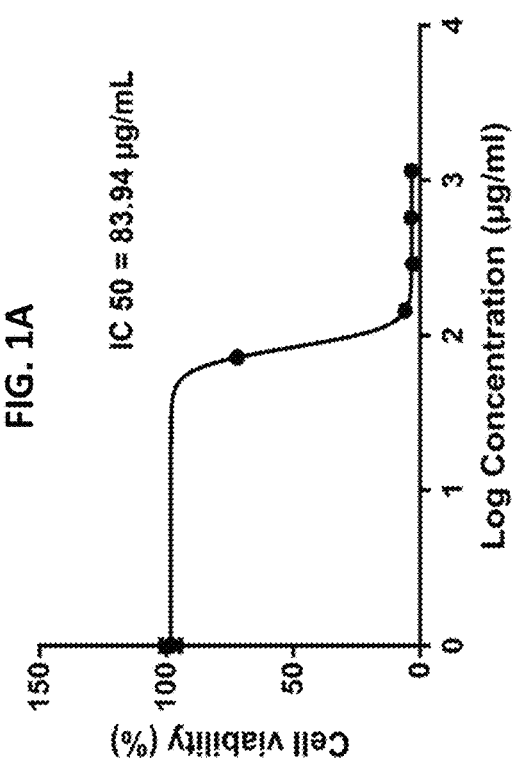
Figure 1B:
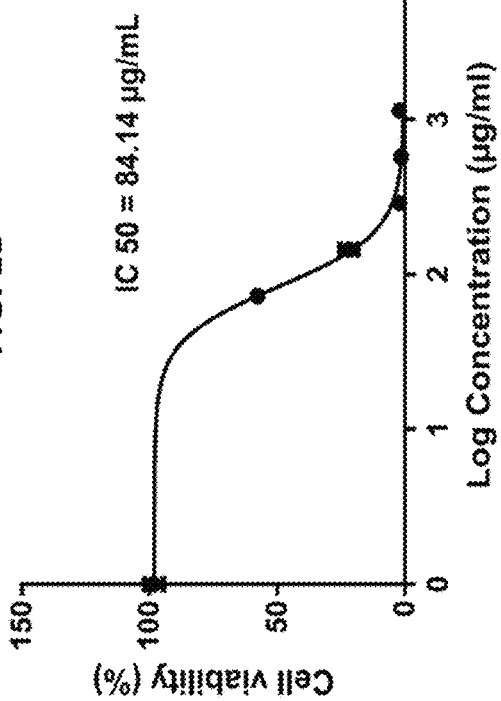

C. sativa Extracts from Fresh Inflorescences are Active in Reducing Cell Viability in Colon Cancer Cell Lines Cytotoxic activity was determined as the level of cell viability in HCT116 cells for absolute ethanol extracts of fresh (C2F) and heated (C2B) inflorescences of C. sativa (CS12 var.) following overnight treatment. Treatments with C2F or C2B were found to significantly reduce HCT116 cancer cell viability with a similar level of activity (FIGS. 1A, 1B). Moreover, although both ethanol-extracts of C. sativa, C2F and C2B, have similar cytotoxic activity on colon cancer cells HCT116 (FIGS. 1A, 1B), the activity of C2F on CCD18 healthy colon cells was reduced. C2F had $IC_{50}$ of 83.9 and 144.2 µg/mL on HCT116 and CCD18 cell lines, respectively (FIGS. 1A, 1C). On the other hand, C2B was more active on CCD18 than on HCT116 cell lines, with $IC_{50}$ of 54.63 and 84.1 µg/ml, respectively (FIGS. 1D, 1B).

Example 2

Chemical Composition of C. sativa Extracts from Fresh and Baked Flowers

HPLC chromatogram and main active compounds were determined for C2F and for C2B (FIGS. 2A-B and Table 1, below).

TABLE 1

HPLC peak area and % of area for *Cannabis* fresh and baked flowers

| | C2F | | Known | | C2B | | Known |
|---|---|---|---|---|---|---|---|
| RT | Area of peak | % of Area | compound | RT | Area of peak | % of Area | compound |
| 5.934 | 5640210 | 0.42 | CBD | 5.947 | 9625348 | 1.15 | CBD |
| 6.449 | 3614080 | 0.27 | CBG | 6.466 | 84359176 | 10.11 | CBG |
| 10.547 | 115095840 | 8.72 | CBDA | 10.229 | 2565112 | 0.30 | CBDA |
| 11.666 | 3592090 | 0.27 | CBN | 10.931-11.339 | 100784260 | 12.08 | CBN |
| 13.193 | 25512280 | 1.93 | CBGA | 13.146 | 518303552 | 62.13 | THC |
| 14.063 | 1476178 | 0.11 | THC | 17.575 | 22981120 | 2.75 | CBC |
| 29.539 | 1006329152 | 76.29 | THCA | | | | |

Eight major cannabinoids were identified in the fresh and baked crude extracts at 220 nm. These peaks were identified as CBD, CBG, CBDA, CBN, CBGA, THC, CBC and THCA, with retention times of 5.9, 6.4, 10.5, 11.6, 13.1, 14.0, 17.5 and 29.5 minutes, respectively, relative to the HPLC profile of cannabinoid standards (not shown). The levels of CBD, CBG, CBN and THC were 2.7, 37.4, 44.7 and 560 times higher in the C2B versus C2F extract respectively. CBC was not identified in C2F but appeared in C2B. THCA was not identified in C2B and CBDA level was reduced 30 times in C2B, compared to C2F (FIG. 2 and Table 1, above), due to decarboxylation of CBDA and THCA during heating. CBD, CBG and THC were found in C2B whereas in C2F the acidic forms of all the above compounds (i.e., CBDA, CBGA, THCA) were mostly present.

Example 3

Identification of an Active Fraction of the Fresh Flower Extract of *C. sativa* and the Effect of Combinations with Whole Extract C2F (at a concentration of 163 µg/mL) was fractionated (FIG. 3A) by HPLC. Fractions were collected and high concentrations (0.9 mg/ml) were examined for cytotoxic activity, determined by cell viability in HCT116 cells.

Subsequently, C2F and F7 activities were compared on HCT116 cells by dilution of extracts and examination of cytotoxic activities of C2F, F7, F1-F9 pool-without F7 and combined treatment of all fractions, including F7 (FIGS. 3B and 3C).

A marked induction of cytotoxicity was found for combined treatment of F1-F9-excluding F7 and addition of F7 at concentrations of 190 and 190 µg/mL, respectively, and even more profoundly, at concentrations of 163 and 190 µg/mL, for F1-F9-excluding F7 and F7, respectively (FIG. 3C). These results suggest that certain combinations of treatment with all fractions of the extract lead to a significant increase in the cytotoxic activity (within a short period of treatment, i.e. 4 hours).

Example 4

The Active Fraction of *C. sativa* Extract Contains Mainly THCA

The chemical composition of the active fraction (F7) was analyzed by HPLC and electrospray ionization mass spectrometry (ESI-MS). F7 was obtained as a broad peak in the HPLC chromatogram. To analyze its structure and verify its purity, it was analyzed at different dilutions, in comparison to a THCA standard. The results suggested that F7 is THCA (FIG. 4). ESI-MS results further confirmed that F7 contains THCA: $C_{22}H_{30}O_4$ (358.214); m/z (MH+) 359.222, (MNa+) 381.203. $^1H$ and $^{13}C$ spectra were taken to verify the exact structure and determine the purity of F7. The NMR results showed that F7 is indeed THCA, at a purity range of 80-95%. Of note, different samples of F7 (from different collections) were taken for analysis in two different methods, thus the difference between the purities. In GC/MS, the purity is an average of 5 different samples.

Example 5

The Chemical Composition of Fractions F3 and F7

Further analysis of fractions F7 and F3 illustrate that F3 contains three cannabinoids (CBCA, CBGA and CBN), different terpenes (Aromadendrene), and terpenes alcohols (Ditertbutylphenol, Epicedrol, alpha-Bisabolol, Lupeol), phyto-sterol (Phytol) and fatty acids (Table 2). F7 contains THCA, THC, CBD and CBN, additional acids (palmitic acid, Linolenic acid, malic acid, Arachidonic acid, stearic acid and myristic acid) and compounds as detailed in Table 3.

TABLE 2

Composition for Fraction 3 (F3) as repeatedly collected from the analytical HPLC (summarized results from 5 repeats) and analyzed using GC/MS with NIST 14.0

| Ret Time | Area | Compound id | Comments | % | of 1 gr fresh flower mg/mL |
|---|---|---|---|---|---|
| 21.252 | 3073938 | Ditertbutylphenol | terene alcohol | 0.167247 | 0.007288 |
| 24.26 | 977059 | Aromadendrene | terpene | 0.05316 | 0.002316 |
| 24.544 | 1208619 | Epicedrol | terene alcohol | 0.065759 | 0.002865 |
| 24.734 | 2520761 | alpha-Bisabolol | terene alcohol | 0.13715 | 0.005976 |
| 25.584 | 645565 | methyl octenal | | 0.035124 | 0.001531 |

TABLE 2-continued

Composition for Fraction 3 (F3) as repeatedly collected from the analytical HPLC (summarized results from 5 repeats) and analyzed using GC/MS with NIST 14.0

| Ret Time | Area | Compound id | Comments | % | of 1 gr fresh flower mg/mL |
|---|---|---|---|---|---|
| 25.754 | 1147177 | Lupeol | terene alcohol | 0.062416 | 0.00272 |
| 27.317 | 608736 | Glutaric acid | | 0.03312 | 0.001443 |
| 28.882 | 515493 | stearic caid ME | C18:0ME | 0.028047 | 0.001222 |
| 31.721 | 3497897 | tridieneoctadecanoic acid | C18:3 | 0.190314 | 0.008293 |
| 31.893 | 4062508 | Phytol | phyto-sterol | 0.221034 | 0.009632 |
| 36.496 | 43747540 | CBCA | | 2.380223 | 0.103718 |
| 38.582 | 1730440744 | CBGA | | 94.15008 | 4.10259 |
| 38.739 | 45513956 | CBN | | 2.47633 | 0.107906 |
| total area | 1837959993 | | | | |

TABLE 3

Composition for Fraction 7 (F7) as repeatedly collected from the analytical HPLC (summarized results from 5 repeats) and analyzed using GC/MS with NIST 14.0
C2F_F7

| Compounds | % | of 1 gr fresh flower mg/mL |
|---|---|---|
| D-Limonene | 0.097 | 0.036011 |
| Glycerol | 0.086 | 0.031928 |
| β-Caryophyllene | 0.103 | 0.038239 |
| Humulene | 0.03 | 0.011138 |
| malic acid | 0.035 | 0.012994 |
| α-Farnesene | 0.034 | 0.012623 |
| myristic acid | 0.023 | 0.008539 |
| palmitic acid ME | 0.014 | 0.005198 |
| palmitic acid | 0.514 | 0.190823 |
| alkane | 0.015 | 0.005569 |
| Linolenic acid | 0.074 | 0.027473 |
| Linoleic acid | 0.388 | 0.144045 |
| stearic acid | 3.135 | 1.163869 |
| Arachidonic acid | 0.022 | 0.008168 |
| CBD | 0.036 | 0.013365 |
| Cholesterol | 0.499 | 0.185254 |
| THC | 1.724 | 0.640035 |
| THCA | 83.172 | 30.87761 |
| CBG | 1.399 | 0.519379 |
| CBN | 3.537 | 1.313111 |
| b-sitosterol | 1.697 | 0.630011 |
| stigmasterol | 1.468 | 0.544995 |
| silyl | 1.184 | 0.43956 |
| alkane | 0.714 | 0.265073 |
| | | 37.125 |

Of note:
all samples were introduced to GC/MS after silylation with 100 μL BSTFA with 1% TMCS Example 6

C2F and F7 have Cytotoxic Activity on Human Colon Polyp Biopsies

Adenomatous polyps are the primary premalignant precursors of CRC. Hence, to examine a possibility for a therapeutic or preventive potential of the extracts, biopsies of adenomatous polyps and healthy tissue from patients scheduled for colonoscopy were studied. Biopsy tissues of polyps and normal colon tissue of the same patient were exposed to C2F and F7 for 16 hours followed by cell separation and Resazurin assay to determine tissue cell viability. Both C2F and F7 treatments (at the tested concentrations) reduced to some extent cell viability of polyp and healthy tissues (Table 4, below).

TABLE 4

C. sativa C2F and F7 cytotoxic activity on human colon polyp and healthy colon tissue as % of living cells from control of tissue treated with only methanol (NT + MeOH)

| Sample | Treatment | % Living cells | Statistics |
|---|---|---|---|
| Healthy | NT + MeOH | 100 | A |
| | C2F (1.25 mg/mL) | 18.41 | B |
| | F7 (0.4 mg/mL) | 18.43 | B |
| Polyp | NT + MeOH | 100 | a |
| | C2F (1.25 mg/mL) | 7.81 | b |
| | F7 (0.4 mg/mL) | 13.30 | b |

Of note:
Healthy—biopsy of normal tissue, n = 3; Polyp—biopsy of adenomatous polyp, n = 3.

Example 7

F7 Interaction with Other C. sativa Cannabis Fractions Induce Cytotoxic Activity Since C2F is as active as C2B on cancer cells but is less active on normal cell line (see Example 1, above), the preset inventors have further analyzed C2F for cytotoxic activity. Previously it was shown that the HPLC fraction 7 of C2F F7 (that contains mainly THCA) has only moderate cytotoxic activity against HCT116. However, combination of F7 with the other C2F fractions led to a marked increase in cytotoxic activity (FIGS. 3B and 3C, above). Here, the interaction between F7 and the other C. sativa C2F fractions was further examined for each fraction separately.

Overnight treatment with F7 led to only a moderate effect on cell viability, however, combinations of F7 with F2 or F3 was found to have increased cytotoxic activity (FIG. 5A). Only combination of F7 and F3 (in concentrations found in C2F) resulted in increased cytotoxic activity despite the low (F3) to moderate (F7) activity of each (FIG. 5B). Both F7 and F7+F3 treatments were cytotoxic to HT29 and CACO2 cell lines (FIGS. 6A-B). As expected, F7+F2 or F7+F3 were much less potent on the normal CCD18 cell line (FIG. 6C).

Example 8

Synergistic Interaction of C. sativa Cannabis Fractions F7 and F3 and F3 Chemical Composition To determine whether the interaction of F7 and F3 is synergistic, i.e., their combined activity is greater than the sum of their separate activities, the extent of their activity was examined once F7 and F3 were combined at different concentrations. The $IC_{50}$ of F7 and F3 were determined to be 20.42 and 36.03 μg/ml, respectively (FIGS. 7E and 7D). Next, the partial effect of the drugs was calculated according to the Bliss independence model for each combination experiment. Five concentrations of each combination were examined. Synergistic interaction was found for the following combinations: F7 at its $IC_{50}$+F3 at concentrations of 26.67, 20, 13.3 μg/ml and F3 at its $IC_{50}$+F7 at concentrations of 15.8, 11.9, 7.9 μg/ml (FIGS. 7A-B). Furthermore, combination of F3 at its $IC_{50}$ with F7 resulted with a reduction of about 3 fold in F3 $IC_{50}$ (from 36.03 to 10.8 μg/ml; FIG. 7A). Combination of F7 at its $IC_{50}$ with F3 resulted with a reduction of 11-fold in F7 $IC_{50}$ (from 20.42 to 1.9 μg/ml; FIG. 7B).

As discussed in Example 5, above, F3 was found to contain mainly CBGA (at 94.15%), CBN (2.47%), CBCA (2.38%), terpenes and terpene-ethanol compounds (0.48%), diterpenes (0.22%), acids (0.03%) and short free fatty acids (FAA; 0.21%). The rest (0.06%) of compounds present in F3 are unidentified.

Moreover, activity of the purified compounds that constitute most of the fractions, i.e., THCA in F7 and CBGA in F3, resulted with synergistic interactions (synergistic interactions marked in red in FIG. 7C).

Example 9

Treatment of HCT116 Cells with *C. sativa* F7 and F7+F3 Induced Apoptotic Cell Death Cell sorting for cell viability by FACS based on Alexa Fluor® 488/annexin V staining suggested that treatment for 48 hours with F7 lead to a large proportion of cells that are in early or late apoptosis in comparison to controls (non-treated and TNF-α or Methanol [MeOH] treated cells). This proportion was even significantly higher in F7+F3 treated cell at 48 hours, however treatment with F3 alone did not lead to cell death (FIGS. 8A-D). At 24 hours apoptosis was not yet evident, however a slight but significant reduction of cell necrosis was found with the F7+F3 treatment (FIGS. 8A-D). These results suggest that F7 or F7+F3 treatments may act via induction of apoptosis.

Example 10

Treatment of HCT116 Cell Line with *C. sativa* F7 or F7+F3 Lead to S or G0/G1 Cell Cycle Arrest, Respectively Cell sorting for cell cycle analysis by FACS based on propidium iodide staining suggested that treatment of the cells with F7+F3 led (at 24 hours) to a marked increase in proportion of cells in G0/G1 phase in comparison to controls (non-treated [NT] and treated with TNF-α or MeOH; FIG. 9). Treatment with F7 or F3 (F3 to a lesser extent) led to an increase in cells in S phase in comparison to controls (FIG. 9).

Example 11

F7 and F7+F3 have Cytotoxic Activity on Human Colon Polyp Biopsies

Next it was examined whether treatment with both F7+F3 lead to an increase in the cytotoxic activity. For that purpose, biopsy tissues of polyps and normal colon tissue (of the same patient) were treated with reduced concentrations of F7, F3 or F7+F3 for 16 hours followed by cell separation and Resazurin assay to determine tissue cell viability. Results varied between patients (n=4). In some, F7+F3 treatment was more effective than F7 or F3 alone, whereas in others treatment with F7+F3 did not improve cytotoxicity in comparison to F7 or F3 alone (Table 5, below). Yet, in all cases but one (P4), treatments reduced polyp cell viability.

TABLE 5

*C. sativa* F7, F3 and F7 + F3 cytotoxic activity on human colon polyp and healthy colon tissue as % of living cells from control of tissue treated with only methanol (NT + MeOH)

% Living cells

| Sample | | P1 | P2 | P3 | P4 |
|---|---|---|---|---|---|
| Healthy tissue | NT | $100^A$ | $100^A$ | $100^A$ | $100^B$ |
| | F3 | $68.5^B$ | $51.3^B$ | $18.1^B$ | $122.5^A$ |
| | F7 | $54.4^C$ | $25.2^C$ | $4.9^C$ | $97.3^C$ |
| | F3 + F7 | $55.4^{BC}$ | $30.0^C$ | $7.6^C$ | $16.3^D$ |
| Polyp | NT | $100^a$ | $100^a$ | $100^a$ | $100^c$ |
| | F3 | $24.4^b$ | $77.2^b$ | $13.0^c$ | $119.7^b$ |
| | F7 | $15.4^c$ | $63.4^{bc}$ | $5.8^d$ | $142.1^a$ |
| | F3 + F7 | $16.1^c$ | $51.7^c$ | $33.5^b$ | $40.6^d$ |

Of note:

Healthy—biopsy of normal tissue (n = 4); Polyp—biopsy of adenomatous polyp (n = 4). Percentages with different letters are significantly different from all combinations of pairs by Tukey HSD.

Example 12

F7+F3 Treatment Induces a Distinct Profile of Gene Expression in HCT116 Cells in Comparison to F7 or F3 Treatments To identify genes differentially expressed in HCT116 cells following treatment with *C. sativa* extract fractions, RNA sequence analysis of HCT116 cells was performed, 6 hours post treatment with F7, F3 or F7+F3. Sample correlation test of RNA sequencing results suggested that the 3 replicates of sequencing done for cells treated with F7 or F3 were clustered together, and the 3 replicates of control treatment clustered in a separate Glade. However, the 3 replicates of the treatment with F7+F3 at concentrations that were shown above to act synergistically were clustered together as an outgroup Glade to the rest of the treatments (FIG. 10A).

2283 genes were found to be differentially expressed in cells treated with F7+F3, but not in cells treated with F7 or F3 alone, in comparison to control (FIG. 10B, and data not shown). Among the differentially expressed genes that are specific to the F7+F3 treatment are those involved with cell cycle G1/S phase transition, Wnt signaling pathway (FIG. 11A), and p53 and apoptosis signaling pathways (FIG. 11B). F7+F3 treatment (but not F7) suppressed 14 out of 18 differentially expressed genes involved with G1/S transition (data not shown). F7+F3 treatment reduced most (11/14) differentially expressed genes related to Wnt signaling pathway (FIG. 11A; and data not shown) and affected the expression of apoptosis related genes (FIG. 11B; and data not shown).

Example 13

CB2 Receptor Antagonist Significantly Reduces Cytotoxic Activity

To determine whether C2F and F7 activity in HCT116 cells is conferred via the CB receptors, the effects of CB1, CB2 and GPR55 receptor antagonists (Rimonabant, SR144528 and CID16020046, respectively) on the cytotoxic activity was determined. CB2 antagonist lead to a significant reduction in cytotoxic activity of C. sativa extracts C2F, F7 and THCA in HCT116 cells, whereas CB1 antagonist lead to a significant reduction in cell cytotoxic activities of THCA only (FIGS. 12A-C). Moreover, a significant reduction in F1-F9-excluding F7 with addition of F7 (163 and 190 µg/mL, respectively) activity was found for CB2 antagonist. However, CB2 antagonist increases cell number even in the control (FIG. 12D), suggesting that it counteracts the fractions' activity by inducing HCT116 cell proliferation (FIG. 12D).

Transcripts for CB1, CB2 and GPR55 were detected by qPCR in HCT116 cells. Expression of CB2 and GPR55 were significantly increased upon treatment with TNF-α in these cells (values are the steady-state level of gene expression in TNF-α-treated versus non-treated cells; Table 6 below).

TABLE 6

Relative gene expression in HCT-116 cells. CB1, CB2 and GPR55 gene expression was measured following overnight treatment of the cells with TNF-α. Values of gene transcripts were determined as a ratio between target genes (CB1, CB2 and GPR55) versus a reference gene (GAPDH), using the 2-ΔΔCT method

| Gene | Mean relative expression | Std Err | Statistics |
|---|---|---|---|
| CB1 | 1.31 | 0.19 | AB |
| CB2 | 5.84 | 1.04 | A |
| GPR55 | 5.26 | 1.57 | B |

Example 14

The Activity of Fractions of C. sativa and Combinations Thereof on Breast Cancer Cell Line MDA-MB231 and Glioblastoma Cell Line A172

As illustrated in FIGS. 13A-B, an increase in the cytotoxic effect is evident in treatment of breast cancer cells with the combination F3 and F7. Drug synergy was determined by Bliss independence drug interaction model. Three concentrations of each combination were examined. The present inventors have found synergistic interaction for the following combinations: F3 (59 µg/ml)+F7 at concentrations of 23.8, 15.8 and 11.9 µg/ml (Table 7, below).

TABLE 7

Experimental and calculated values of XTT experiment according to bliss model for combination of constant F3 and different concentrations of F7 on MDA-MB-231 cells

| | F3 - 59 µg/mL | | |
|---|---|---|---|
| | F7 - 23.8 µg/mL | F7 - 15.8 µg/mL | F7 - 11.9 µg/mL |
| Calculated value | 95.29 | 77.94 | 76.92 |
| Experimental value | 5.82 | 7.76 | 25.20 |

As illustrated in FIGS. 14A-B, an increase in the cytotoxic effect is evident in combination treatment with F3 and F7 on glioblastoma cells. Eight concentrations of each combination were examined. The present inventors have found synergistic interaction for the following combinations: F7 at 50 µg/ml+F3 at concentrations of 40, 26.67, 20, 13.33, 10, 6.67, 5 and 3.33 µg/ml.

TABLE 8

Experimental and calculated values of XTT experiment according to bliss model for combination of constant F7 and different concentrations of F3 on A172 cells

| | F7 - 50 µg/mL | | | | | | | |
|---|---|---|---|---|---|---|---|---|
| | F3 - 40 µg/mL | F3 - 26.67 µg/mL | F3 - 20 µg/mL | F3 - 13.33 µg/mL | F3 - 10 µg/mL | F3 - 6.67 µg/mL | F3 - 5 µg/mL | F3 - 3.33 µg/mL |
| Calculated value | 37.42 | 39.14 | 40.15 | 40.54 | 39.59 | 36.84 | 37.75 | 34.51 |
| Experimental value | 4.43 | 18.75 | 33.97 | 29.04 | 22.67 | 28.68 | 23.70 | 25.35 |

Example 15

Synergistic Effect of Standards (THCA and CBGA) in Anti-Cancer Activity in HCT116 Cells The synergy between the standards (CBGA and THCA) was examined. Six concentrations of each combination were examined. As illustrated in Table 9, below, synergistic interactions were found for the following combinations: THCA at a constant concentration of 13.14 µg/ml+CBGA at concentrations of 40, 28, 20, 13.3 and 6.67 µg/ml as shown. Marked in bold are concentrations which show synergism.

TABLE 9

Experimental and calculated values of XTT experiment according to bliss model for combination of constant THCA and different concentrations of CBGA on HCT116 cells

| | THCA - 13.14 µg/ml | | | | | |
|---|---|---|---|---|---|---|
| | CBGA - 53.3 µg/ml | CBGA - 40 µg/ml | CBGA - 28 µg/ml | CBGA - 20 µg/ml | CBGA - 13.3 µg/ml | CBGA - 6.67 µg/ml |
| Calculated value | 15.10 | 17.69 | 22.97 | 50.19 | 44.37 | 52.49 |
| Experimental value | 15.69 | 15.15 | 16.89 | 16.86 | 19.29 | 19.44 |

Furthermore, as illustrated in Table 10, seven concentrations of each combination were examined. Synergistic interactions were found for the following combinations: CBGA at a constant concentration of 28 µg/ml+THCA at concentrations of 30, 25, 15, 12, 6 and 4 µg/ml. Marked in bold are concentrations which show synergism.

TABLE 10

Experimental and calculated values of XTT experiment according to bliss model for combination of constant CBGA and different concentrations of THCA on HCT116 cells

| | CBGA (28 µg/ml) | | | | | | |
|---|---|---|---|---|---|---|---|
| | THCA - 50 µg/ml | THCA - 30 µg/ml | THCA - 25 µg/ml | THCA - 15 µg/ml | THCA - 12 µg/ml | THCA - 6 µg/ml | THCA - 4 µg/ml |
| Calculated value | 10.53 | 20.43 | 21.25 | 44.66 | 47.60 | 70.59 | 69.18 |
| Experimental value | 16.56 | 14.40 | 16.90 | 23.25 | 28.69 | 29.68 | 42.44 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a colorectal cancer in a subject in need thereof, the method comprising administering to the subject a therapeutically effective amount of a composition comprising tetrahydrocannabinolic acid (THCA) and cannabigerolic acid (CBGA), wherein said composition is devoid of cannabidiolic acid (CBDA), thereby treating the colorectal cancer in the subject.

2. The method of claim 1, wherein said composition comprises a liquid chromatography pooled fractions of cannabis extract comprising said THCA and CBGA detectable by a detector operated at 220 nm.

3. The method of claim 1, wherein said THCA comprises a liquid chromatography fraction of a cannabis extract, said fraction comprising at least 75% THCA, wherein said fraction comprises cannabis derived active ingredients other than said THCA; and said CBGA comprises a liquid chromatography fraction of a cannabis extract, said fraction comprising at least 75% CBGA, wherein said fraction comprises cannabis derived active ingredients other than said CBGA.

4. The method of claim 1, wherein said THCA comprises a liquid chromatography fraction of a cannabis extract, said fraction comprising at least 75% tetrahydrocannabinolic acid (THCA), wherein said fraction comprises cannabis derived active ingredients other than said THCA.

5. The method of claim 3, wherein said fraction comprising said THCA comprises 80-95% THCA.

6. The method claim 1, wherein the composition comprises at least one of D-Limonene, β-Caryophyllene, Humulene, malic acid, α-Farnesene, cannabinol (CBN), Δ9-tetrahydrocannabinol (THC), and/or cannabigerol (CBG).

7. The method of claim 1, wherein said composition comprises at least two of D Limonene, β-Caryophyllene, Humulene, malic acid, α-Farnesene, cannabinol (CBN), Δ9-tetrahydrocannabinol (THC), and/or cannabigerol (CBG).

8. The method of claim 1, wherein said composition comprises D-Limonene, Glycerol, β-Caryophyllene, Humulene, malic acid, α-Farnesene, myristic acid, palmitic acid ME, palmitic acid, alkane, Linolenic acid, stearic acid, Arachidonic acid, Cholesterol, b-sitosterol, stigmasterol, silyl, alkane, cannabidiol (CBD), Δ9-tetrahydrocannabinol (THC), cannabigerol (CBG) and cannabinol (CBN).

9. The method of claim 1, wherein said CBGA comprises a liquid chromatography fraction of a cannabis extract, said fraction comprising at least 75% cannabigerolic acid (CBGA), wherein said fraction comprises cannabis derived active ingredients other than said CBGA.

10. The method of claim 3, wherein said fraction comprising said CBGA comprises 80-95% CBGA.

11. The method of claim 1, wherein said composition comprises at least one of Aromadendrene, Epicedrol, alpha-Bisabolol, Lupeol, CBCA and/or CBN.

12. The method of claim 1, wherein said composition comprises Aromadendrene, Epicedrol, alpha-Bisabolol, Lupeol, CBCA and CBN.

13. The method of claim 1, wherein said composition comprises at least one of Diterbutylphenol, Aromadendrene, Epicedrol, alpha-Bisabolol, methyl octenal, Lupeol, Glutaroic acid, stearic acid ME, tridieneoctadecanoic acid, Phytol, cannabichromenic acid (CBCA) and cannabinol (CBN).

14. The method of claim 3, wherein said liquid chromatography comprises high pressure liquid chromatography (HPLC).

15. The method of claim 3, wherein said liquid chromatography is performed on a reverse stationary phase.

16. The method of claim 3, wherein said extract is obtained from a fresh plant.

17. The method of claim 3, wherein said extract is an ethanol extract.

18. The method of claim 2, wherein said liquid chromatography comprises high pressure liquid chromatography (HPLC).

19. The method of claim 2, wherein said extract is obtained from a fresh plant.

20. The method of claim 2, wherein said extract is an ethanol extract.

* * * * *